(12) United States Patent
Yang et al.

(10) Patent No.: US 8,114,904 B2
(45) Date of Patent: Feb. 14, 2012

(54) LUMINESCENCE QUENCHERS AND FLUOROGENIC PROBES FOR DETECTION OF REACTIVE SPECIES

(75) Inventors: Dan Yang, Hong Kong (HK); Tao Peng, Hong Kong (HK)

(73) Assignee: Versitech Limited & Morningside Ventures Limited, Hong Kong (CN)

( * ) Notice: Subject to any disclaimer, the term of this patent is extended or adjusted under 35 U.S.C. 154(b) by 312 days.

(21) Appl. No.: 12/417,672

(22) Filed: Apr. 3, 2009

(65) Prior Publication Data

US 2009/0253118 A1    Oct. 8, 2009

Related U.S. Application Data

(60) Provisional application No. 61/042,720, filed on Apr. 5, 2008.

(51) Int. Cl.
  *C07D 265/38* (2006.01)
  *C07D 407/04* (2006.01)
  *C12Q 1/00* (2006.01)

(52) U.S. Cl. ........ 514/454; 549/225; 549/226; 514/455; 544/102; 435/14; 436/172

(58) Field of Classification Search ............... 549/225, 549/226; 514/454, 455
See application file for complete search history.

(56) References Cited

U.S. PATENT DOCUMENTS

| | | | |
|---|---|---|---|
| 3,920,510 | A | 11/1975 | Hatano et al. |
| 4,433,156 | A | 2/1984 | Ishige et al. |
| 6,399,392 | B1 | 6/2002 | Haugland et al. |
| 7,087,766 | B2 | 8/2006 | Nagano et al. |
| 2004/0229371 | A1 | 11/2004 | Setsukinai et al. |
| 2006/0105412 | A1 | 5/2006 | Maeda et al. |
| 2007/0141658 | A1 | 6/2007 | Chang |

FOREIGN PATENT DOCUMENTS

WO    WO2004078030 A2    9/2004

OTHER PUBLICATIONS

Belinda Heyne et al., Synthesis and characterization of a new fluorescent probe for reactive oxygen species, Org. Biomol. Chem., 2007, 5, 1454-1458.

*Primary Examiner* — Kahsay T Habte
(74) *Attorney, Agent, or Firm* — Saliwanchik, Lloyd & Eisenschenk

(57) ABSTRACT

Provided herein are compounds or fluorogenic probes which can be used as reagents for measuring, detecting and/or screening ROS or RNS such as peroxynitrite or hypochlorite. Provided also herein are methods that can be used to measure, directly or indirectly, the amount of peroxynitrite or hypochlorite in chemical samples and biological samples such as cells and tissues in living organisms. Specifically, the methods include the steps of contacting the fluorogenic probes disclosed herein with the samples to form one or more fluorescent compounds, and measuring fluorescence properties of the fluorescent compounds. Provided also herein are high-throughput screening fluorescent methods for detecting or screening peroxynitrite or compounds that can increase or decrease the level of peroxynitrite or hypochlorite in chemical and biological samples.

10 Claims, 11 Drawing Sheets

US 8,114,904 B2

LUMINESCENCE QUENCHERS AND FLUOROGENIC PROBES FOR DETECTION OF REACTIVE SPECIES

PRIOR RELATED APPLICATIONS

This application claims priority to U.S. Provisional Patent Application Ser. No. 61/042,720, filed Apr. 5, 2008, which is incorporated herein by reference in its entirety.

FIELD

Provided herein are aromatic amine compounds which can be used as luminescence quenchers and/or fluorogenic probes for measuring, detecting or screening reactive nitrogen species (RNS) such as peroxynitrite or reactive oxygen species (ROS) such as hypochlorite. Also provided herein are methods of making the aromatic amine compounds and methods of using the aromatic amine compounds.

BACKGROUND

Luminescence is generally the emission of light that does not derive energy from the temperature of the emitting body. Luminescence may be caused by chemical, biochemical, or crystallographic changes, the motions of subatomic particles, or radiation-induced excitation of an atomic or molecular system. Luminescence quenching refers to any process which can decrease the luminescence intensity of a given luminophore. A variety of processes can result in luminescence quenching, such as excited state reactions, energy transfer, complex formation and collisional quenching.

The luminescence quenching process, especially the fluorescence quenching process, through energy transfer has been well studied. When a first fluorophore is excited and transfers its absorbed energy to a second fluorophore, the energy transfer results in fluorescent signal at the emission wavelength of the second fluorophore. However, where the second fluorophore shows no fluorescence, the absorbed energy does not result in fluorescence emission, and the first fluorophore is said to be "quenched". Similarly, energy transfer can also be utilized to quench the emission of other luminescent donors such as phosphorescent and chemiluminescent donors.

The use of a variety of dyes containing at least a luminophore to quench luminescence such as fluorescence is known in the art. The application of luminescence quenching to analyze biological systems is also well-studied. However, there is always a need for luminescence quenchers having different absorption properties to meet the various requirements of new advances in this field.

Reactive oxygen species (ROS) and reactive nitrogen species (RNS) are generally known to scientists as very small inorganic or organic molecules with high reactivity. There are various forms of ROS and RNS including free radicals such as superoxide radical, hydroxyl radical, nitric oxide, nitrogen dioxide and organic peroxyl radical as well as non-radical species such as hydrogen peroxide, singlet oxygen, ozone, nitrous acid, peroxynitrite and hypochlorite. ROS and RNS are the by-products of cellular respiration. Under normal conditions ROS and RNS are present in very low levels and play important roles in cell signaling, while during oxidative stresses, ROS and RNS levels increase dramatically, which can cause serious damages to various biological molecules such as protein, lipids and DNA. The excessive generation of ROS and RNS has been implicated in a lot of human diseases, such as cardiovascular diseases, inflammatory diseases, metabolic diseases, cancer and central nervous system diseases. Therefore, there is a strong need for chemicals that can sensitively and selectively measure, detect or screen certain ROS and RNS to address their physiological roles both in vitro and in vivo.

Peroxynitrite and hypochlorite have the strongest oxidizing power among the various forms of ROS and RNS, and their selective detections are highly desirable to clearly explain their critical roles in living organisms. Peroxynitrite ($ONOO^-$) is a short-lived oxidant species that is formed in vivo by the diffusion-controlled reaction ($k=0.4-1.9\times10^{10}$ $M^{-1}s^{-1}$) of nitric oxide (NO) and superoxide ($O_2^{\cdot-}$) in one to one stoichiometry. The oxidant reactivity of peroxynitrite is highly pH-dependent and both peroxynitrite anion and its protonated form peroxynitrous acid can participate directly in one- and two-electron oxidation reactions with biomolecules. The pathological activity of $ONOO^-$ is also related to its reaction with the biologically ubiquitous $CO_2$, thereby producing the highly reactive radicals $CO_3^{-\cdot}$ and $NO_2^{\cdot}$ in about 35% yield. As a result of this, peroxynitrite can nitrate tyrosine and oxidize proteins, lipids and iron and sulfur clusters of biological molecules. Like other oxidizing agents in living organisms, peroxynitrite and its protonated form have been associated with both beneficial and harmful effects. However, several studies have implicated that peroxynitrite contributes to tissue injury in a number of human diseases such as ischemic reperfusion injury, rheumatoid arthritis, septic shock, multiple sclerosis, atherosclerosis, stroke, inflammatory bowl disease, cancer, and several neurodegenerative diseases (MacMillan-Crow, L. A. et al., *Proc. Natl. Acad. Sci. USA* 1996, 93, 11853-11858; Rodenas, J. et al., *Free Radical. Biol. & Med.* 2000, 28, 374; Cuzzocrea, S. et al., *Pharmacol Rev.* 2001, 53, 135-159; Szabo, C. *Toxicol. Lett.* 2003, 140, 105-112; White, C. R. et al., *Proc. Natl. Acad. Sci. USA* 1994, 91, 1044-1048; Lipton, S. A. et al., *Nature* 1993, 364, 626-632; Pappolla, M. A. et al., *J. Neural Transm.* 2000, 107, 203-231; Beal, M. F., *Free Radical Biol. & Med.* 2002, 32, 797-803).

On the other hand, hypochlorite is produced in vivo from hydrogen peroxide and chlorine ions in a chemical reaction catalyzed by the enzyme myeloperoxidase (MPO), which may be secreted by activated phagocytes in zones of inflammation. As a nucleophilic non-radical oxidant, hypochlorite can be used as a microbicidal agent (Thomas, E. L., *Infect. Immun.*, 1979, 23, 522-53 1). Furthermore, neither bacteria nor normal healthy cells can neutralize its toxic effect because they lack the enzymes required for its catalytic detoxification (Lapenna, D. and Cuccurullo, F., *Gen. Pharmacol.*, 1996, 27, 1145-1147).

Generally, hypochlorite can react with some proteins that may play important roles in killing bacterial cells and/or human diseases (Thomas, E. L., *Infect. Immun.*, 1979, 23, 522-531; McKenna, S. M. and Davies, K. J. A., *Biochem. J.*, 1988, 254, 685-692; Hazell, L. J. and Stocker, R., *Biochem. J.*, 1993, 290, 165-172; Hazell, L. J., van den Berg, J. J. and Stocker, R., *Biochem. J.*, 1994, 302, 297-304). When contacting with proteins, hypochlorite may cause damages to the proteins. For example, hypochlorite may alter protein structures, and/or cause fragmentation and dimerization of proteins. As a strong oxidant, hypochlorite can also oxidize low-density lipoproteins (LDL) rapidly. Furthermore, the reaction of hypochlorite with DNA can also result in both chemical modifications and structural changes in DNA (Hawkins, C. L. and Davies, M. J., *Chem. Res. Toxicol.*, 2002, 15, 83-92; Prutz, W. A., *Arch. Biochem. Biophys.* 1996, 332, 110-120; *Arch. Biochem. Biophys.* 1998, 349, 183-191; *Arch. Biochem. Biophys.* 1999, 371, 107-114).

Because of the above-mentioned uses and roles of ROS and RNS, there is a need for methods that detect, measure and/or screen ROS such as hypochlorite and/or RNS such as peroxynitrite, including in vivo detection and measurement.

SUMMARY

Provided herein are aromatic amine compounds that can be used as luminescence quenchers and/or fluorogenic probes for measuring, detecting or screening reactive nitrogen species (RNS) or reactive oxygen species (ROS) such as $^1O_2$, $O_2^{\cdot-}$, NO, $H_2O_2$, .OH, $^-$OCl, ONOO$^-$ and alkylperoxyl radical (ROO$^\cdot$).

In one aspect, the aromatic amine compounds can be represented by formula (I):

(I)

wherein $R^1$ is hydrogen, alkyl, halogenated alkyl, heteroalkyl, alkenyl, alkynyl, aryl, aralkyl, alkaryl, heterocyclyl, cycloalkyl, cycloalkenyl or cycloalkynyl;

L has one of formulae (II)-(VI)

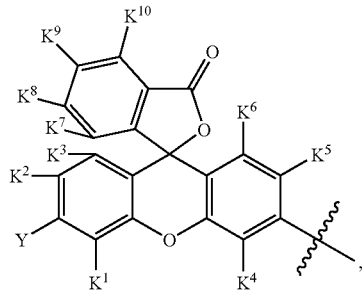
(II)

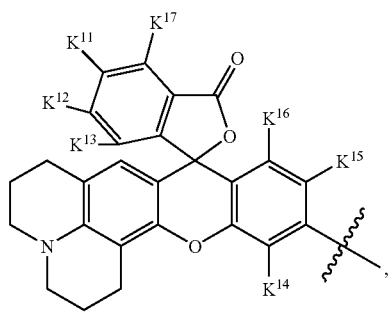
(III)

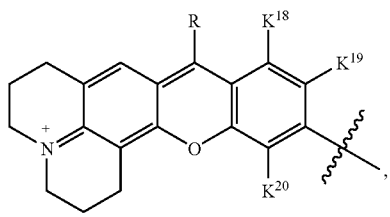
(IV)

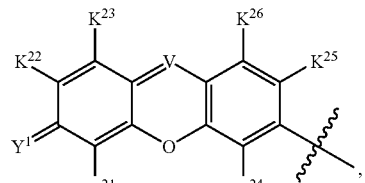
(V)

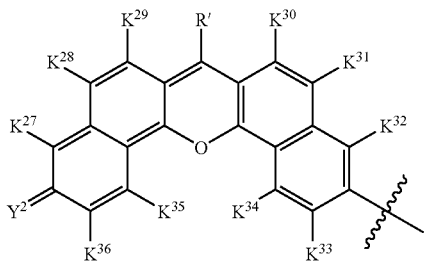
(VI)

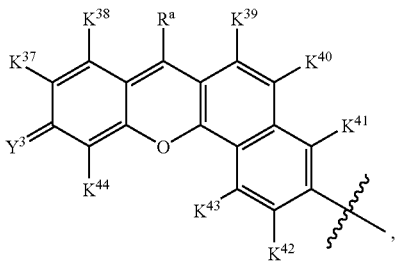
(XX)

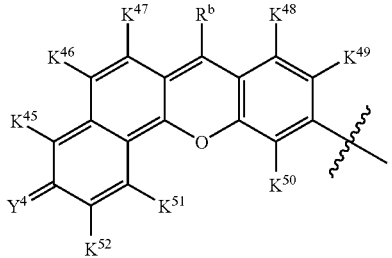
(XXI)

or a tautomer thereof, wherein Y is O-A, S-A or NR$^2$R$^3$;

each of $Y^1, Y^2, Y^3$ and $Y^4$ is independently O, S, NR$^{2'}$R$^{3'}$ or N$^+$R$^{2'}$R$^{3'}$;

V is N or CR″;

each of $R^2$, $R^3$, $R^{2'}$ and $R^{3'}$ is independently H, alkyl, halogenated alkyl, alkenyl, alkynyl, alkoxyalkyl, heteroalkyl, cycloalkyl, cycloalkenyl, cycloalkynyl, heterocyclyl, aminoalkyl, aryl, alkaryl, arylalkyl, alkyloxy, carboxyalkyl, alkylamido, alkoxyamido, sulfonylaryl or acyl;

each of R, R', R″, R$^a$ and R$^b$ is independently H, CN, alkyl, halogenated alkyl, alkenyl, alkynyl, alkoxyalkyl, heteroalkyl, cycloalkyl, cycloalkenyl, cycloalkynyl, heterocyclyl, aminoalkyl, aryl, alkaryl, arylalkyl, alkyloxy, carboxyalkyl, alkylamino, alkoxyamino, alkylamido, alkoxyamido, sulfonylaryl or acyl;

A is H, alkyl, alkenyl, alkynyl, alkoxyalkyl, heteroalkyl, cycloalkyl, cycloalkenyl, cycloalkynyl, heterocyclyl, aminoalkyl, aryl, alkaryl, arylalkyl, carboxyalkyl, alkoxycarbonyl, acyl or aminocarbonyl;

each of $K^1$-$K^{52}$ is independently H, halo, alkyl, halogenated alkyl, heteroalkyl, alkenyl, alkynyl, aryl, aralkyl, alkaryl, heterocyclyl, cycloalkyl, cycloalkenyl, cycloalkynyl, hydroxyalkyl, aminoalkyl, amino, alkylamino, arylamino, dialkylamino, alkylarylamino, diarylamino, acylamino, hydroxy, thio, thioalkyl, alkoxy, alkylthio, alkoxyalkyl, aryloxy, arylalkoxy, acyloxy, cyano, nitro, sulfhydryl, carbamoyl, trifluoromethyl, phenoxy, benzyloxy, sulfonyl, phosphonyl, sulfonate ester, phosphate ester, —C(=O)—P$^1$ or —C(=O)—Z—P$^2$;

each of P$^1$ and P$^2$ is independently hydrogen, halo, alkoxy, hydroxy, thio, alkyl, alkenyl, alkynyl, cycloalkyl, cycloalkenyl, cycloalkynyl, aryl, alkaryl, arylalkyl, carbamate, amino, alkylamino, arylamino, dialkylamino, alkylarylamino, diarylamino, alkylthio, heteroalkyl, or heterocyclyl having from 3 to 7 ring atoms; and Z is alkylene, alkenylene, alkynylene, arylene, aralkylene or alkarylene; and Q is substituted or unsubstituted phenyl having formula (VIIa):

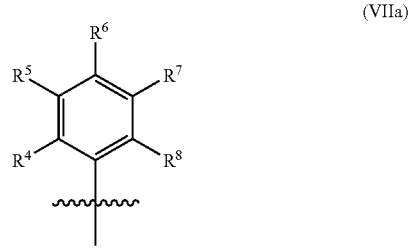

(VIIa)

wherein each of R$^4$, R$^5$, R$^6$, R$^7$ and R$^8$ is independently H, alkyl, alkenyl, alkynyl, heteroalkyl, cycloalkyl, cycloalkenyl, cycloalkynyl, aryl, alkylaryl, arylalkyl, heterocyclyl, hydroxy, alkoxy, alkoxyalkyl, alkoxyalkoxy, acyl, alkylcarbonylalkyl, halogentaed alkylcarbonylalkyl such as trifluoromethylcarbonylalkyl, aminoalkyl, carboxyalkyl, alkoxycarbonyl, alkoxycarbonylalkyl, aminocarbonyl, or NR$^9$R$^{10}$ or R$^4$ and R$^5$ together, R$^5$ and R$^6$ together, R$^6$ and R$^7$ together or R$^7$ and R$^8$ together forming a 5- or 6-membered cycloalkyl, heterocyclyl, aryl or heteroaryl ring fused with the phenyl ring of formula (VIIa); and each of R$^9$ and R$^{10}$ is independently H, alkyl, alkenyl, alkynyl, alkoxyalkyl, alkanoyl, alkenoyl, alkynoyl, cycloalkyl, cycloalkenyl, cycloalkynyl, aryl, alkaryl, arylalkyl, aryloyl, or polyether;

with the proviso that when L has formula (II) where Y is NR$^2$R$^3$, then R$^6$ of Q is hydroxy, alkenyl, alkynyl, heteroalkyl, cycloalkyl, cycloalkenyl, cycloalkynyl, aryl, heterocyclyl, alkoxyalkyl, alkoxyalkoxy, acyl, alkylcarbonylalkyl, halogentaed alkylcarbonylalkyl such as trifluoromethylcarbonylalkyl, carboxyalkyl, alkoxycarbonyl, alkoxycarbonylalkyl, aminocarbonyl or NR$^9$R$^{10}$ or R$^4$ and R$^5$ together, R$^5$ and R$^6$ together, R$^6$ and R$^7$ together or R$^7$ and R$^8$ together form a 5- or 6-membered cycloalkyl, heterocyclyl, aryl or heteroaryl ring fused with the phenyl ring of formula (VIIa).

In some embodiments, each of R, R', R", R$^a$ and R$^b$ independently has formula (VII):

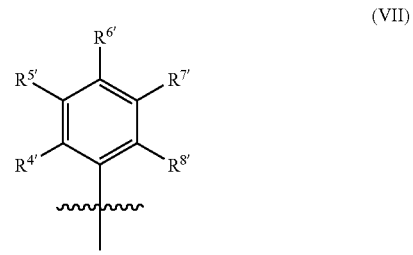

(VII)

wherein each of R$^{4'}$, R$^{5'}$, R$^{6'}$, R$^{7'}$ and R$^{8'}$ is independently H, alkyl, alkenyl, alkynyl, heteroalkyl, cycloalkyl, cycloalkenyl, cycloalkynyl, aryl, alkylaryl, arylalkyl, heterocyclyl, hydroxy, alkoxy, alkoxyalkyl, alkoxyalkoxy, acyl, alkylcarbonylalkyl, halogentaed alkylcarbonylalkyl, aminoalkyl, carboxyalkyl, alkoxycarbonyl, alkoxycarbonylalkyl, aminocarbonyl, or NR$^9$R$^{10}$, or R$^{4'}$ and R$^{5'}$ together, R$^{5'}$ and R$^{6'}$ together, R$^{6'}$ and R$^{7'}$ together or R$^{7'}$ and R$^{8'}$ together forming a 5- or 6-membered cycloalkyl, heterocyclyl, aryl or heteroaryl ring fused with the phenyl ring of formula (VII).

In certain embodiments, R$^{4'}$, R$^{5'}$, R$^{6'}$ and R$^{7'}$ of formula (VII) is independently H; and R$^{8'}$ is —COOH, —COR$^{17}$, —COOR$^{18}$, or —CONR$^{19}$R$^{20}$, wherein R$^{17}$, R$^{18}$, R$^{19}$ and R$^{20}$ is independently H, alkyl, alkenyl, alkynyl, heteroalkyl, cycloalkyl, cycloalkenyl, cycloalkynyl, aryl, alkylaryl, arylalkyl, heterocyclyl, hydroxy, alkoxy, alkoxyalkyl, alkoxyalkoxy, acyl, alkylcarbonylalkyl, halogentaed alkylcarbonylalkyl, aminoalkyl, carboxyalkyl, alkoxycarbonyl, alkoxycarbonylalkyl, aminocarbonyl, or N, R$^{19}$ and R$^{20}$ together forming a 5-or 6-membered heterocycle having at least a nitrogen atom. In other embodiments, R$^{8'}$ is —CONR$^{19}$R$^{20}$ and N, R$^{19}$ and R$^{20}$ together form a 5- or 6-saturated heterocycle. In further embodiments, the heterocycle is substituted or unsubstituted piperidine, morpholine, pyrrolidine, oxazolidine, thiomorpholine, thiazolidine or piperazine.

In some embodiments, each of R$^{4'}$, R$^{5'}$, R$^{6'}$ and R$^{7'}$ of formula (VII) is independently H; and R$^{8'}$ is methyl, methoxy, or the like to make the benzene ring out of the xanthenes ring plane.

In some embodiments, L has formula (II) or a tautomer thereof. In other embodiments, Y of formula (II) is NR$^2$R$^3$. In other embodiments, Y of formula (II) is OH, OAc or OCH$_2$OCOCH$_3$. In further embodiments, each of K$^1$, K$^3$, K$^4$, K$^6$, K$^7$, K$^8$, K$^9$ and K$^{10}$ is H; and each of K$^2$ and K$^5$ is independently H or halo. In still further embodiments, each of K$^1$, K$^2$, K$^3$, K$^4$, K$^5$, K$^6$, K$^7$, K$^8$, K$^9$ and K$^{10}$ is H.

In certain embodiments, L has formula (III) or a tautomer thereof. In other embodiments, each of K$^{11}$, K$^{12}$, K$^{13}$, K$^{14}$, K$^{16}$ and K$^{17}$ is H; and K is H or halo.

In some embodiments, L has formula (IV) or (IVa). In other embodiments, each of K$^{18}$ and K$^{20}$ is H; and K$^{19}$ is H or halo.

In certain embodiments, L has formula (V). In other embodiments, V is N. In other embodiments, V is CR". In further embodiments, Y$^1$ is N$^+$R$^2$R$^{3'}$. In still further embodiments, Y$^1$ is O. In still further embodiments, each of K$^{21}$, K$^{22}$, K$^{23}$, K$^{24}$, K$^{25}$ and K$^{26}$ is H.

In some embodiments, L has formula (VI). In other embodiments, Y$^2$ is N$^+$R$^2$R$^{3'}$. In further embodiments, Y$^2$ is O. In still further embodiments, each of K$^{27}$-K$^{36}$ is H.

In some embodiments, L has formula (XX). In other embodiments, Y$^3$ is N$^+$R$^2$R$^{3'}$. In further embodiments, Y$^3$ is O. In still further embodiments, each of $K^{37}$-$K^{44}$ is H. In still further embodiments, each of $K^{38}$-$K^{44}$ is H; and $K^{37}$ is Cl or F.

In some embodiments, L has formula (XXI). In other embodiments, $Y^4$ is $N^+R^{2'}R^{3'}$. In further embodiments, $Y^4$ is O. In still further embodiments, each of $K^{46}$-$K^{51}$ is H, and at least one of $K^{45}$ and $K^{52}$ is independently Cl or F.

In certain embodiments, $R^6$ of formula (VIa) is —$OCH_2OCH_3$, OH, $NR^9R^{10}$, —$CH_2CH_2C(=O)CF_3$, or —$CH_2CH_2C(=O)OCH_3$, wherein each of $R^9$ and $R^{10}$ is independently H or alkyl; and each of $R^4$, $R^5$, $R^7$ and $R^8$ is H. In other embodiments, $R^6$ is OH, $NH_2$ or —$CH_2CH_2C(=O)CF_3$.

In some embodiments, $R^1$ of formula (I) is H, alkyl, halogenated alkyl, heteroalkyl, alkenyl, alkynyl, aryl, aralkyl, alkaryl, heterocyclyl, cycloalkyl, cycloalkenyl, and cycloalkynyl; each of $R^4$, $R^5$, $R^6$, $R^7$ and $R^8$ is independently H, halogen, alkyl, alkoxy, or polyether; $R^6$ is $OR^{11}$ or $CH_2CH_2COR^{12}$, where $R^{11}$ is H, alkyl, alkoxyalkyl, alkanoyl, or polyether; $R^{12}$ is an electron-withdrawing group selected from $CF_3$, halogen-substituted lower alkyl, or $(C=O)$—O—$V^2$; and $V^2$ is a group selected from alkyl, alkenyl, alkynyl, cycloalkyl, cycloalkenyl, cycloalkynyl, aryl, alkaryl or arylalkyl.

Provided also herein are fluorogenic probe compositions for measuring, detecting or screening peroxynitrite comprising the aromatic amine compound disclosed herein. In certain embodiments, the aromatic amine compound is Compound (10), Compound (12), Compound (12a), Compound (22), or Compound (30):

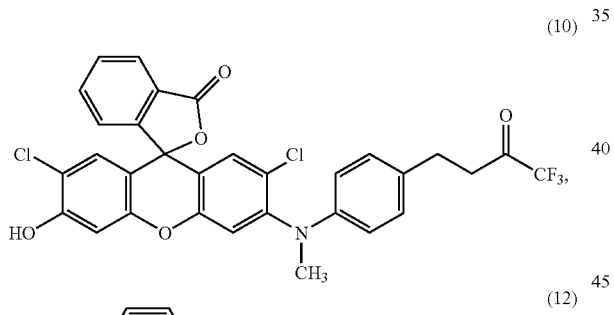

(10)

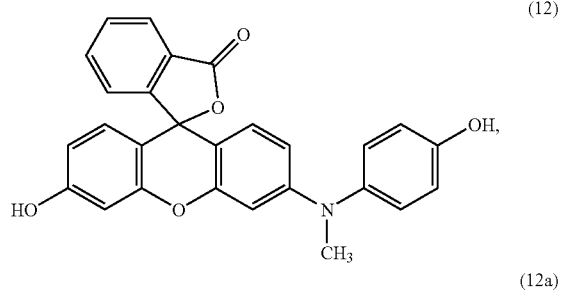

(12)

(12a)

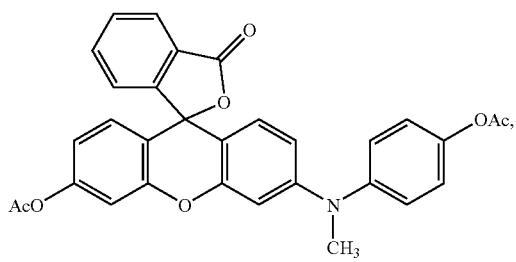

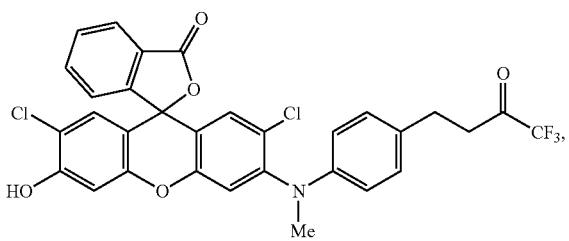

(22)

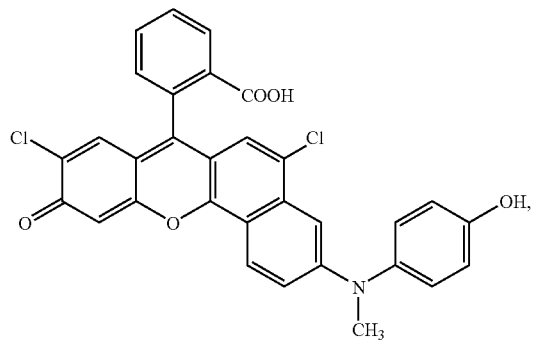

(30)

or a tautomer thereof, or a combination thereof.

Provided also herein are fluorogenic probe compositions for measuring, detecting or screening hypochlorite comprising the aromatic amine compound disclosed herein. In certain embodiments, the aromatic amine compound is Compound (14):

(14)

or a tautomer thereof.

In certain embodiments, the fluorogenic probe compositions disclosed herein further comprise a solvent, an acid, a base, a buffer solution or a combination thereof.

Provided also herein are fluorogenic probe compositions for measuring peroxynitrite or hypochlorite in a sample, wherein the compositions comprise the aromatic amine compounds disclosed herein. In some embodiments, the fluorogenic probe compositions further comprise a solvent, an acid, a base, a buffer solution or a combination thereof.

Provided also herein are methods for measuring peroxynitrite or hypochlorite in a sample, wherein the methods comprise the steps of:

a) contacting an aromatic amine compound disclosed herein with the sample to form a fluorescent compound; and b) measuring fluorescence properties of the fluorescent compound to determine the amount of peroxynitrite or hypochlorite in the sample.

In some embodiments, the sample is a chemical sample or biological sample. In other embodiments, the sample is a biological sample comprising a microorganism, or a cell or tissue from animals.

Provided also herein are high-throughput screening fluorescent methods for detecting peroxynitrite or hypochlorite in samples, wherein the high-throughput methods comprise the steps of:

a) contacting an aromatic amine compound disclosed herein with the samples to form one or more fluorescent compounds; and b) measuring fluorescence properties of the fluorescent compounds to determine the amount of peroxynitrite or hypochlorite in the samples.

Provided also herein are high-throughput methods for screening one or more target compounds that can increase or decrease the level of peroxynitrite or hypochlorite, wherein the high-throughput methods comprise the steps of:

a) contacting an aromatic amine compound disclosed herein with the target compounds to form one or more fluorescent compounds; and b) measuring fluorescence properties of the fluorescent compounds to determine the target compounds qualitatively or quantitatively.

DEFINITIONS

Figure 1:
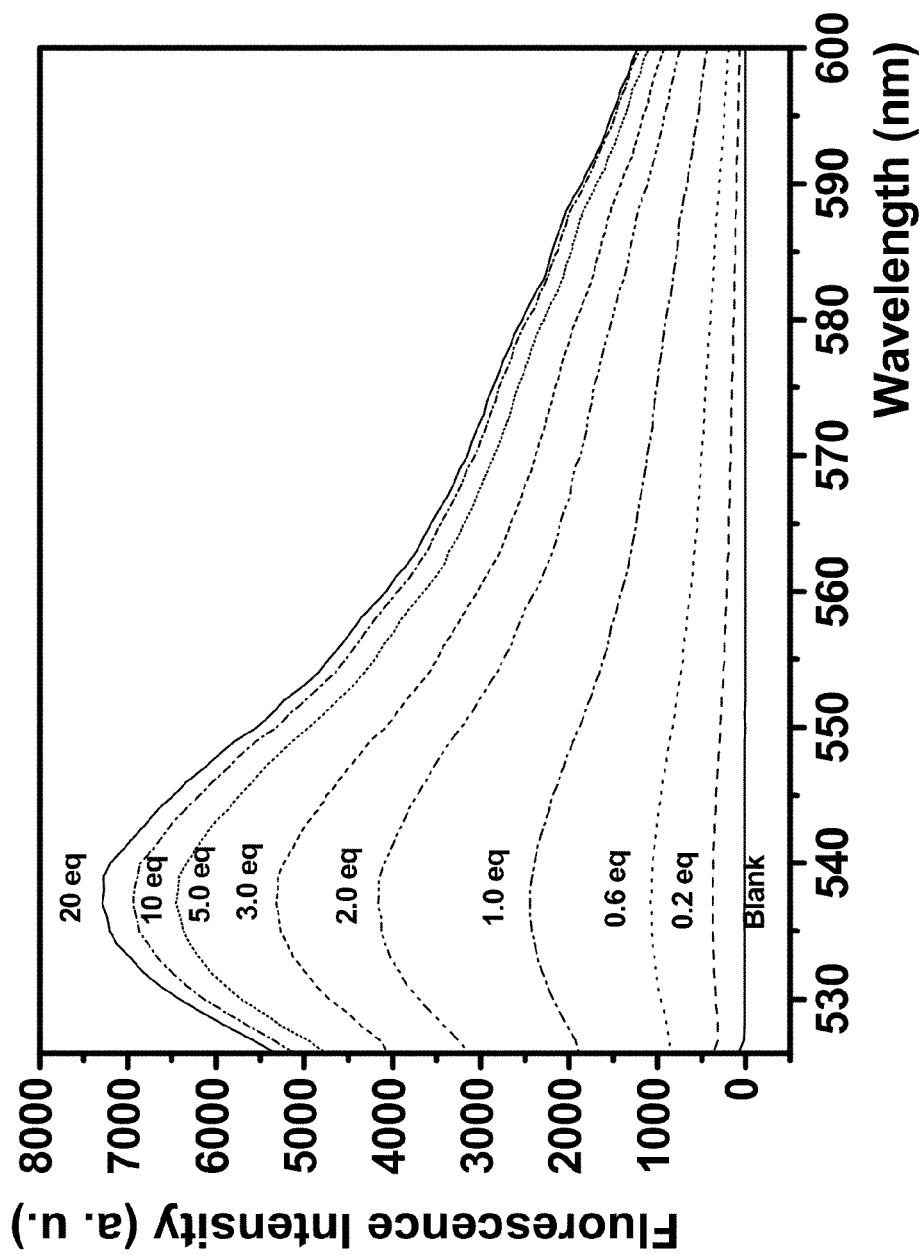
FIG. 1 depicts fluorescence spectra showing fluorescence intensities of 10 μM of Compound 10 in response to different concentrations of $ONOO^-$ at different wavelengths. The spectra were acquired in 0.1 M potassium phosphate buffer at pH 7.4 where 0.1% DMF was used as a cosolvent and λex was at 520 nm.

To facilitate the understanding of the subject matter disclosed herein, a number of terms, abbreviations or other shorthand as used herein are defined below. Any term, abbreviation or shorthand not defined is understood to have the ordinary meaning used by a skilled artisan contemporaneous with the submission of this application.

"Amino" refers to a primary, secondary, or tertiary amine which may be optionally substituted. Specifically included are secondary or tertiary amine nitrogen atoms which are members of a heterocyclic ring. Also specifically included, for example, are secondary or tertiary amino groups substituted by an acyl moiety. Some non-limiting examples of amino group include —NR'R" wherein each of R' and R" is independently H, alkyl, aryl, aralkyl, alkaryl, cycloalkyl, acyl, heteroalkyl, heteroaryl or heterocycyl.

"Alkyl" refers to a fully saturated acyclic monovalent radical containing carbon and hydrogen, and which may be branched or a straight chain. In some embodiments, alkyl contains from about 1 to about 25 carbon atoms. Examples of alkyl groups are methyl, ethyl, n-propyl, isopropyl, n-butyl, t-butyl, n-heptyl, n-hexyl, n-octyl, and n-decyl. "Lower alkyl" refers to an alkyl radical of one to six carbon atoms, as exemplified by methyl, ethyl, n-butyl, i-butyl, t-butyl, isoamyl, n-pentyl, and isopentyl.

"Heteroalkyl" refers to an alkyl group having one or more of the carbon atoms within the alkyl group substituted by a heteroatom such as O, S and N. In some embodiments, the heteroalkyl group comprises one or more O atoms. In other embodiments, the heteroalkyl group comprises one or more S atoms. In further embodiments, the heteroalkyl group comprises one or more aminylene groups. In certain embodiments, the heteroalkyl group comprises two or more O, S, aminylene or a combination thereof.

"Alkenyl" or "alkenylene" respectively refers to a monovalent or divalent hydrocarbyl radical which has at least one double bond. The alkenyl or alkenylene group may be cyclic, branched acyclic or straight acyclic. In some embodiments, the alkenyl or alkenylene group contains only one double bond. In other embodiments, the alkenyl or alkenylene group contains two or more double bonds. In further embodiments, the alkenyl or alkenylene group can be a lower alkenyl or alkenylene containing from two to eight carbon atoms in the principal chain. In further embodiments, the alkenyl or alkenylene group can have one double bond and up to 25 carbon atoms, as exemplified by ethenyl, propenyl, isopropenyl, butenyl, isobutenyl, hexenyl, and the like.

"Alkynyl" or "alkynylene" respectively refers to a monovalent or divalent hydrocarbyl radical which has at least a triple bond. In some embodiments, the alkynyl or alkynylene group contains only one triple bond. In other embodiments, the alkynyl or alkynylene group contains two or more triple bonds. In further embodiments, the alkynyl or alkynylene group can be a lower alkynyl or alkynylene containing from two to eight carbon atoms in the principal chain. In further embodiments, the alkynyl or alkynylene group can have one triple bond and up to 20 carbon atoms, as exemplified by ethynyl, propynyl, isopropynyl, butynyl, isobutynyl, hexynyl, and the like.

"Aromatic" or "aromatic group" refers to aryl or heteroaryl.

"Aryl" refers to optionally substituted carbocyclic aromatic groups. In some embodiments, the aryl group includes a monocyclic or bicyclic group containing from 6 to 12 carbon atoms in the ring portion, such as phenyl, biphenyl, naphthyl, substituted phenyl, substituted biphenyl or substituted naphthyl. In other embodiments, the aryl group is phenyl or substituted phenyl.

"Aralkyl" refers to an alkyl group which is substituted with an aryl group. Some non-limiting examples of aralkyl include benzyl and phenethyl.

"Alkaryl" refers to an aryl group which is substituted with an alkyl group. Some non-limiting examples of alkaryl include methylphenyl and methylnaphthyl.

"Acyl" refers to a monovalent group of the formula —C(=O)H, —C(=O)-alkyl, —C(=O)-aryl, —C(=O)-aralkyl, or —C(=O)-alkaryl.

"Halogen" refers to fluorine, chlorine, bromine and iodine.

"Halo" refers to fluoro, chloro, bromo and iodo.

"Heteroatom" refers to atoms other than carbon and hydrogen.

"Heterocyclo" or "heterocyclyl" refers to optionally substituted, fully saturated or unsaturated, monocyclic or bicyclic, aromatic or nonaromatic groups having at least one heteroatom, such as O, S, N, B and P, in at least one ring. The aromatic heterocyclyl (i.e., heteroaryl) group can have 1 or 2 oxygen atoms, 1 or 2 sulfur atoms, and/or 1 to 4 nitrogen atoms in the ring, and may be bonded to the remainder of the molecule through a carbon or heteroatom. Some non-limiting examples of heteroaryl include furyl, thienyl, thiazolyl, pyridyl, oxazolyl, pyrrolyl, indolyl, quinolinyl, or isoquinolinyl and the like.

"Hydrocarbon" or "hydrocarbyl" refers to organic compounds or radicals consisting exclusively of the elements carbon and hydrogen. Hydrocarbyl includes alkyl, alkenyl, alkynyl, and aryl moieties. Hydrocarbyl also includes alkyl, alkenyl, alkynyl, and aryl moieties substituted with other aliphatic, cyclic or aryl hydrocarbon groups, such as alkaryl, alkenaryl and alkynaryl. In some embodiments, "hydrocarbon" or "hydrocarbyl" comprises 1 to 30 carbon atoms.

"Hydrocarbylene" refers to a divalent group formed by removing two hydrogen atoms from a hydrocarbon, the free valencies of which are not engaged in a double bond, e.g. arylene, alkylene, alkenylene, alkynylene, aralkylene or alkarylene.

"Substituted" as used herein to describe a compound or chemical moiety refers to that at least one hydrogen atom of that compound or chemical moiety is replaced with a second chemical moiety. Non-limiting examples of substituents are those found in the exemplary compounds and embodiments disclosed herein, as well as halogen; alkyl; heteroalkyl; alkenyl; alkynyl; aryl, heteroaryl, hydroxy; alkoxyl; amino; nitro; thiol; thioether; imine; cyano; amido; phosphonato; phosphine; carboxyl; thiocarbonyl; sulfonyl; sulfonamide; ketone; aldehyde; ester; oxo; haloalkyl (e.g., trifluoromethyl); carbocyclic cycloalkyl, which can be monocyclic or fused or non-fused polycyclic (e.g., cyclopropyl, cyclobutyl, cyclopentyl or cyclohexyl) or a heterocycloalkyl, which can be monocyclic or fused or non-fused polycyclic (e.g., pyrrolidinyl, piperidinyl, piperazinyl, morpholinyl or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl or benzofuranyl); amino (primary, secondary or tertiary); o-lower alkyl; o-aryl, aryl; aryl-lower alkyl; —$CO_2CH_3$; —$CONH_2$; —$OCH_2CONH_2$; —$NH_2$; —$SO_2NH_2$; —$OCHF_2$; —$CF_3$; —$OCF_3$; —NH(alkyl); —N(alkyl)$_2$; —NH(aryl); —N(alkyl)(aryl); —N(aryl)$_2$; —CHO; —CO(alkyl); —CO(aryl); —$CO_2$(alkyl); and —$CO_2$(aryl); and such moieties can also be optionally substituted by a fused-ring structure or bridge, for example —$OCH_2O$—. These substituents can optionally be further substituted with a substituent selected from such groups. All chemical groups disclosed herein can be substituted, unless it is specified otherwise. For example, "substituted" alkyl, alkenyl, alkynyl, aryl, hydrocarbyl or heterocyclo moieties described herein are moieties which are substituted with a hydrocarbyl moiety, a substituted hydrocarbyl moiety, a heteroatom, or a heterocyclo. Further, substituents may include moieties in which a carbon atom is substituted with a heteroatom such as nitrogen, oxygen, silicon, phosphorus, boron, sulfur, or a halogen atom. These substituents may include halogen, heterocyclo, alkoxy, alkenoxy, alkynoxy, aryloxy, hydroxy, protected hydroxy, keto, acyl, acyloxy, nitro, amino, amido, cyano, thiol, ketals, acetals, esters and ethers.

"Luminescence" refers to the emission of light that does not derive energy from the temperature of the emitting body. Luminescence may be caused by chemical, biochemical, or crystallographic changes, the motions of subatomic particles, or radiation-induced excitation of an atomic system. Luminescence includes, but is not limited to, phosphorescence, fluorescence, chemoluminescence, bioluminescence, crystalloluminescence, electroluminescence such as cathodoluminescence, mechanoluminescence, such as sonoluminescence, triboluminescence, fractoluminescence and piezoluminescence, photoluminescence such as phosphorescence and fluorescence, radioluminescence, and thermoluminescence.

"Luminophore" refers to an atom or a chemical group in a chemical compound that manifests luminescence. There are organic and inorganic luminophores. In some embodiments, the luminophores disclosed herein are organic luminophores such as rhodol, rhodamine, resorufin or a derivative thereof. Luminophores includes, but is not limited to, phosphores, fluorophores, chemolumiphores, biolumiphores, crystallolumiphores, electrolumiphores such as cathodolumiphores, mechanolumiphores, such as sonolumiphores, tribolumiphores, fractolumiphores and piezolumiphores, photolumiphores, radiolumiphores, and thermolumiphores.

"Photoluminescence" refers to a process in which a substance absorbs photons (electromagnetic radiation) and then radiates photons back out. The substance after absorbing the photons is excited to a higher energy state and then returns to a lower energy state accompanied by the emission of a photon. Two common types of photoluminescence include phosphorescence and fluorescence.

"Luminescence Quencher" refers to a compound that can eliminate, partially or totally, the luminescence of a luminophore.

"Fluorescence" refers to a luminescence where the molecular absorption of a photon triggers the emission of another photon with a longer wavelength. In some embodiments, the absorbed photon is in the ultraviolet range, and the emitted light is in the visible range.

"Fluorophore" refers to a small molecule or a part of a large molecule, that can be excited by light to emit fluorescence. In some embodiments, fluorophores efficiently produce fluorescence upon excitation with light which has a wavelength from about 200 nanometers to about 1000 nanometers, or from about 500 nanometers to about 800 nanometers. The intensity and wavelength of the emitted radiation generally depend on both the fluorophore and the chemical environment of the fluorophore. A fluorophore may be selected from acridine orange, anthracene ring, allophycocyanin, BODIPY, cyanines, coumarin, Edans, Eosin, Erythrosin, fluorescamine, fluorescein, FAM (carboxyfluorescein), HEX (hexachlorofluorescein), JOE (6-carboxy-4',5'-dichloro-2',7'-dimethoxyfluorescein), Oregon Green, phycocyanin, phycoerythrin, rhodamine, ROX (Carboxy-X-rhodamine), TAMRA (carboxytetramethylrhodamine), TET (tetrachloro-fluorescein), Texas red, tetramethylrhodamine, and xanthines. Other non-limiting examples can be found in *The Handbook: a Guide to Fluorescent Probes and Labeling Technologies* (10th Edition, Molecular Probes, Eugene, Oreg., 2006), which are incorporated herein by reference.

"Phosphorescence" refers to a specific type of photoluminescence related to fluorescence. Unlike fluorescence, a phosphorescent material does not immediately re-emit the radiation it absorbs. The slower time scales of the re-emission are associated with "forbidden" energy state transitions in quantum mechanics. As these transitions occur less often in certain materials, absorbed radiation may be re-emitted at a lower intensity for up to several hours in some embodiments.

"Chemiluminescence" or "chemoluminescence" refers to the effect of luminescence as the result of a chemical reaction.

"Bioluminescence" refers to the production and emission of light by a living organism as the result of a chemical reaction during which chemical energy is converted to light energy.

"Crystalloluminescence" refers to the effect of luminescence produced during crystallization.

"Electroluminescence" refers to the effect of luminescence where a material emits light in response to an electric current passed through it, or to a strong electric field.

"Cathodoluminescence" refers to the effect of luminescence whereby a beam of electrons is generated by an electron gun (e.g. cathode ray tube) and then impacts on a luminescent material such as a phosphor, causing the material to emit visible light.

"Mechanoluminescence" refers to the effect of luminescence as the result of any mechanical action on a solid. It can be produced through friction, ultrasound or other means.

"Triboluminescence" refers to the effect of luminescence in which light is generated via the breaking of asymmetrical bonds in a crystal when that material is scratched, crushed, or rubbed.

"Fractoluminescence" refers to the emission of light from the fracture of a crystal.

"Piezoluminescence" refers to the effect of luminescence caused by pressure that results only in elastic deformation.

"Radioluminescence" refers to the effect of luminescence produced in a material by the bombardment of ionizing radiation such as beta particles.

"Thermoluminescence" refers to the effect of luminescence where some mineral substances store energy when exposed to ultraviolet or other ionising radiation. This energy is released in the form of light when the mineral is heated.

"Reactive group" or "Rg" refers to a group that is highly reactive toward an amine, a thio, an alcohol, an aldehyde or a ketone. Some non-limiting examples of reactive group include phosphoramidite, succinimidyl ester of a carboxylic acid, haloacetamide, hydrazine, isothiocyanate, maleimide, perfluorobenzamido, azidoperfluorobenzamido and so on.

"Conjugated substance" or "Cg" refers to a desired substance which needs to be conjugated and generally possess a suitable functional group for covalent reaction with a respective reactive group, Rg. Some non-limiting examples of conjugated substances include conjugates of antigens, steroids, vitamins, drugs, haptens, metabolites, toxins, amino acids, peptides, nucleotides, oligonucleotides, nucleic acid, carbohydrates, lipids, and the like.

"Reactive oxygen species" or ROS refer to oxygen-containing ions, free radicals as well as non-radical species. Some non-limiting examples of reactive oxygen species include $^1O_2$, $O_2^{\cdot-}$, $ROO^{\cdot}$, $^{\cdot}OH$, $OCl^-$, and $H_2O_2$.

"Reactive nitrogen species" or RNS refer to nitrogen-containing ions, free radicals as well as non-radical species. Some non-limiting examples of reactive nitrogen species include nitric oxide ($NO^{\cdot}$), nitrogen dioxide ($NO_2^{\cdot}$), nitrite ($NO_2^-$), and peroxynitrite (ONOO).

"Fluorogenic probe" refers to a latent fluorescent molecule, whose fluorescence stays in "off" state before reacting with the target and may switch to "on" state after reacting with the target. In some embodiments, the fluorogenic probes disclosed herein do not react substantially with reactive oxygen species and reactive nitrogen species. In other embodiments, the fluorogenic probes disclosed herein may react substantially with reactive oxygen species and reactive nitrogen species.

"Peroxynitrite probe" refers to a compound that can react with peroxynitrite to form a fluorescent compound. In some embodiments, the peroxynitrite probes disclosed herein do not react substantially with peroxynitrite. In other embodiments, the peroxynitrite probes disclosed herein may react substantially with peroxynitrite.

"Hypochlorite probe" refers to a compound that can react with hypochlorite to form a fluorescent compound. In some embodiments, the hypochlorite probes disclosed herein do not react substantially with hypochlorite. In other embodiments, the hypochlorite probes disclosed herein may react substantially with hypochlorite.

"Quinone" refers to a compound comprising a cyclohexadienedione moiety. Some non-limiting examples of quinones include 1,4-benzoquinone, 1,2-benzoquinone, 1,4-naphthoquinone, anthraquinone, phenanthraquinone, and the like.

"Reacting", "adding" or the like refers to contacting one reactant, reagent, solvent, catalyst, reactive group or the like with another reactant, reagent, solvent, catalyst, reactive group or the like. Reactants, reagents, solvents, catalysts, reactive group or the like can be added individually, simultaneously or separately and can be added in any order. They can be added in the presence or absence of heat and can optionally be added under an inert atmosphere. In some embodiments, "reacting" refers to in situ formation or intra-molecular reaction where the reactive groups are in the same molecule.

"Substantially react" refers to that at least a reactant of a reaction is consumed by an amount of more than about 75% by mole, by more than about 80% by mole, by more than about 85% by mole, or by more than about 90% by mole. In some embodiments, "substantially react" refers to that the reactant is consumed by more than about 95% by mole. In other embodiments, "substantially react" refers to that the reactant is consumed by more than about 97% by mole. In further embodiments, "substantially react" refers to that the reactant is consumed by more than about 99% by mole.

"High-throughput method" refers to a method that can autonomously process or evaluate a large number of samples. In some embodiments, informatics systems can be used and implemented in the high-throughput method. The informatics systems can provide the software control of the physical devices used in the high-throughput method, as well as organize and store electronic data generated by the high-throughput method.

DETAILED DESCRIPTION

Provided herein are aromatic amine compounds that can be used as luminescence quenchers and/or fluorogenic probes for measuring, detecting or screening reactive nitrogen species (RNS) such as peroxynitrite or reactive oxygen species (ROS) such as hypochlorite. In some embodiments, the aromatic amine compounds disclosed herein can be used as luminescence quenchers. In other embodiments, the aromatic amine compounds disclosed herein can be used to detect, measure or screen peroxynitrite or hypochlorite selectively and specifically. In further embodiments, the aromatic amine compounds disclosed herein can be used to selectively react with peroxynitrite or hypochlorite in the presence of other reactive oxygen and/or nitrogen species such as $^1O_2$, $O_2^{\cdot -}$, NO, $H_2O_2$, .OH, $^-OCl$, $ONOO^-$ and alkylperoxyl radical (ROO$^{\cdot}$).

The aromatic amine compounds disclosed herein generally can be represented by formula (I):

(I)

wherein L is a luminophore; Q is a luminescence quenching moiety; and $R^1$ is H, alkyl, halogenated alkyl, alkenyl, alkynyl, alkoxyalkyl, heteroalkyl, cycloalkyl, cycloalkenyl, cycloalkynyl, heterocyclyl, aminoalkyl, aryl, alkaryl, arylalkyl, alkyloxy, carboxyalkyl, alkylamino, alkoxyamino, alkylamido, alkoxyamido, sulfonylaryl or acyl. In some embodiments, both $R^1$ and Q are luminescence quenching moieties. In other embodiments, $R^1$ and Q are the same. In further embodiments, $R^1$ and Q are different.

In some embodiments, N, Q and $R^1$ together form a 4-, 5-, 6-, 7- or 8-membered saturated heterocycle containing at least a nitrogen. In other embodiments, N, Q and $R^1$ together form a 5- or 6- membered saturated heterocycle containing at least a nitrogen. In further embodiments, N, Q and $R^1$ together form a 5- or 6-saturated heterocycle selected from substituted or unsubstituted piperidine, morpholine, pyrrolidine, oxazolidine, thiomorpholine, thiazolidine or piperazine.

Any luminophore that has luminescence properties can be used herein. In certain embodiments, the luminophore L is a phosphore, fluorophore, chemolumiphore, biolumiphore, crystallolumiphore, electrolumiphore, mechanolumiphore, photolumiphore, radiolumiphore or thermolumiphore. In other embodiments, the luminophore L is a phosphore, fluorophore or chemolumiphore.

In some embodiments, the luminophore L is a fluorophore group. Some non-limiting examples of suitable fluorophore groups include monovalent fluorescent groups derived by removing one atom or group, such as H, OH or amino group, from substituted or unsubstituted fluorescein, BODIPY (boron dipyrrimethene), porphyrins, sulforhodamines, acridine orange, acridine yellow, auramine O, euxanthin, luciferin, benzanthrone, 9,10-bis(phenylethynyl)anthracene, 5,12-bis(phenylethynyl)naphthacene, calcein, carboxyfluorescein, 1-chloro-9,10-bis(phenylethynyl)anthracene, coumarins such as 7-hydroxycoumarin, cyanine, 4',6-diamidino-2-phenylindole, ethidium bromide, perylene, phycobilins, phycoerythrin, phycoerythrobilin, rhodol, rhodamine, rubrene, stilbene, Texas Red, naphthofluorescein or a derivative thereof. Other non-limiting examples of suitable fluorophore groups can be found in *The Handbook: a Guide to Fluorescent Probes and Labeling Technologies* (10th Edition, Molecular Probes, Eugene, Oreg., 2006), which is incorporated herein by reference.

In certain embodiments, the luminophore L is rhodol, rhodamine, resorufin, fluorescein or a derivative thereof. In other embodiments, L has one of formulae (II)-(VI):

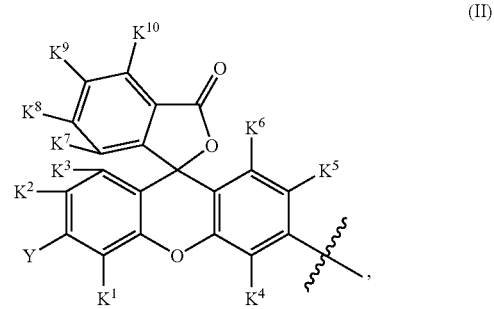
(II)

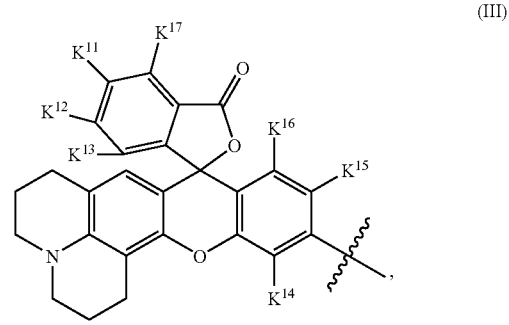
(III)

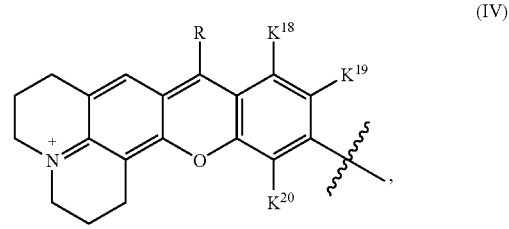
(IV)

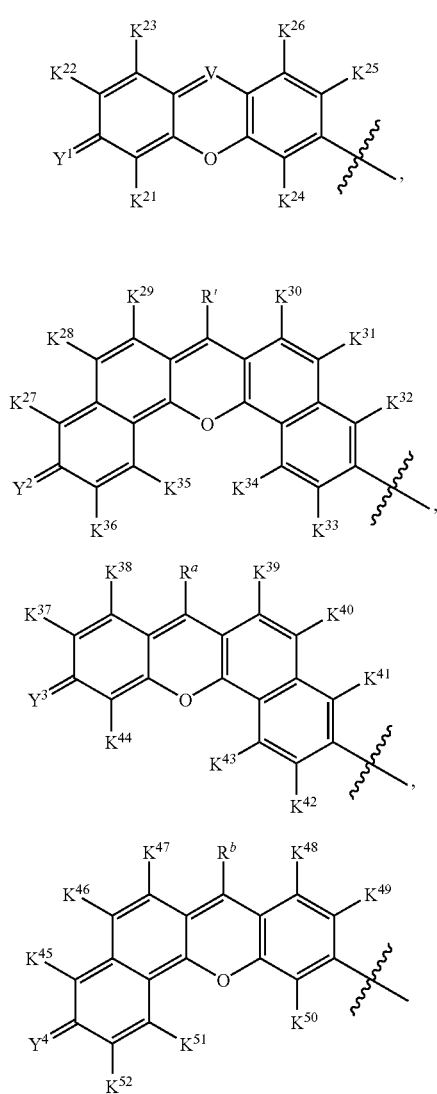

or a tautomer thereof,
wherein Y is O-A, S-A or $NR^2R^3$;
each of $Y^1$, $Y^2$, $Y^3$ and $Y^4$ is independently O, S, $NR^{2'}R^{3'}$ or $N^+R^2R^{3'}$;
V is N or CR";
each of $R^2$, $R^3$, $R^{2'}$ and $R^{3'}$ is independently H, alkyl, halogenated alkyl, alkenyl, alkynyl, alkoxyalkyl, heteroalkyl, cycloalkyl, cycloalkenyl, cycloalkynyl, heterocyclyl, aminoalkyl, aryl, alkaryl, arylalkyl, alkyloxy, carboxyalkyl, alkylamido, alkoxyamido, sulfonylaryl or acyl;
each of R, R', R", $R^a$ and $R^b$ is independently H, CN, alkyl, halogenated alkyl, alkenyl, alkynyl, alkoxyalkyl, heteroalkyl, cycloalkyl, cycloalkenyl, cycloalkynyl, heterocyclyl, aminoalkyl, aryl, alkaryl, arylalkyl, alkyloxy, carboxyalkyl, alkylamino, alkoxyamino, alkylamido, alkoxyamido, sulfonylaryl or acyl;
A is H, alkyl, alkenyl, alkynyl, alkoxyalkyl, heteroalkyl, cycloalkyl, cycloalkenyl, cycloalkynyl, heterocyclyl, aminoalkyl, aryl, alkaryl, arylalkyl, carboxyalkyl, alkoxycarbonyl, acyl or aminocarbonyl;
each of $K^1$-$K^{52}$ is independently H, halo, alkyl, halogenated alkyl, heteroalkyl, alkenyl, alkynyl, aryl, aralkyl, alkaryl, heterocyclyl, cycloalkyl, cycloalkenyl, cycloalkynyl, hydroxyalkyl, aminoalkyl, amino, alkylamino, arylamino, dialkylamino, alkylarylamino, diarylamino, acylamino, hydroxy, thio, thioalkyl, alkoxy, alkylthio, alkoxyalkyl, aryloxy, arylalkoxy, acyloxy, cyano, nitro, sulfhydryl, carbamoyl, trifluoromethyl, phenoxy, benzyloxy, sulfonyl, phosphonyl, sulfonate ester, phosphate ester, —C(=O)—$P^1$ or —C(=O)—Z—$P^2$;
each of $P^1$ and $P^2$ is independently hydrogen, halo, alkoxy, hydroxy, thio, alkyl, alkenyl, alkynyl, cycloalkyl, cycloalkenyl, cycloalkynyl, aryl, alkaryl, arylalkyl, carbamate, amino, alkylamino, arylamino, dialkylamino, alkylarylamino, diarylamino, alkylthio, heteroalkyl, or heterocyclyl having from 3 to 7 ring atoms; and
Z is alkylene, alkenylene, alkynylene, arylene, aralkylene or alkarylene.

In some embodiments, L has formula (II):

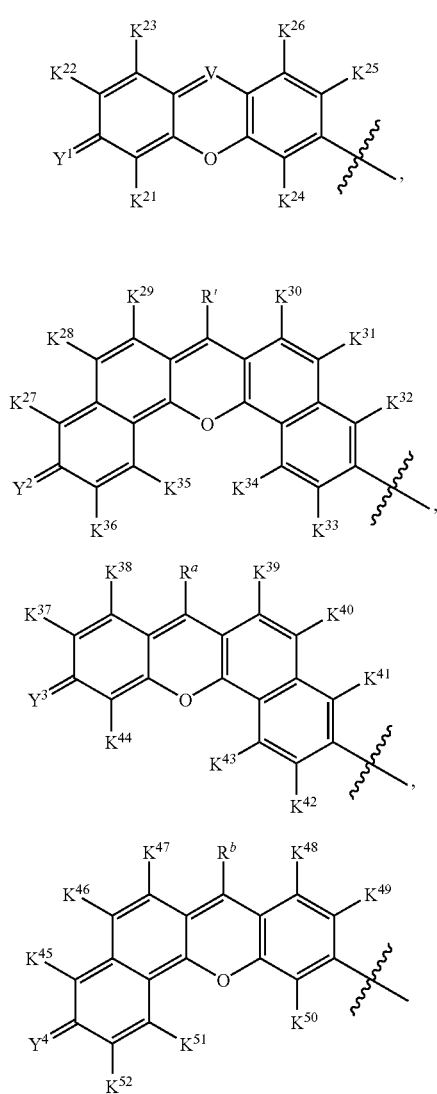

(II)

or a tautomer thereof,
wherein Y and $K^1$-$K^{10}$ are as disclosed herein. In some embodiments, Y is OH, $CH_3C(=O)O$ or $NR^2R^3$; each of $K^1$-$K^{10}$ is independently H, halo, alkyl, halogenated alkyl, heteroalkyl, alkenyl, alkynyl, aryl, aralkyl, alkaryl, heterocyclyl, cycloalkyl, cycloalkenyl, cycloalkynyl, hydroxyalkyl, aminoalkyl, amino, alkylamino, arylamino, dialkylamino, alkylarylamino, diarylamino, acylamino, hydroxy, thio, thioalkyl, alkoxy, alkylthio, alkoxyalkyl, aryloxy, arylalkoxy, acyloxy, cyano, nitro, sulfhydryl, carbamoyl, trifluoromethyl, phenoxy, benzyloxy, sulfonyl, phosphonyl, sulfonate ester, or phosphate ester; and each of $R^2$ and $R^3$ is independently H or alkyl.

In certain embodiments, each of $K^1$, $K^3$, $K^4$, $K^6$, $K^7$, $K^8$, $K^9$ and $K^{10}$ is H; and each of $K^2$ and $K^5$ is independently H or halo. In other embodiments, each of $K^1$-$K^{10}$ is H. In further embodiments, Y is OH or $CH_3C(=O)O$. In still further embodiments, Y is OH or $CH_3C(=O)O$; and each of $K^1$-$K^{10}$ is H. In still further embodiments, Y is OH or $CH_3C(=O)O$; each of $K^1$, $K^3$, $K^4$, $K^6$, $K^7$, $K^8$, $K^9$ and $K^{10}$ is H; and each of $K^2$ and $K^5$ is independently H or halo.

In some embodiments, Y is $NR^2R^3$. In other embodiments, $R^2$ together with $K^2$ or $R^3$ together with $K^3$ form a part of a 5- or 6-membered saturated or unsaturated ring wherein the ring is optionally substituted. In other embodiments, $R^2$, $R^3$, $K^1$ and $K^2$ together form a part of a saturated or unsaturated bicyclic ring wherein the bicyclic ring is substituted or unsubstituted.

In certain embodiments, the tautomer of formula (II) has formula (IIa):

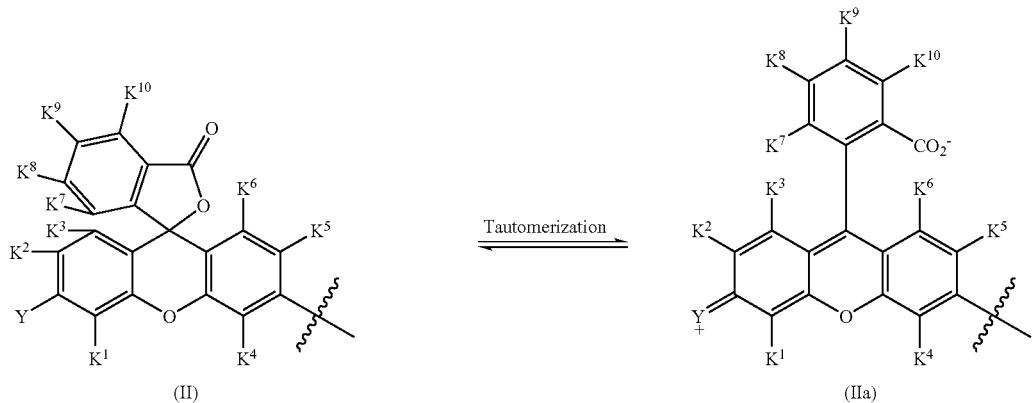

(II)    (IIa)

wherein Y and $K^1$-$K^{10}$ are as disclosed herein. In some embodiments, Y of formula (IIa) is $NR^2R^3$.

In other embodiments, the tautomer of formula (II) has formula (IIb):

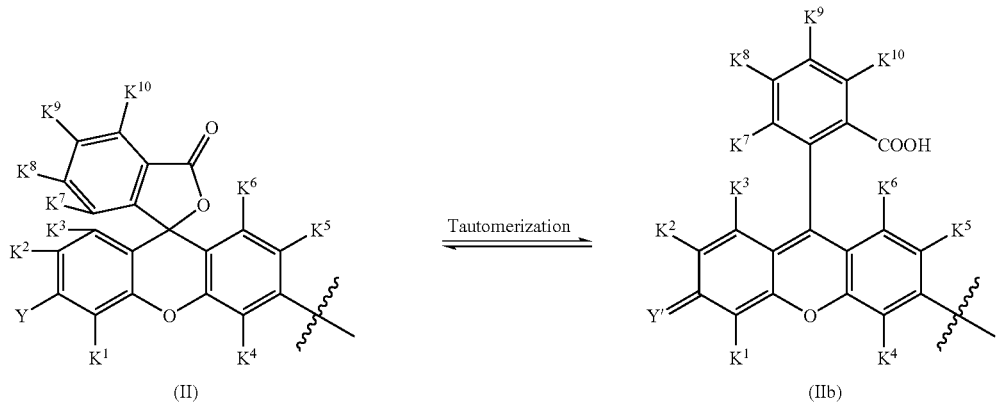

(II)    (IIb)

wherein Y is OH, SH or $NHR^2$; $R^2$ and $K^1$-$K^{10}$ are as disclosed herein; and Y' is O, S, or $NR^2$ which is derived by removing one hydrogen from the corresponding Y.

In some embodiments, L has formula (III):

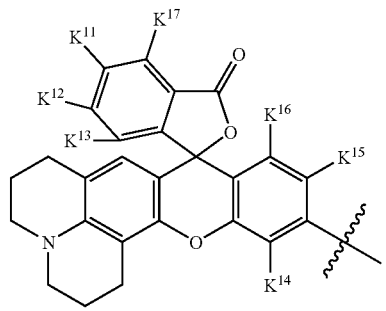

(III)

or a tautomer thereof, wherein $K^{11}$-$K^{17}$ are as disclosed herein. In some embodiments, each of $K^{11}$-$K^{17}$ is independently H, halo, alkyl, halogenated alkyl, heteroalkyl, alkenyl, alkynyl, aryl, aralkyl, alkaryl, heterocyclyl, cycloalkyl, cycloalkenyl, cycloalkynyl, hydroxyalkyl, aminoalkyl, amino, alkylamino, arylamino, dialkylamino, alkylarylamino, diarylamino, acylamino, hydroxy, thio, thioalkyl, alkoxy, alkylthio, alkoxyalkyl, aryloxy, arylalkoxy, acyloxy, cyano, nitro, sulfhydryl, carbamoyl, trifluoromethyl, phenoxy, benzyloxy, sulfonyl, phosphonyl, sulfonate ester or phosphate ester. In other embodiments, each of $K^{11}$, $K^{12}$, $K^{13}$, $K^{14}$, $K^{16}$ and $K^{17}$ is H; and $K^{15}$ is H or halo.

In certain embodiments, the tautomer of formula (III) has formula (IIIa):

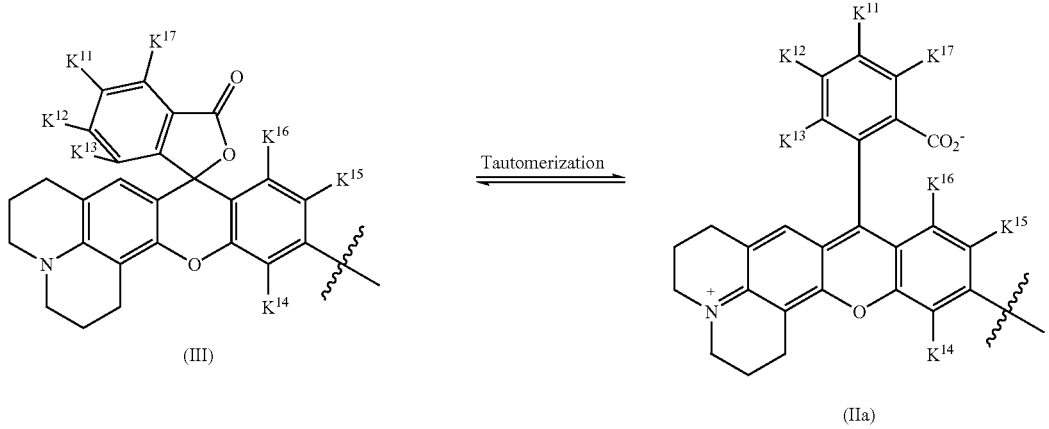

(III)   (IIa)

wherein $K^{11}$-$K^{17}$ are as disclosed herein.

In certain embodiments, L has formula (IV):

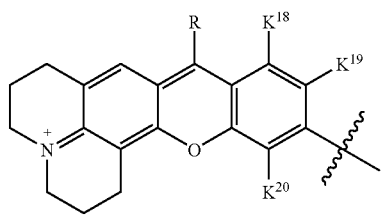

(IV)

or a tautomer thereof, wherein R and $K^{18}$-$K^{20}$ are as disclosed herein. In some embodiments, each of $K^{18}$-$K^{20}$ is independently H, halo, alkyl, halogenated alkyl, heteroalkyl, alkenyl, alkynyl, aryl, aralkyl, alkaryl, heterocyclyl, cycloalkyl, cycloalkenyl, cycloalkynyl, hydroxyalkyl, aminoalkyl, amino, alkylamino, arylamino, dialkylamino, alkylarylamino, diarylamino, acylamino, hydroxy, thio, thioalkyl, alkoxy, alkylthio, alkoxyalkyl, aryloxy, arylalkoxy, acyloxy, cyano, nitro, sulfhydryl, carbamoyl, trifluoromethyl, phenoxy, benzyloxy, sulfonyl, phosphonyl, sulfonate ester or phosphate ester. In other embodiments, each of $K^{18}$ and $K^{20}$ is H; and $K^{19}$ is H or halo.

In some embodiments, L has formula (IVa):

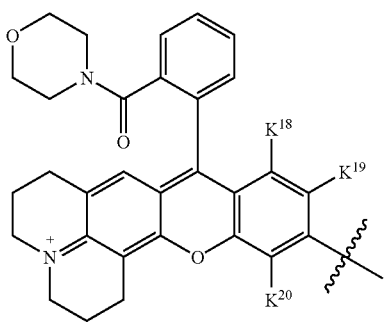

(IVa)

or a tautomer thereof, wherein $K^{18}$-$K^{20}$ are as disclosed herein. In other embodiments, each of $K^{18}$ and $K^{20}$ is H; and $K^{19}$ is halo such as F, Cl, Br or I. In further embodiments, each of $K^{18}$ and $K^{20}$ is H; and $K^{19}$ is Cl.

In some embodiments, L has formula (V):

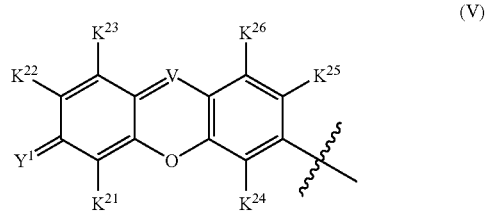

(V)

or a tautomer thereof, wherein $Y^1$, V and $K^{21}$-$K^{26}$ are as disclosed herein.

In certain embodiments, L has formula (V) wherein V is N. In other embodiments, L has formula (Va):

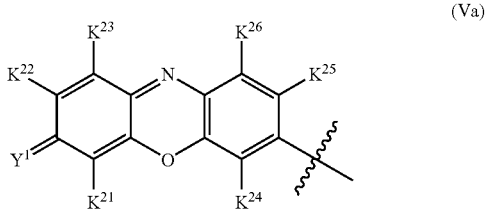

(Va)

or a tautomer thereof, wherein $Y^1$ and $K^{21}$-$K^{26}$ are as disclosed herein. In further embodiments, $Y^1$ is $N^+R^2R^{3'}$. In further embodiments, each of $K^{21}$-$K^{26}$ of formula (Va) is independently H, halo, alkyl, halogenated alkyl, heteroalkyl, alkenyl, alkynyl, aryl, aralkyl, alkaryl, heterocyclyl, cycloalkyl, cycloalkenyl, cycloalkynyl, hydroxyalkyl, aminoalkyl, amino, alkylamino, arylamino, dialkylamino, alkylarylamino, diarylamino, acylamino, hydroxy, thio, thioalkyl, alkoxy, alkylthio, alkoxyalkyl, aryloxy, arylalkoxy, acyloxy, cyano, nitro, sulfhydryl, carbamoyl, trifluoromethyl, phenoxy, benzyloxy, sulfonyl, phosphonyl, sulfonate ester or phosphate ester. In still further embodiments, each of $K^{21}$-$K^{26}$ is H.

In certain embodiments, L has formula (V) wherein V is N; and $Y^1$ is $N^+R^{2'}R^{3'}$. In other embodiments, L has formula (Vb):

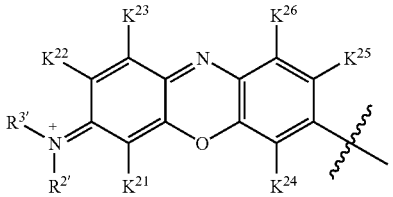

(Vb)

or a tautomer thereof wherein $R^{2'}$, $R^{3'}$ and $K^{21}$-$K^{26}$ are as disclosed herein. In further embodiments, each of $K^{21}$-$K^{26}$ of formula (Vb) is independently H, halo, alkyl, halogenated alkyl, heteroalkyl, alkenyl, alkynyl, aryl, aralkyl, alkaryl, heterocyclyl, cycloalkyl, cycloalkenyl, cycloalkynyl, hydroxyalkyl, aminoalkyl, amino, alkylamino, arylamino, dialkylamino, alkylarylamino, diarylamino, acylamino, hydroxy, thio, thioalkyl, alkoxy, alkylthio, alkoxyalkyl, aryloxy, arylalkoxy, acyloxy, cyano, nitro, sulfhydryl, carbamoyl, trifluoromethyl, phenoxy, benzyloxy, sulfonyl, phosphonyl, sulfonate ester or phosphate ester. In still further embodiments, each of $K^{21}$-$K^{26}$ is H.

In some embodiments, N, $R^{2'}$ and $R^{3'}$ of formula (Vb) together form a 5- or 6-membered saturated heterocycle containing at least a nitrogen. In still further embodiments, the 5- or 6-membered saturated heterocycle is substituted or unsubstituted piperidine, morpholine, pyrrolidine, oxazolidine, thiomorpholine, thiazolidine or piperazine. In still further embodiments, one of $R^{2'}$ and $R^{3'}$ is a Q group as disclosed herein. In still further embodiments, both $R^{2'}$ and $R^{3'}$ are a Q group and $R^{2'}$ and $R^{3'}$ may be the same or different.

In certain embodiments, $R^{2'}$ together with $K^{21}$ or $R^{3'}$ together with $K^{22}$ form a part of a 5- or 6-membered saturated or unsaturated ring wherein the ring is optionally substituted. In other embodiments, $R^{2'}$, $R^{3'}$, $K^{21}$ and $K^{22}$ together form a part of a saturated or unsaturated bicyclic ring wherein the bicyclic ring is substituted or unsubstituted.

In some embodiments, L has formula (V) wherein V is N; and $Y^1$ is O. In other embodiment, L has formula (Vc):

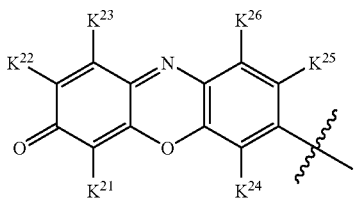

(Vc)

or a tautomer thereof,
wherein $K^{21}$-$K^{26}$ are as disclosed herein. In further embodiments, each of $K^{21}$-$K^{26}$ of formula (Vc) is independently H, halo, alkyl, halogenated alkyl, heteroalkyl, alkenyl, alkynyl, aryl, aralkyl, alkaryl, heterocyclyl, cycloalkyl, cycloalkenyl, cycloalkynyl, hydroxyalkyl, aminoalkyl, amino, alkylamino, arylamino, dialkylamino, alkylarylamino, diarylamino, acylamino, hydroxy, thio, thioalkyl, alkoxy, alkylthio, alkoxyalkyl, aryloxy, arylalkoxy, acyloxy, cyano, nitro, sulfhydryl, carbamoyl, trifluoromethyl, phenoxy, benzyloxy, sulfonyl, phosphonyl, sulfonate ester or phosphate ester. In still further embodiments, each of $K^{21}$-$K^{26}$ is H.

In some embodiments, L has formula (V) where V is CR". In other embodiment, L has formula (Vd):

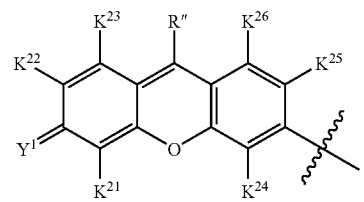

(Vd)

or a tautomer thereof,
wherein R", $Y^1$ and $K^{21}$-$K^{26}$ are as disclosed herein. In further embodiments, $Y^1$ is O or $N^+R^{2'}R^{3'}$. In further embodiments, each of $K^{21}$-$K^{26}$ of formula (Vd) is independently H, halo, alkyl, halogenated alkyl, heteroalkyl, alkenyl, alkynyl, aryl, aralkyl, alkaryl, heterocyclyl, cycloalkyl, cycloalkenyl, cycloalkynyl, hydroxyalkyl, aminoalkyl, amino, alkylamino, arylamino, dialkylamino, alkylarylamino, diarylamino, acylamino, hydroxy, thio, thioalkyl, alkoxy, alkylthio, alkoxyalkyl, aryloxy, arylalkoxy, acyloxy, cyano, nitro, sulfhydryl, carbamoyl, trifluoromethyl, phenoxy, benzyloxy, sulfonyl, phosphonyl, sulfonate ester or phosphate ester. In still further embodiments, each of $K^{21}$-$K^{26}$ is H.

In certain embodiments, $K^{22}$ and $K^{23}$ of formula (Va), (Vb), (Vc) or (Vd) together or $K^{25}$ and $K^{26}$ of formula (Va), (Vb), (Vc) or (Vd) together form a part of a 5- or 6-membered saturated or unsaturated ring such as a benzo ring wherein the 5- or 6-membered saturated or unsaturated ring is substituted or unsubstituted. In further embodiments, $K^{22}$ and $K^{23}$ together or $K^{25}$ and $K^{26}$ together form a benzo ring wherein the benzo ring is substituted or unsubstituted.

In some embodiments, L has formula (VI):

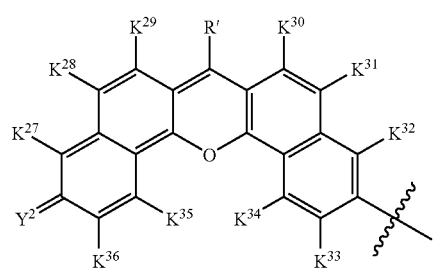

(VI)

or a tautomer thereof wherein R', $Y^2$ and $K^{27}$-$K^{36}$ are as disclosed herein. In other embodiments, $Y^2$ is O or $N^+R^{2'}R^{3'}$ In certain embodiments, L has formula (VI) wherein $Y^2$ is O. In other embodiments, L has formula (VIa):

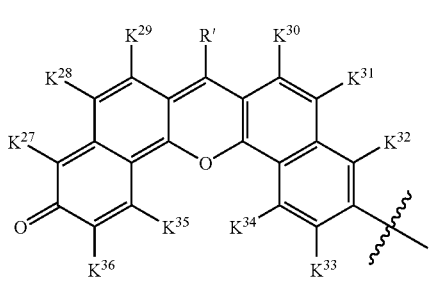

(VIa)

or a tautomer thereof wherein R' and $K^{27}$-$K^{36}$ are as disclosed herein. In further embodiments, each of $K^{27}$-$K^{36}$ of formula (VIa) is independently H, halo, alkyl, halogenated alkyl, heteroalkyl, alkenyl, alkynyl, aryl, aralkyl, alkaryl, heterocyclyl, cycloalkyl, cycloalkenyl, cycloalkynyl, hydroxyalkyl, aminoalkyl, amino, alkylamino, arylamino, dialkylamino, alkylarylamino, diarylamino, acylamino, hydroxy, thio, thioalkyl, alkoxy, alkylthio, alkoxyalkyl, aryloxy, arylalkoxy, acyloxy, cyano, nitro, sulfhydryl, carbamoyl, trifluoromethyl, phenoxy, benzyloxy, sulfonyl, phosphonyl, sulfonate ester or phosphate ester. In still further embodiments, each of $K^{27}$-$K^{36}$ is H.

In certain embodiments, L has formula (VI) wherein $Y^2$ is $N^+R^{2'}R^{3'}$. In other embodiments, L has formula (VIb):

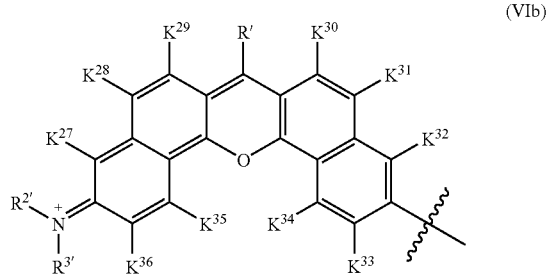

(VIb)

or a tautomer thereof wherein R', $R^{2'}$, $R^{3'}$, and $K^{27}$-$K^{36}$ are as disclosed herein. In further embodiments, each of $K^{27}$-$K^{36}$ of formula (VIb) is independently H, halo, alkyl, halogenated alkyl, heteroalkyl, alkenyl, alkynyl, aryl, aralkyl, alkaryl, heterocyclyl, cycloalkyl, cycloalkenyl, cycloalkynyl, hydroxyalkyl, aminoalkyl, amino, alkylamino, arylamino, dialkylamino, alkylarylamino, diarylamino, acylamino, hydroxy, thio, thioalkyl, alkoxy, alkylthio, alkoxyalkyl, aryloxy, arylalkoxy, acyloxy, cyano, nitro, sulfhydryl, carbamoyl, trifluoromethyl, phenoxy, benzyloxy, sulfonyl, phosphonyl, sulfonate ester or phosphate ester. In still further embodiments, each of $K^{27}$-$K^{36}$ is H.

In further embodiments, N, $R^{2'}$ and $R^{3'}$ of formula (VIb) together form a 5- or 6-membered saturated heterocycle containing at least a nitrogen. In still further embodiments, the 5- or 6-membered saturated heterocycle is substituted or unsubstituted piperidine, morpholine, pyrrolidine, oxazolidine, thiomorpholine, thiazolidine or piperazine. In still further embodiments, one of $R^{2'}$ and $R^{3'}$ is a Q group as disclosed herein. In still further embodiments, both $R^{2'}$ and $R^{3'}$ are a Q group and $R^{2'}$ and $R^{3'}$ may be the same or different.

In some embodiments, $R^{2'}$ together with $K^{27}$ or $R^{3'}$ together with $K^{36}$ form a part of a 5- or 6-membered saturated or unsaturated ring wherein the ring is optionally substituted. In other embodiments, $R^{2'}$, $R^{3'}$, $K^{27}$ and $K^{36}$ together form a part of a saturated or unsaturated bicyclic ring wherein the bicyclic ring is substituted or unsubstituted.

In certain embodiments, $K^{28}$ and $K^{29}$ together, or $K^{30}$ and $K^{31}$ together, or $K^{33}$ and $K^{34}$ together, or $K^{35}$ and $K^{36}$ together form a part of a 5- or 6-membered saturated or unsaturated ring such as a benzo ring wherein the 5- or 6-membered saturated or unsaturated ring is substituted or unsubstituted. In further embodiments, $K^{28}$ and $K^{29}$ together, or $K^{30}$ and $K^{31}$ together, or $K^{33}$ and $K^{34}$ together, or $K^{35}$ and $K^{36}$ together form a benzo ring wherein the benzo ring is substituted or unsubstituted.

In some embodiments, L has formula (XX):

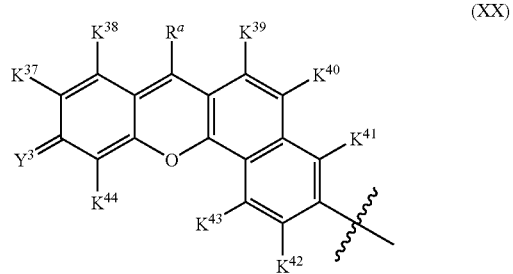

(XX)

or a tautomer thereof wherein $R^a$, $Y^3$ and $K^{37}$-$K^{44}$ are as disclosed herein. In other embodiments, $Y^3$ is O or $N^+R^{2'}R^{3'}$ In certain embodiments, L has formula (XX) wherein $Y^3$ is O. In other embodiments, L has formula (XXa):

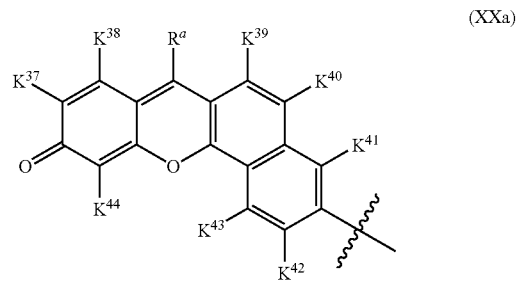

(XXa)

or a tautomer thereof wherein $R^a$, $K^{37}$-$K^{44}$ are as disclosed herein. In further embodiments, each of $K^{37}$-$K^{44}$ of formula (XXa) is independently H, halo, alkyl, halogenated alkyl, heteroalkyl, alkenyl, alkynyl, aryl, aralkyl, alkaryl, heterocyclyl, cycloalkyl, cycloalkenyl, cycloalkynyl, hydroxyalkyl, aminoalkyl, amino, alkylamino, arylamino, dialkylamino, alkylarylamino, diarylamino, acylamino, hydroxy, thio, thioalkyl, alkoxy, alkylthio, alkoxyalkyl, aryloxy, arylalkoxy, acyloxy, cyano, nitro, sulfhydryl, carbamoyl, trifluoromethyl, phenoxy, benzyloxy, sulfonyl, phosphonyl, sulfonate ester or phosphate ester. In still further embodiments, each of $K^{37}$-$K^{44}$ is H. In still further embodiments, $K^{37}$ is Cl or F; and each of $K^{38}$-$K^{44}$ is H.

In certain embodiments, L has formula (XX) wherein $Y^3$ is $N^+R^{2'}R^{3'}$. In other embodiments, L has formula (XXb):

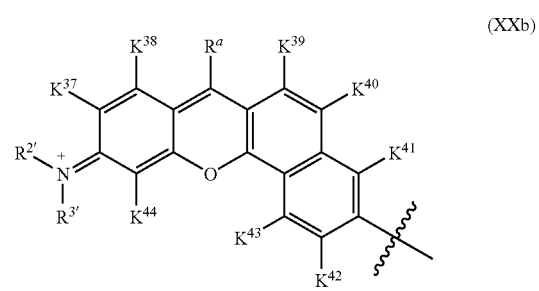

(XXb)

or a tautomer thereof wherein $R^a$, $R^{2'}$, $R^{3'}$, and $K^{37}$-$K^{44}$ are as disclosed herein. In further embodiments, each of $K^{37}$-$K^{44}$ of formula (XXb) is independently H, halo, alkyl, halogenated alkyl, heteroalkyl, alkenyl, alkynyl, aryl, aralkyl, alkaryl, heterocyclyl, cycloalkyl, cycloalkenyl, cycloalkynyl, hydroxyalkyl, aminoalkyl, amino, alkylamino, arylamino, dialkylamino, alkylarylamino, diarylamino, acylamino, hydroxy, thio, thioalkyl, alkoxy, alkylthio, alkoxyalkyl, aryloxy, arylalkoxy, acyloxy, cyano, nitro, sulfhydryl, carbamoyl, trifluoromethyl, phenoxy, benzyloxy, sulfonyl, phosphonyl, sulfonate ester or phosphate ester. In still further embodiments, each of $K^{37}$-$K^{44}$ is H.

In further embodiments, N, $R^{2'}$ and $R^{3'}$ of formula (XXb) together form a 5- or 6-membered saturated heterocycle containing at least a nitrogen. In still further embodiments, the 5- or 6-membered saturated heterocycle is substituted or unsubstituted piperidine, morpholine, pyrrolidine, oxazolidine, thiomorpholine, thiazolidine or piperazine. In still further embodiments, one of $R^{2'}$ and $R^{3'}$ is a Q group as disclosed herein. In still further embodiments, both $R^{2'}$ and $R^{3'}$ are a Q group and $R^{2'}$ and $R^{3'}$ may be the same or different.

In some embodiments, $R^{2'}$ together with $K^{37}$ or $R^{3'}$ together with $K^{44}$ form a part of a 5- or 6-membered saturated or unsaturated ring wherein the ring is optionally substituted. In other embodiments, $R^{2'}$, $R^{3'}$, $K^{37}$ and $K^{44}$ together form a part of a saturated or unsaturated bicyclic ring wherein the bicyclic ring is substituted or unsubstituted.

In certain embodiments, $K^{37}$ and $K^{38}$ together, or $K^{39}$ and $K^{40}$ together, or $K^{42}$ and $K^{43}$ together form a part of a 5- or 6-membered saturated or unsaturated ring such as a benzo ring wherein the 5- or 6-membered saturated or unsaturated ring is substituted or unsubstituted. In further embodiments, $K^{37}$ and $K^{38}$ together, or $K^{39}$ and $K^{40}$ together, or $K^{42}$ and $K^{43}$ together form a benzo ring wherein the benzo ring is substituted or unsubstituted.

In some embodiments, L has formula (XXI):

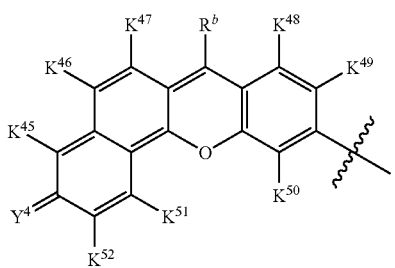

(XXI)

or a tautomer thereof wherein $R^{b}$, $Y^{4}$ and $K^{45}$-$K^{52}$ are as disclosed herein. In other embodiments, $Y^{4}$ is O or $N^{+}R^{2'}R^{3'}$ In certain embodiments, L has formula (XXI) wherein $Y^{4}$ is O. In other embodiments, L has formula (XXIa):

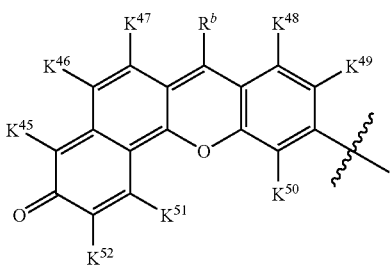

(XXIa)

or a tautomer thereof wherein $R^{b}$, $K^{45}$-$K^{52}$ are as disclosed herein. In further embodiments, each of $K^{45}$-$K^{52}$ of formula (XXIa) is independently H, halo, alkyl, halogenated alkyl, heteroalkyl, alkenyl, alkynyl, aryl, aralkyl, alkaryl, heterocyclyl, cycloalkyl, cycloalkenyl, cycloalkynyl, hydroxyalkyl, aminoalkyl, amino, alkylamino, arylamino, dialkylamino, alkylarylamino, diarylamino, acylamino, hydroxy, thio, thioalkyl, alkoxy, alkylthio, alkoxyalkyl, aryloxy, arylalkoxy, acyloxy, cyano, nitro, sulfhydryl, carbamoyl, trifluoromethyl, phenoxy, benzyloxy, sulfonyl, phosphonyl, sulfonate ester or phosphate ester. In still further embodiments, each of $K^{46}$-$K^{51}$ is H, and at least one of $K^{45}$ and $K^{52}$ is independently Cl or F.

In certain embodiments, L has formula (XXI) wherein $Y^{4}$ is $N^{+}R^{2'}R^{3'}$. In other embodiments, L has formula (XXIb):

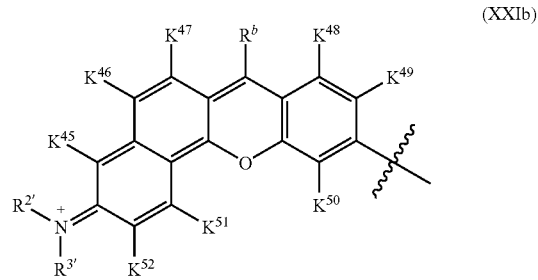

(XXIb)

or a tautomer thereof wherein $R^{b}$, $R^{2'}$, $R^{3'}$, and $K^{45}$-$K^{52}$ are as disclosed herein. In further embodiments, each of $K^{45}$-$K^{52}$ of formula (XXIb) is independently H, halo, alkyl, halogenated alkyl, heteroalkyl, alkenyl, alkynyl, aryl, aralkyl, alkaryl, heterocyclyl, cycloalkyl, cycloalkenyl, cycloalkynyl, hydroxyalkyl, aminoalkyl, amino, alkylamino, arylamino, dialkylamino, alkylarylamino, diarylamino, acylamino, hydroxy, thio, thioalkyl, alkoxy, alkylthio, alkoxyalkyl, aryloxy, arylalkoxy, acyloxy, cyano, nitro, sulfhydryl, carbamoyl, trifluoromethyl, phenoxy, benzyloxy, sulfonyl, phosphonyl, sulfonate ester or phosphate ester. In still further embodiments, each of $K^{45}$-$K^{52}$ is H.

In further embodiments, N, $R^{2'}$ and $R^{3'}$ of formula (XXIb) together form a 5- or 6-membered saturated heterocycle containing at least a nitrogen. In still further embodiments, the 5- or 6-membered saturated heterocycle is substituted or unsubstituted piperidine, morpholine, pyrrolidine, oxazolidine, thiomorpholine, thiazolidine or piperazine. In still further embodiments, one of $R^{2'}$ and $R^{3'}$ is a Q group as disclosed herein. In still further embodiments, both $R^{2'}$ and $R^{3'}$ are a Q group and $R^{2'}$ and $R^{3'}$ may be the same or different.

In some embodiments, $R^{2'}$ together with $K^{45}$ or $R^{3'}$ together with $K^{52}$ form a part of a 5- or 6-membered saturated or unsaturated ring wherein the ring is optionally substituted. In other embodiments, $R^{2'}$, $R^{3'}$, $K^{45}$ and $K^{52}$ together form a part of a saturated or unsaturated bicyclic ring wherein the bicyclic ring is substituted or unsubstituted.

In certain embodiments, $K^{46}$ and $K^{47}$ together, or $K^{48}$ and $K^{49}$ together, or $K^{51}$ and $K^{52}$ together form a part of a 5- or 6-membered saturated or unsaturated ring such as a benzo ring wherein the 5- or 6-membered saturated or unsaturated ring is substituted or unsubstituted. In further embodiments, $K^{46}$ and $K^{47}$ together, or $K^{48}$ and $K^{49}$ together, or $K^{51}$ and $K^{52}$ form a benzo ring wherein the benzo ring is substituted or unsubstituted.

In some embodiments, each of R, R', R", $R^a$ and $R^b$ is independently a substituted or unsubstituted phenyl having formula (VII):

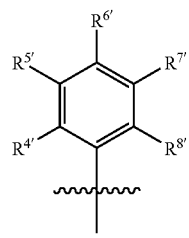

(VII)

wherein each of $R^{4'}$, $R^{5'}$, $R^{6'}$, $R^{7'}$ and $R^{8'}$ is independently H, alkyl, alkenyl, alkynyl, heteroalkyl, cycloalkyl, cycloalkenyl, cycloalkynyl, aryl, alkylaryl, arylalkyl, heterocyclyl, hydroxy, alkoxy, alkoxyalkyl, alkoxyalkoxy, acyl, alkylcarbonylalkyl, halogentaed alkylcarbonylalkyl such as trifluoromethylcarbonylalkyl, aminoalkyl, carboxyalkyl, alkoxycarbonyl, alkoxycarbonylalkyl, aminocarbonyl, or $NR^9R^{10}$ or $R^{4'}$ and $R^{5'}$ together, $R^{5'}$ and $R^{6'}$ together, $R^{6'}$ and $R^{7'}$ together or $R^{7'}$ and $R^{8'}$ together forming a part of a 5- or 6-membered cycloalkyl, heterocyclyl, aryl or heteroaryl ring fused with the phenyl ring of formula (VII); and each of $R^9$ and $R^{10}$ is independently H, alkyl, alkenyl, alkynyl, alkoxyalkyl, alkanoyl, alkenoyl, alkynoyl, cycloalkyl, cycloalkenyl, cycloalkynyl, aryl, alkaryl, arylalkyl, aryloyl, or polyether.

In certain embodiments, $R^{4'}$, $R^{5'}$, $R^{6'}$ and $R^{7'}$ is independently H; and $R^{8'}$ is —COOH, —$COR^{17}$, —$COOR^{18}$, or —$CONR^{19}R^{20}$, wherein $R^{17}$, $R^{18}$, $R^{19}$ and $R^{20}$ is independently H, alkyl, alkenyl, alkynyl, heteroalkyl, cycloalkyl, cycloalkenyl, cycloalkynyl, aryl, alkylaryl, arylalkyl, heterocyclyl, hydroxy, alkoxy, alkoxyalkyl, alkoxyalkoxy, acyl, alkylcarbonylalkyl, halogentaed alkylcarbonylalkyl, aminoalkyl, carboxyalkyl, alkoxycarbonyl, alkoxycarbonylalkyl, aminocarbonyl, or $NR^9R^{10}$, or N, $R^{19}$ and $R^{20}$ together forming a 5- or 6-membered heterocycle having at least a nitrogen atom. In other embodiments, $R^{8'}$ is —$CONR^{19}R^{20}$ and N, $R^{19}$ and $R^{20}$ together form a 5- or 6-saturated heterocycle. In further embodiments, the heterocycle is substituted or unsubstituted piperidine, morpholine, pyrrolidine, oxazolidine, thiomorpholine, thiazolidine or piperazine. In still further embodiments, $R^{8'}$ is a —COOH group. In still further embodiments, each of $R^{4'}$, $R^{5'}$, $R^{6'}$ and $R^{7'}$ is H; and $R^{8'}$ is a —COOH group. In some embodiments, each of $R^{4'}$, $R^{5'}$, $R^{6'}$ and $R^{7'}$ is independently H; and $R^{8'}$ is methyl, methoxy or any other group that can provide sufficient steric hinderance to cause the benzene ring out of the plane of the polycyclic ring such as the xanthenes ring.

In some embodiments, L has one of formulae (a)-(v):

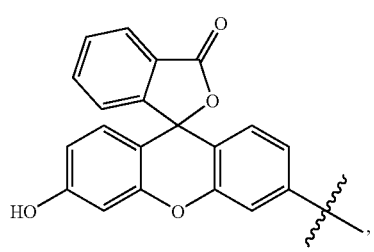

(a)

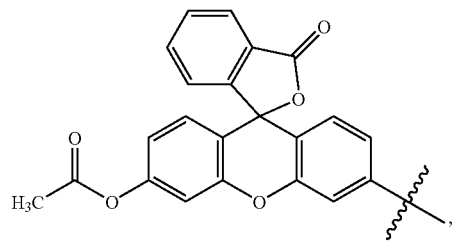

(b)

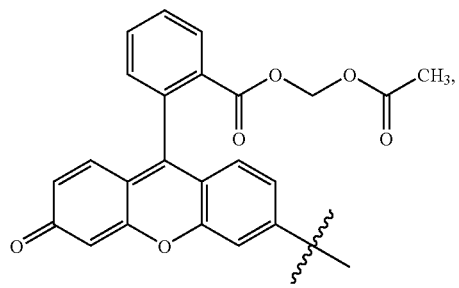

(c)

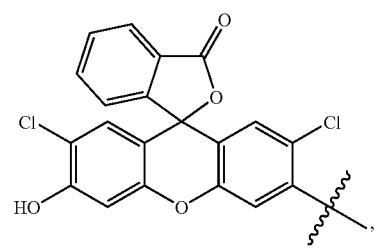

(d)

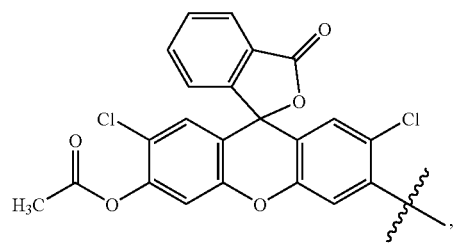

(e)

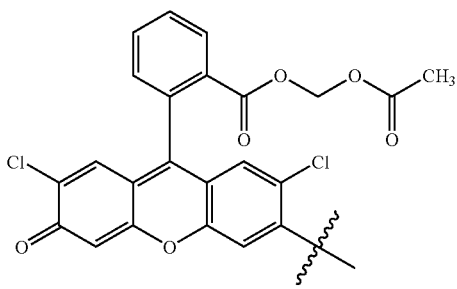

(f)

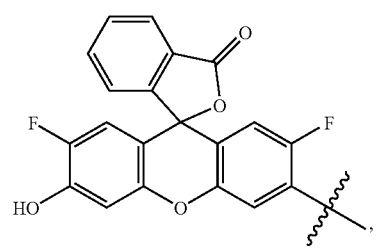

(g)

-continued
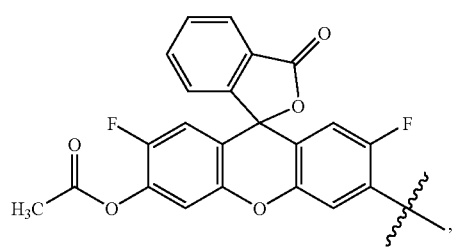
(h)
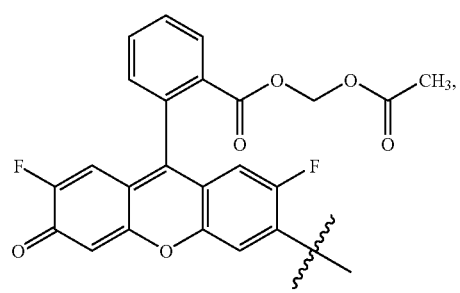
(i)
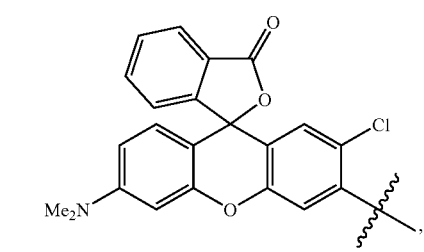
(j)
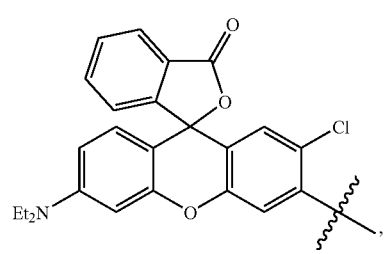
(k)
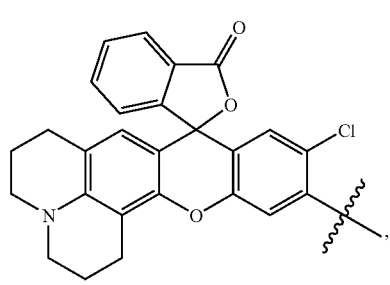
(l)
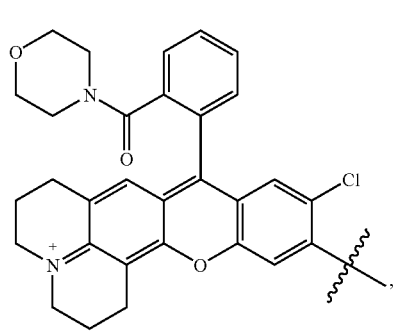
(m)
-continued
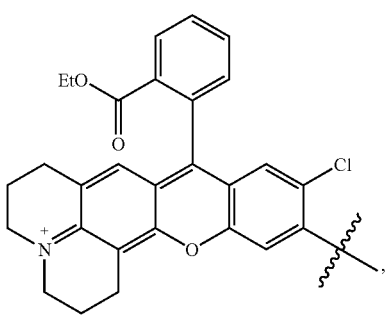
(n)
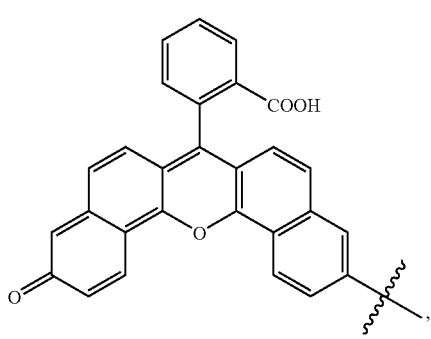
(o)
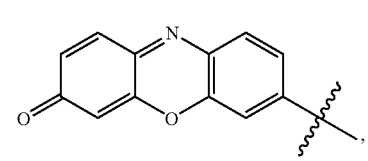
(p)
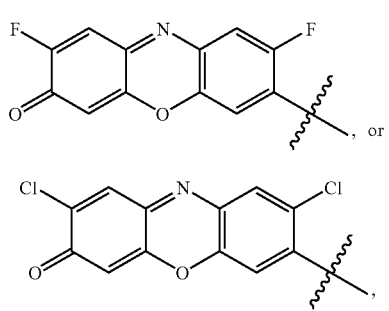
(q)
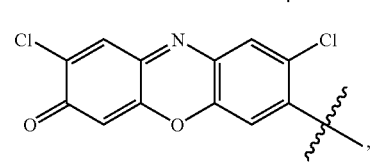
, or
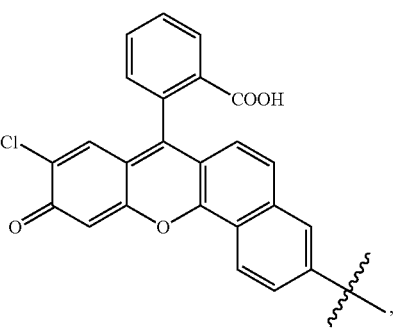
(r)
(s)

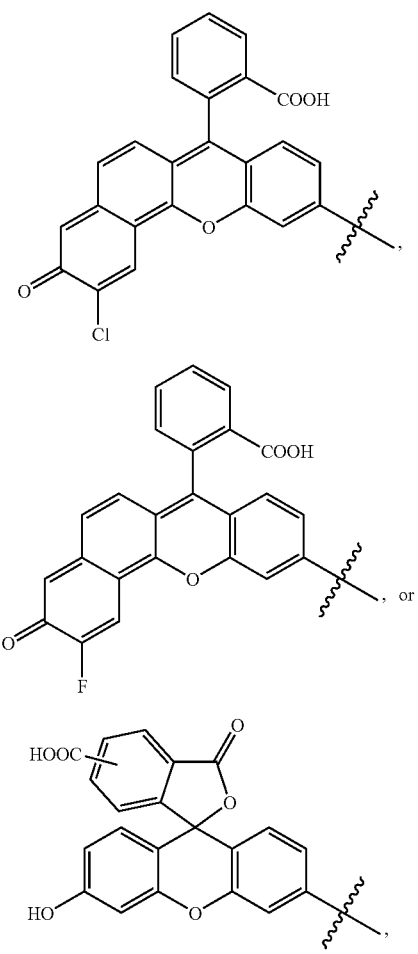

or a tautomer thereof, wherein each of formulae (a)-(v) is independently unsubstituted or substituted.

In certain embodiments, Q of formula (I) is a substituted or unsubstituted phenyl having formula (VIIa):

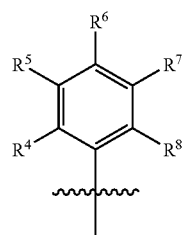

wherein $R^4$, $R^5$, $R^6$, $R^7$ and $R^8$ is independently H, alkyl, alkenyl, alkynyl, heteroalkyl, cycloalkyl, cycloalkenyl, cycloalkynyl, aryl, alkylaryl, arylalkyl, heterocyclyl, hydroxy, alkoxy, alkoxyalkyl, alkoxyalkoxy, acyl, alkylcarbonylalkyl, halogentaed alkylcarbonylalkyl such as trifluoromethylcarbonylalkyl, aminoalkyl, carboxyalkyl, alkoxycarbonyl, alkoxycarbonylalkyl, aminocarbonyl, or $NR^9R^{10}$, or $R^4$ and $R^5$ together, $R^5$ and $R^6$ together, $R^6$ and $R^7$ together or $R^7$ and $R^8$ together forming a part of a 5- or 6-membered cycloalkyl, heterocyclyl, aryl or heteroaryl ring fused with the phenyl ring of formula (VIIa); and each of $R^9$ and $R^{10}$ is independently H, alkyl, alkenyl, alkynyl, alkoxyalkyl, alkanoyl, alkenoyl, alkynoyl, cycloalkyl, cycloalkenyl, cycloalkynyl, aryl, alkaryl, arylalkyl, aryloyl, or polyether.

In certain embodiments, $R^6$ of formula (VIIa) is $NR^9R^{10}$. In other embodiments, $R^1$ of formula (I) is H, alkyl, halogenated alkyl, heteroalkyl, alkenyl, alkynyl, aryl, aralkyl, alkaryl, heterocyclyl, cycloalkyl, cycloalkenyl, and cycloalkynyl; each of $R^4$ $R^5$, $R^6$, $R^7$ and $R^8$ of formula (VIa) is independently H, halogen, alkyl, alkoxy, or polyether; $R^6$ is $OR^{11}$ or $CH_2CH_2COR$, where $R^{11}$ is H, alkyl, alkoxyalkyl, alkanoyl, or polyether; $R^{12}$ is an electron-withdrawing group selected from $CF_3$, halogen-substituted lower alkyl (e.g., $CF_nH_{3-n}$, wherein n is 1, 2, or 3), or $(C=O)-O-V^2$, wherein $V^2$ is a group selected from alkyl, alkenyl, alkynyl, cycloalkyl, cycloalkenyl, cycloalkynyl, aryl, alkaryl or arylalkyl.

In some embodiments, $R^6$ of Q is $-OCH_2OCH_3$, OH, $NR^9R^{10}$, $-CH_2CH_2C(=O)CF_3$, or $-CH_2CH_2C(=O)OCH_3$ where each of $R^9$ and $R^{10}$ is independently H or alkyl; and each of $R^4$, $R^5$, $R^7$ and $R^8$ is H. In other embodiments, $R^6$ is OH, $NH_2$ or $-CH_2CH_2C(=O)CF_3$.

In certain embodiments, $R^1$ is H, alkyl, halogenated alkyl, heteroalkyl, alkenyl, alkynyl, aryl, aralkyl, alkaryl, heterocyclyl, cycloalkyl, cycloalkenyl, and cycloalkynyl; each of $R^4$, $R^5$, $R^6$, $R^7$ and $R^8$ is independently H, halogen, alkyl, alkoxy, or polyether; $R^6$ is $OR^{11}$ or $CH_2CH_2COR^{12}$, where $R^{11}$ is H, alkyl, alkoxyalkyl, alkanoyl, or polyether; $R^{12}$ is an electron-withdrawing group selected from $CF_3$, halogen-substituted lower alkyl, or $(C=O)-O-V^2$, wherein $V^2$ is a group selected from alkyl, alkenyl, alkynyl, cycloalkyl, cycloalkenyl, cycloalkynyl, aryl, alkaryl or arylalkyl.

In some embodiments, when L has formula (II) where Y is $NR^2R^3$, then $R^6$ of Q is hydroxy, alkenyl, alkynyl, heteroalkyl, cycloalkyl, cycloalkenyl, cycloalkynyl, aryl, heterocyclyl, alkoxyalkyl, alkoxyalkoxy, acyl, alkylcarbonylalkyl, halogentaed alkylcarbonylalkyl such as trifluoromethylcarbonylalkyl, carboxyalkyl, alkoxycarbonyl, alkoxycarbonylalkyl or aminocarbonyl, or $R^4$ and $R^5$ together, $R^5$ and $R^6$ together, $R^6$ and $R^7$ together or $R^7$ and $R^8$ together form a 5- or 6-membered cycloalkyl, heterocyclyl, aryl or heteroaryl ring fused with the phenyl ring of formula (VIIa).

In some embodiments, the aromatic amine compounds have formula (I):

wherein L has one of formulae (II)-(VI), (XX), (XXI), (Va)-(Vd), (VIa)-(VIb), (XXa)-(XXb), (XXIa)-(XXIb), and (a)-(v) as disclosed herein; Q has formula (VIIa) as disclosed herein; and $R^1$ is as disclosed herein.

When any of the aromatic amine compounds, such as formula (IVa), formula (Vb), formula (VIIb), formula (IXb) or Compound 3, is positively charged, the positive charge may be balanced by any suitable counteranion known to a skilled artisan. Some non-limiting examples of suitable counteranion include halides such as fluoride, chloride, bromide and iodide, carboxylates such as formate and acetate, hydrogen carbonate, nitrate, nitrite and the like. In some embodiments, the counteranion is chloride. In some embodiments, the counteranion is acetate.

In certain embodiments, the aromatic amine compounds disclosed herein include Compounds 1a-1d, 2, 3, 4a-4e and 5a-5d:
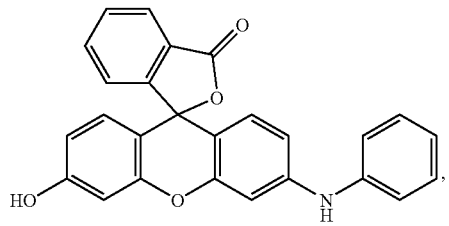
(1a)
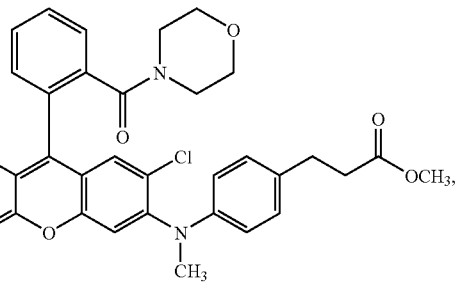
(3)
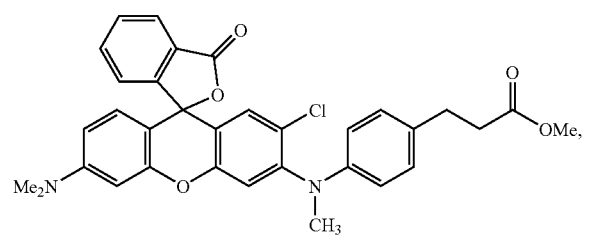
(1b)
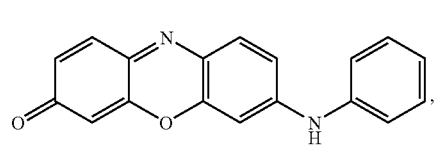
(4a)
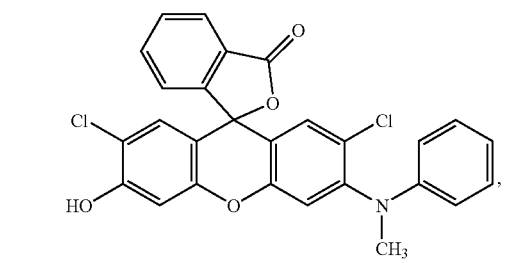
(1c)
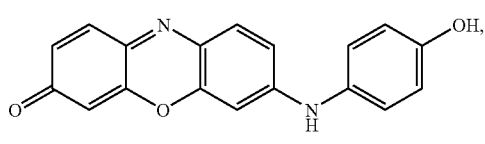
(4b)
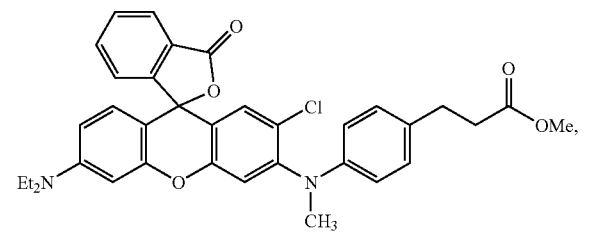
(1d)
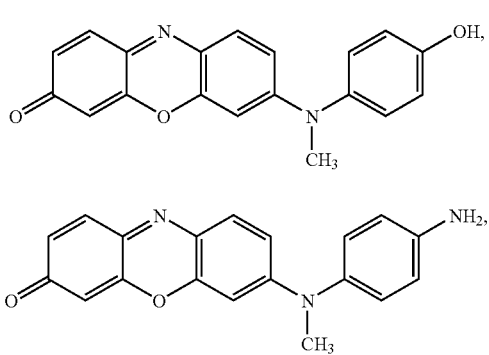
(4c)
(4d)
(4e)
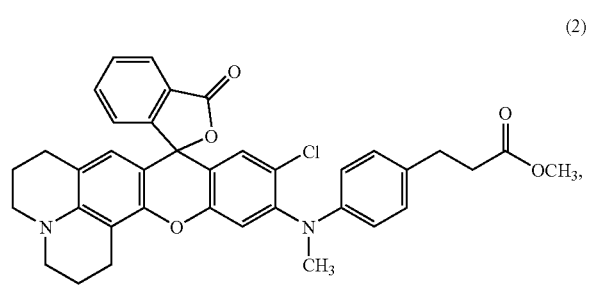
(2)
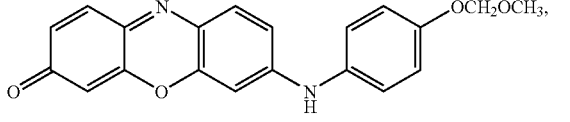
(5a)
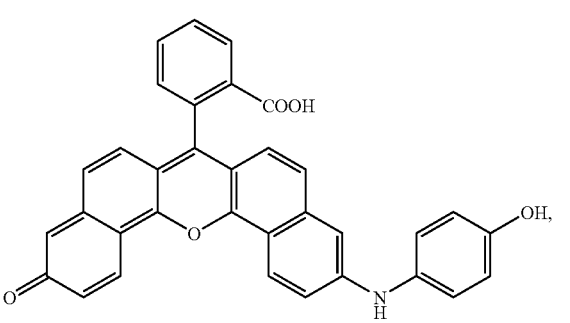

(5b)
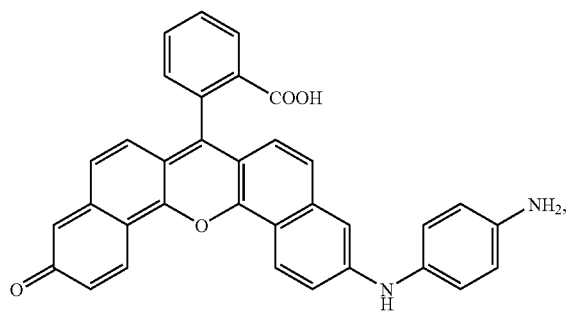

(5c)
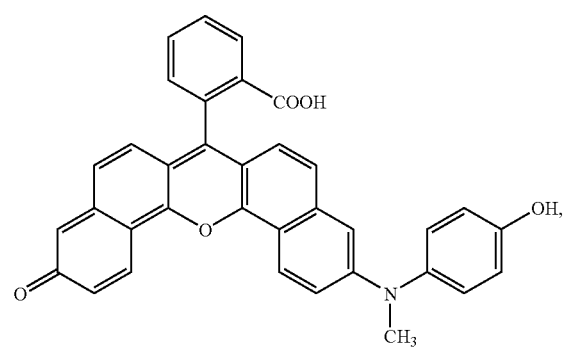

(5d)
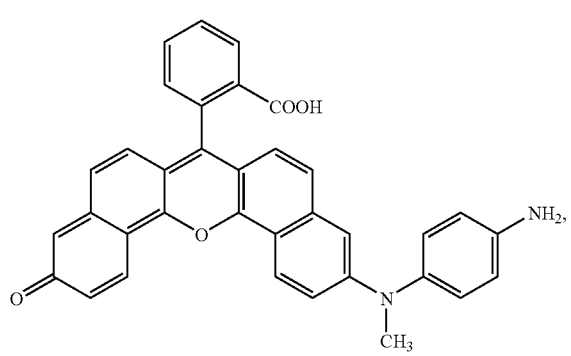

(10)
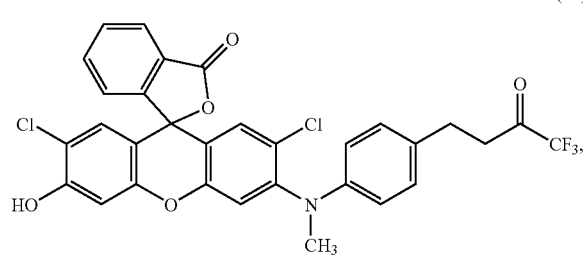

(12)
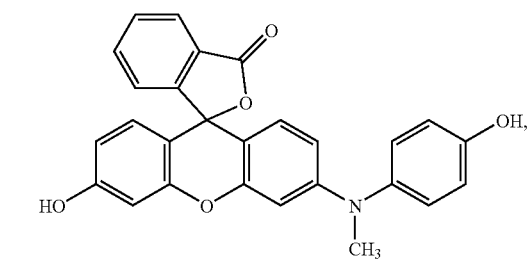

(12a)
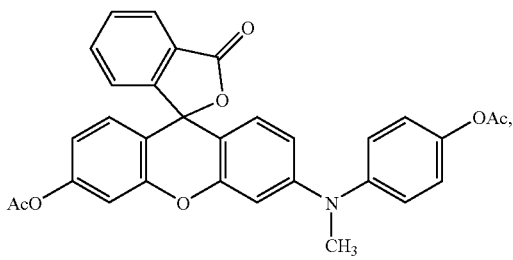

(14)
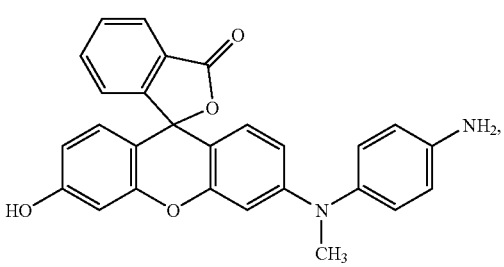

(22)
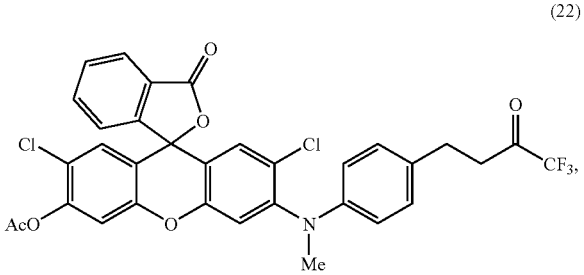

(30)
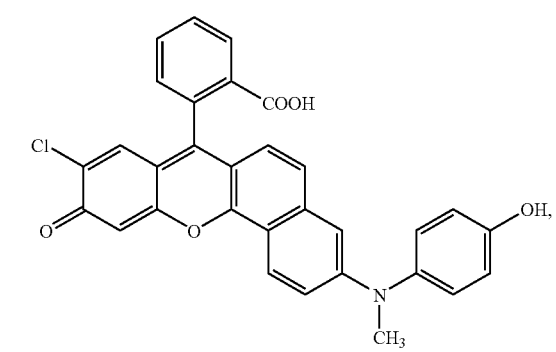

or a tautomer thereof, wherein each of Compounds 1a-1d, 2, 3, 4a-4e, 5a-5d, 10, 12, 12a, 14, 22, and 30 is independently substituted or unsubstituted.

In certain embodiments, the aromatic amine compound is Compound (10). In other embodiments, the aromatic amine compound is Compound (12). In further embodiments, the aromatic amine compound is Compound (12a). In still further embodiments, the aromatic amine compound is Compound (14). In still further embodiments, the aromatic amine compound is Compound (22). In other embodiments, the aromatic amine compound is Compound (30).

In some embodiments, the aromatic amine compound is Compound (30). In other embodiments, the tautomer of Compound (30) has formlua (30a) as shown below.

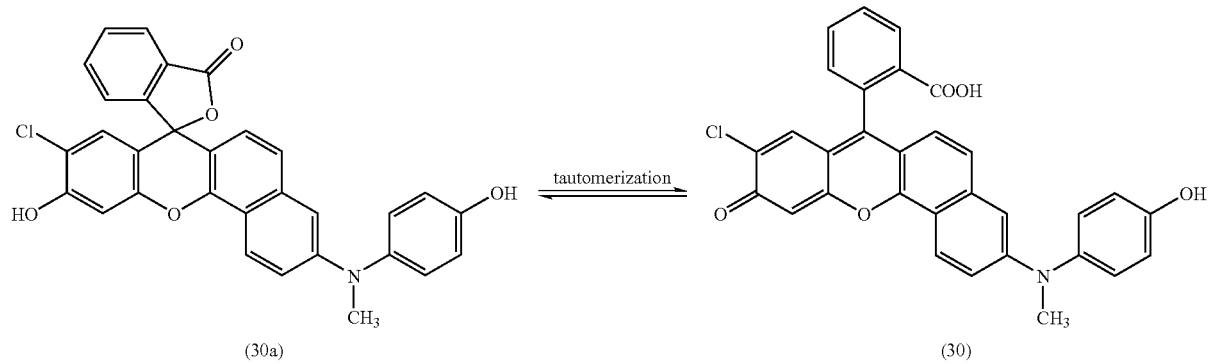

(30a) tautomerization (30)

Aromatic Amine Compounds as Luminescence Quenchers

In certain embodiments, the aromatic amine compounds having formula (I) can be used as luminescence quenchers or luminescence quenching compounds. In certain embodiments, the luminescence quenching compounds have formula (VIII) or (IX):

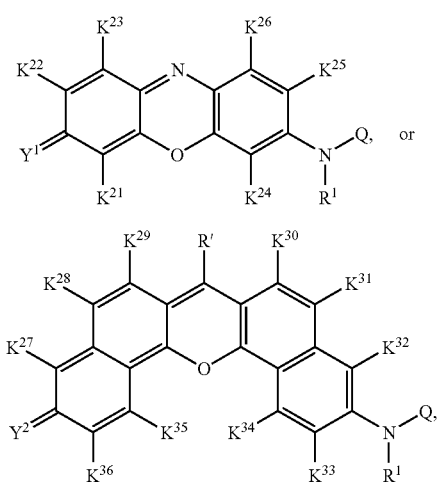

(VIII)

or (IX)

wherein $Y^1$, $Y^2$, Q, R', $R^1$ and $K^{21}$-$K^{36}$ are as disclosed herein.

In certain embodiments, each of $Y^1$ or $Y^2$ is independently O. In other embodiments, each of $Y^1$ or $Y^2$ is independently $N^+R^{2'}R^{3'}$. In further embodiments, each of $Y^1$ or $Y^2$ is independently $NR^{2'}R^{3'}$. In still further embodiments, the luminescence quenching compounds have formula (VIIIa), (VIIIb), (IXa) or (IXb):

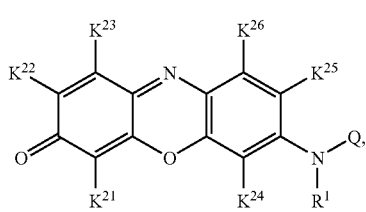

(VIIIa)

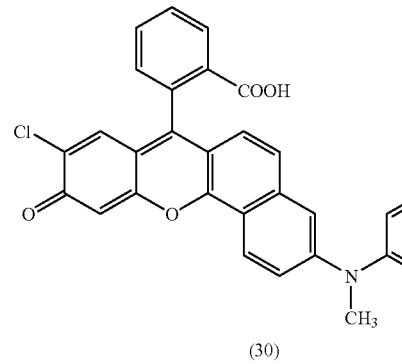

(VIIIb)

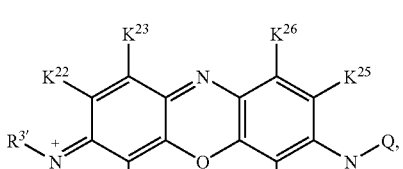

(IXa)

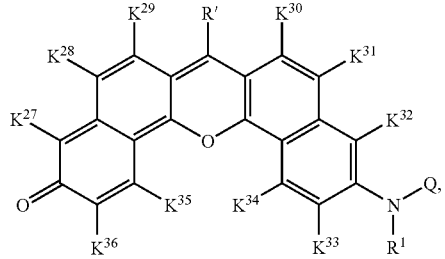

(IXb)

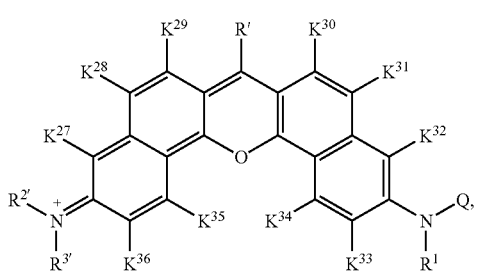

wherein Q, R', $R^1$ and $K^{21}$-$K^{36}$ are as disclosed herein.

In certain embodiments, N, $R^{2'}$ and $R^{3'}$ of formula (VIIb) or (IXb) together form a 4-, 5-, 6-, 7- or 8-membered saturated heterocycle containing at least a nitrogen. In other embodiments, N, $R^{2'}$ and $R^{3'}$ of formula (VIIb) or (IXb) together form a 5- or 6-membered saturated heterocycle. In further embodiments, N, $R^{2'}$ and $R^{3'}$ of formula (VIIb) or (IXb) together form a 5- or 6-membered saturated heterocycle selected from substituted or unsubstituted piperidine, morpholine, pyrrolidine, oxazolidine, thiomorpholine, thiazolidine or piperazine. In still further embodiments, one of $R^{2'}$ and $R^{3'}$ of formula (VIIb) or (IXb) is Q as disclosed herein. In still further embodiments, both $R^{2'}$ and $R^{3'}$ are Q and $R^{2'}$ and $R^{3'}$ may be the same or different.

In some embodiments, N, Q and $R^1$ of formula (VIII), (VIII), (VIIIa), (VIIIb), (IXa) or (IXb) together form a 5- or 6-membered saturated heterocycle containing at least a nitrogen. In other embodiments, the 5- or 6-membered saturated heterocycle is substituted or unsubstituted piperidine, morpholine, pyrrolidine, oxazolidine, thiomorpholine, thiazolidine or piperazine. In further embodiments, $R^1$ is a Q group as disclosed herein. In still further embodiments, both $R^1$ and Q group may be the same or different.

In certain embodiments, $R^{2'}$ together with $K^{21}$ or $R^{3'}$ together with $K^{22}$ of formula (VIIIb) form a part of a 5- or 6-membered saturated or unsaturated ring wherein the ring is optionally substituted. In other embodiments, $R^{2'}$, $R^{3'}$, $K^{21}$ and $K^{22}$ together form a part of a saturated or unsaturated bicyclic ring wherein the bicyclic ring is substituted or unsubstituted.

In some embodiments, $R^{2'}$ together with $K^{27}$ or $R^{3'}$ together with $K^{36}$ of formula (IXb) form a part of a 5- or 6-membered saturated or unsaturated ring wherein the ring is optionally substituted. In other embodiments, $R^{2'}$, $R^{3'}$, $K^{27}$ and $K^{36}$ together form a part of a saturated or unsaturated bicyclic ring wherein the bicyclic ring is substituted or unsubstituted.

In certain embodiments, $K^{22}$ and $K^{23}$ together or $K^{25}$ and $K^{26}$ together form a part of a 5- or 6-membered saturated or unsaturated ring such as a benzo ring wherein the 5- or 6-membered saturated or unsaturated ring is substituted or unsubstituted. In further embodiments, $K^{22}$ and $K^{23}$ together or $K^{25}$ and $K^{26}$ together form a benzo ring wherein the benzo ring is substituted or unsubstituted.

In some embodiments, the luminescence quenching compounds include Compounds 4a-4e and 5a-5d:

(4a)
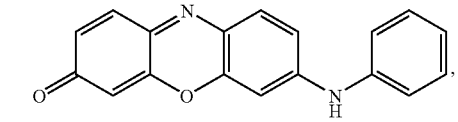

(4b)
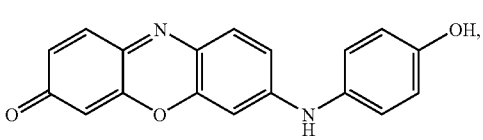

(4c)
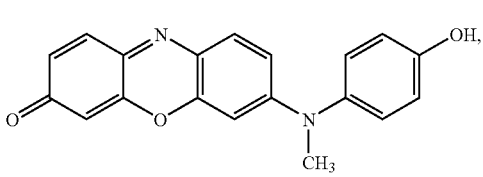

(4d)
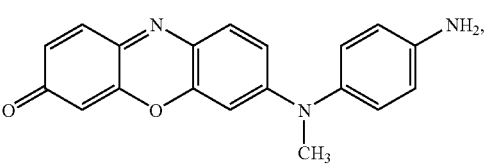

(4e)
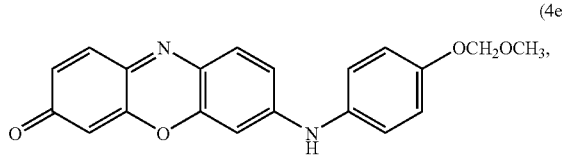

(5a)
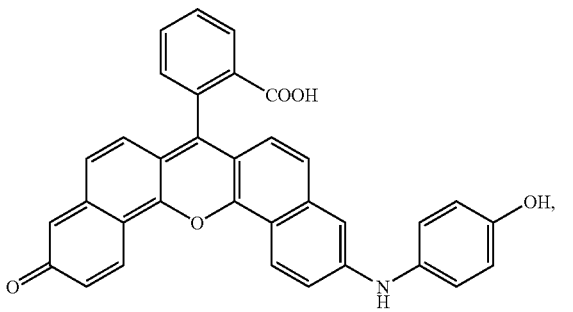

(5b)
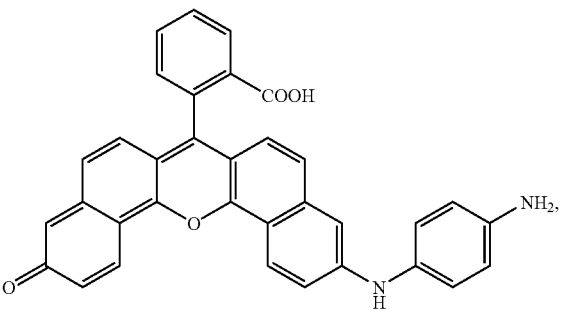

(5c)
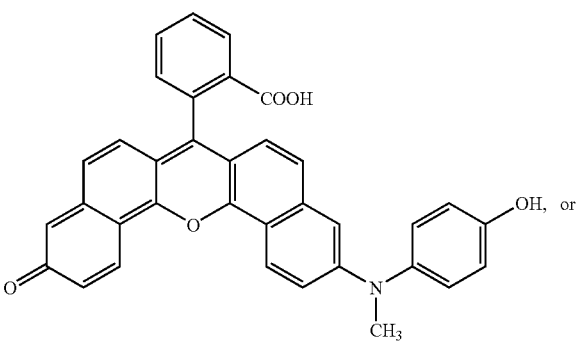

(5d)

wherein each of Compounds 4a-4e and 5a-5d is independently substituted or unsubstituted.

In some embodiments, at least one of the L, $R^1$ and Q groups of the aromatic amine compounds of formula (I) is substituted by a reactive group (Rg) or a conjugated group (Cg) wherein Rg or Cg is optionally attached to the aromatic amine compounds disclosed herein through a linkage group, —X—. In other embodiments, at least one of the L, $R^1$ and Q groups of the aromatic amine compounds disclosed herein is substituted by an —X-Rg or —X-Cg group. In other embodiments, the L group of the aromatic amine compounds of formula (I) is substituted by an —X-Rg or —X-Cg group.

In some embodiments, X is or comprises a bond or a linking group such as O, S, an aminylene group (e.g., an NR group where R is H, an alkyl group, an alkenyl group, an alkynyl group, a carboxyl group, an acyl group, an aromatic group, or a heterocyclic group), a sulfonyl group, an organic linking group, or a combination thereof. The organic linking group disclosed herein may be a divalent linking organic group connecting any of two fragments, such as L, $R^1$, Q, Rg or Cg, of a chemical formula together. Some non-limiting examples of the divalent organic linking group include a carbonyl group, an alkylene group, an arylene group, a divalent heterocyclic group, and combinations thereof. Another non-limiting example of the divalent organic linking group includes a —$(CH_2)_m$— group, where m is an integer between 1 and 50, inclusive, and one or more of the methylene groups is optionally replaced by O, S, N, C, B, Si, P, C=O, O=S=O, a heterocyclic group, an aromatic group, an $NR_a$ group, a $CR_b$ group, a $CR_cR_d$ group, a $SiR_eR_f$ group, a $BR_g$ group, or a $P(=O)R_h$ group, where $R_a$, $R_b$, $R_c$, $R_d$, $R_e$, $R_f$, $R_g$, and $R_h$ are, each independently, a bond, H, a hydroxyl group, a thiol group, a carboxyl group, an amino group, a halogen, an acyl group, an alkoxy group, an alkylsulfanyl group, an alkenyl group, such as a vinyl group, an allyl group, and a 2-phenylethenyl group, an alkynyl group, a heterocyclic group, an aromatic group, a part of a ring group, such as cycloalkyl groups, heterocyclic groups, and a benzo group, or an alkyl group where one or more of the hydrogens of the alkyl group is optionally replaced by an aromatic group, a hydroxyl group, a thiol group, a carboxyl group, an amino group, or a halogen. A non-limiting example of the aminylene group includes an NR group where R is H, an alkyl group, an alkenyl group, an alkynyl group, an acyl group, an aromatic group, and a heterocyclic group.

In certain embodiments, the organic linking group may have a valence of 3 or more and, therefore, may link any of 3 or more fragments, such as L, $R^1$, Q, Rg or Cg, of a chemical formula together. A non-limiting example of an organic linking group having a valence of 3 is a trivalent organic linking group created by replacing a methylene group in the —$(CH_2)_m$— group with a $CR_b$ group. Another non-limiting example of an organic linking group having a valence of 4 is a tetravalent organic linking group created by replacing a methylene group in the —$(CH_2)_m$— group with a carbon atom. Another non-limiting example of an organic linking group having a valence of 3 is a trivalent organic linking group created by replacing a methylene group in the —$(CH_2)_m$— group with N, P, or B. A further non-limiting example of an organic linking group having a valence of 4 is a tetravalent organic linking group created by replacing two methylene groups in the —$(CH_2)_m$— group with two $CR_b$ groups. Based on the disclosure herein, a person skill in the art may create an organic linking group having a valence greater than 2 by replacing at least one methylene group in the —$(CH_2)_m$— group with at least an atom or a group having a valence of 3 or more, such as N, P, B, C, Si, a $CR_b$ group, an aromatic group having a valence greater than 2, and a heterocyclic group having a valence greater than 2.

In other embodiments of interest, the organic linking group may comprise at least an unsaturated bond, such as a —$CR_b$=N— bond, a double bond or a triple bond. A non-limiting example of an organic linking group having a double bond is an unsaturated organic linking group created by replacing two adjacent methylene groups in the —$(CH_2)_m$— group with two $CR_b$ groups. The double bond is located between the two adjacent $CR_b$ groups. Another non-limiting example of an organic linking group having a triple bond is an unsaturated organic linking group created by replacing two adjacent methylene groups in the —$(CH_2)_m$— group with two carbon atoms respectively. The triple bond is located between the two adjacent carbon atoms. Another non-limiting example of an organic linking group having a —$CR_b$=N— bond is an unsaturated organic linking group created by replacing two adjacent methylene groups in the —$(CH_2)_m$— group with one $CR_b$ group and an N atom. Based on the disclosure herein, a person skill in the art may create an organic linking group having at least an unsaturated bond by replacing at least one pair of adjacent methylene groups in the —$(CH_2)_m$— group, each independently, with an atom or a group selected from the group consisting of N, P, B, C, Si, a $CR_b$ group, an aromatic group having a valence greater than 2, and a heterocyclic group having a valence greater than 2.

In certain embodiments, one or more of R', $R^{2'}$, $R^{3'}$, $R^1$-$R^{12}$, and $K^{21}$-$K^{36}$ are independently substituted by -Cv-Rg or -Cv-Cg groups. In other embodiments, one or more of Q, R', $R^{2'}$, $R^{3'}$ and $R^{11}$-$R^{12}$ are independently substituted by -Cv-Rg or -Cv-Cg groups.

The luminescence quenching compounds having a reactive group (Rg) may comprise a wide variety of organic or inorganic substances that contain or are modified to contain at least one functional group with suitable reactivity toward the Rg group which result in chemical attachment of the reactive group (Rg), represented by -Cv-Rg. In some embodiments, the reactive group (Rg) and functional group are respectively an electrophile and a nucleophile that can react to generate a covalent linkage. The conjugation reaction between the reactive group (Rg) and functional group at the conjugated substance (Cg) results in one or more atoms of the reactive group (Rg) to be incorporated into the linkage, Cv, which attaches the compound with reactive group (Rg) to the conjugated substance (Cg). Some non-limiting examples of the reactive group (Rg) and the respective functional group are listed in Table 1. The tabulation is not meant to be inclusive of chemical reactivity since with the appropriate choice of solvent, co-solvent, stoichiometric ratio, temperature, pressure, reaction time, pH, catalyst and the like, other functional groups can be made to react with the reactive sites disclosed herein whereas the functional groups disclosed herein can be made to react with other reactive sites. Some non-limiting examples of suitable reactive groups (Rg) include acrylamide, acyl azide, acyl halide, nitrile, aldehyde, ketone, alkyl halide, alkyl sulfonate, anhydride, aryl halide, alkyne, alcohol, amine, carboxylic acid, carbodiimide, diazoalkane, epoxide, haloacetamide, hydroxylamine, hydrazine, imido ester, isothiocyanate, maleimide, sulfonate ester or sulfonyl halide.

TABLE 1

| Reactive group (Electrophile) | Functional Group (Nucleophile) | Resulting Linkage |
|---|---|---|
| activated esters (succinimidyl esters) | amines/anilines | amides |
| acrylamides | thiols | thioethers |
| acyl azides | amines/anilines | amides |
| acyl halides | amines/anilines | amides |
| acyl halides | Alcohols/phenols | esters |
| acyl nitriles | alcohols/phenols | esters |
| acyl nitriles | amines/anilines | amides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |

TABLE 1-continued

| Reactive group (Electrophile) | Functional Group (Nucleophile) | Resulting Linkage |
|---|---|---|
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | amides |
| aryl halides | thiols | thiophenols |
| aryl halides | amines | aryl amines |
| alkynes | azides | triazoles |
| alcohols | acid derivatives | esters |
| amines | carboxylic acids | amides |
| amines | halides | alkyl amines |
| amines | aldehydes/ketones | imines |
| carboxylic acids | amines/anilines | amides |
| carboxylic acids | alcohols | esters |
| carboxylic acids | hydrazines | hydrazides |
| carbodiimides | carboxylic acids | N-acylureas or anhydrides |
| diazoalkanes | carboxylic acids | esters |
| epoxides | thiols | thioesters |
| haloacetamides | thiols | thioethers |
| hydroxylamines | aldehydes/ketones | oximes |
| hydrazines | aldehydes/ketones | hydrazones |
| imido esters | amines/anilines | amidines |
| isothiocyanates | amines/anilines | thioureas |
| isothiocyanates | alcohols/phenols | isourethanes |
| maleimides | thiols | thioethers |
| maleimides | amines | amines |
| sulfonate esters | amines/anilines | alkyl amines |
| sulfonate esters | thiols | thioesters |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

The reactive group in the luminescence quenching compounds disclosed herein is useful for the preparation of any conjugated substance that bears a suitable functional group for covalent linkage of the two. Some non-limiting examples of suitable conjugates include conjugates of antigens, steroids, vitamins, drugs, haptens, metabolites, toxins, amino acids, peptides, nucleotides, oligonucleotides, nucleic acid, carbohydrates, lipids, and so on. Choice of the reactive group used to attach the luminescence quenching compounds disclosed herein to the substance to be conjugated typically depends on the functional group on the substance to be conjugated and the type or length of covalent linkage desired. The types of functional groups typically present on the substances include, but are not limited to, amines, thiols, alcohols, phenols, aldehydes, ketones, phosphates, imidazoles, hydrazines, hydroxylamines or a combination of these groups.

In some embodiments, the conjugated substance is additionally conjugated to one or more luminophores, which may be the same or different. In other embodiments, energy transfer from the luminophore to the quenching compound occurs, resulting in significant quenching of luminescence.

The applications of luminescence quenching compounds are well-documented, simply as calorimetric labels for a conjugated substance, or in Fluorescence Resonance Energy Transfer (FRET) technology. Some non-limiting examples of such applications are described in U.S. Pat. No. 6,399,392; and *The Handbook: a Guide to Fluorescent Probes and Labeling Technologies*, 10th Edition, Molecular Probes, 2006, both of which are incorporated herein by reference.

Aromatic Amine Compounds as Fluorogenic Probes for Reactive Oxygen/Nitrogen Species In certain embodiments, the aromatic amine compounds having formula (I) can be used as fluorogenic probe compounds or fluorogenic probe compositions. The fluorogenic probe compounds can be used as fluorogenic probes for reactive oxygen species (ROS) or reactive nitrogen species (RNS) such as $^1O_2$, $O_2^{\cdot-}$, NO, $H_2O_2$, $\cdot OH$, $^-OCl$, $ONOO^-$ and alkylperoxyl radical ($ROO^\cdot$). In some embodiments, Q of formula (I) is a substituted phenyl, which can be cleaved oxidatively by certain ROS or RNS to release of the corresponding L-NHR$^1$ luminophore or fluorophore having strong luminescence or fluorescence properties.

In some embodiments, the fluorogenic probe compounds have formula (X):

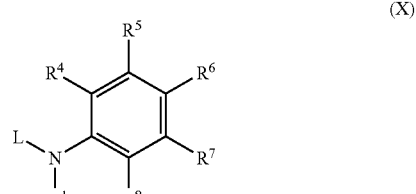

(X)

wherein L, R$^1$ and R$^4$-R$^8$ are as disclosed herein. In some embodiments, L is a fluorophore. In other embodiments, L has one of formulae (II)-(VI), (XX), (XXI), (Va)-(Vd), (VIa)-(VIb), (XXa)-(XXb), (XXIa)-(XXIb), and (a)-(v) disclosed herein.

In certain embodiments, R$^1$ and R$^4$ together or R$^1$ and R$^8$ together form a part of a 5- or 6- or 7-membered cycloalkyl, heterocyclyl, aryl or heteroaryl ring which is fused with the phenyl ring of formula (X).

In some embodiments, each of R$^4$-R$^8$ is H. In some embodiments, each of R$^4$, R$^5$, R$^7$ and R$^8$ is H; and R$^6$ is H, hydroxy, methoxyl, trifluoromethylcarbonylethyl, methyoxycarbonylalkyl or methoxymethoxy.

In general, the fluorogenic probe having formula (X) disclosed herein can react with reactive oxygen species and/or reactive nitrogen species to form tetra-substituted ammonium (XI), which undergo hydrolysis to generate L-derived fluorophore (XII) and a quinone-type by-product (XIII). This general reaction is shown in Scheme 1 below where L, R$^1$ and R$^4$-R$^8$ are as disclosed herein and where R$^{6\prime\prime\prime}$ is derived from R$^6$ by removing a hydrogen or a monovalent group such as alkyl from R$^6$.

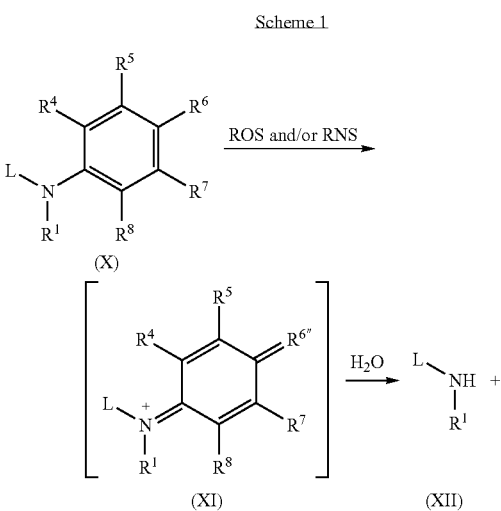

-continued

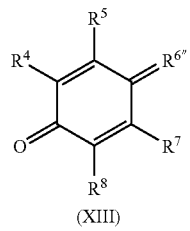

(XIII)

In some embodiments, the fluorogenic probe having formula (X) disclosed herein can react with only one or two or three kinds of reactive oxygen species or reactive nitrogen species to generate fluorophores having formula (X) in substantially higher yields than that of the others. In certain embodiments, the fluorogenic probe having formula (X) can react with peroxynitrite, hypochlorite or hydroxy radical in a higher yield than that of any other ROS and RNS. In other embodiments, the fluorogenic probe having formula (X) reacts with peroxynitrite in a higher yield than that of any other ROS and RNS. In further embodiments, the fluorogenic probe having formula (X) reacts with hypochlorite in higher yields than that of any other ROS and RNS. In still further embodiments, the fluorogenic probe having formula (X) reacts with hydroxy radical in a higher yield than that of any other ROS and RNS.

In certain embodiments, the fluorogenic probe having formula (X) reacts with peroxynitrite, hypochlorite or hydroxy radical in a yield about 5% higher than, about 10% higher than, about 15% higher than, about 20% higher than, about 25% higher than, about 30% higher than, about 35% higher than, about 40% higher than, about 45% higher than, about 50% higher than, about 50% higher than, about 60% higher than, about 65% higher than, about 70% higher than, about 75% higher than, about 80% higher than, about 85% higher than, about 90% higher than or about 95% higher than that of any other ROS and RNS.

The fluorogenic probes provided herein can be used to detect peroxynitrite specifically. In some embodiments, at least one of $R^4$, $R^5$, $R^6$, $R^7$ and $R^8$ of formula (X) of formula (X) is —CH$_2$CH$_2$C(=W)R$^{13}$, wherein R$^{13}$ is an electron-withdrawing group selected from CF$_3$, halogen-substituted lower alkyl (e.g., CF$_n$H$_{3-n}$, where n is 1, 2, or 3), —O—V$^1$, or (C=O)—O—V$^2$, wherein V$^1$ and V$^2$ are groups selected from alkyl, alkenyl, alkynyl, cycloalkyl, cycloalkenyl, cycloalkynyl, aryl, alkaryl or arylalkyl.

In certain embodiments, the fluorogenic probes disclosed herein have formula (XIVa), (XIVb) or (XIVc):

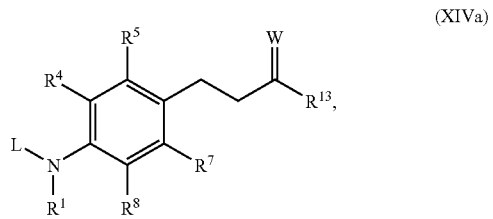

(XIVa)

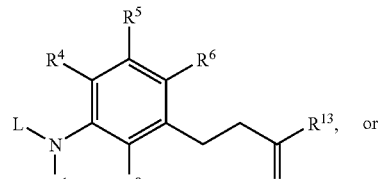

(XIVb)

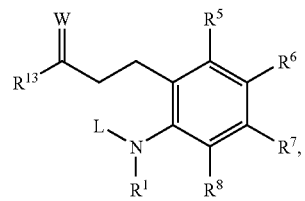

(XIVc)

wherein L, $R^1$, $R^4$, $R^5$, $R^7$, $R^8$ are defined herein;
W is O or S; and
$R^{13}$ is an electron-withdrawing group selected from CF$_3$, halogen-substituted lower alkyl (e.g., CF$_n$H$_{3-n}$, wherein n is 1, 2, or 3), —O—V$^1$, or (C=O)—O—V$^2$, wherein V$^1$ and V$^2$ are groups selected from alkyl, alkenyl, alkynyl, cycloalkyl, cycloalkenyl, cycloalkynyl, aryl, alkaryl or arylalkyl.

In some embodiments, W is O. In other embodiments, $R^{13}$ is CF$_3$. In further embodiments, $R^1$ is methyl. In further embodiments, W is O; $R^{13}$ is CF$_3$; each of $R^4$, $R^5$, $R^7$ and $R^8$ is H; and $R^1$ is methyl.

In certain embodiment, the fluorogenic probes having formula (XIV) reacts with peroxynitrite specifically to form a dioxirane intermediate which subsequently oxidizes the phenyl ring of formula (XIV) to cause the C—N bond cleavage and therefore the release of L derivative (XII) as shown in Scheme 2 below. The L derivative (XII) can emit a strong fluorescence signal when excited.

Scheme 2

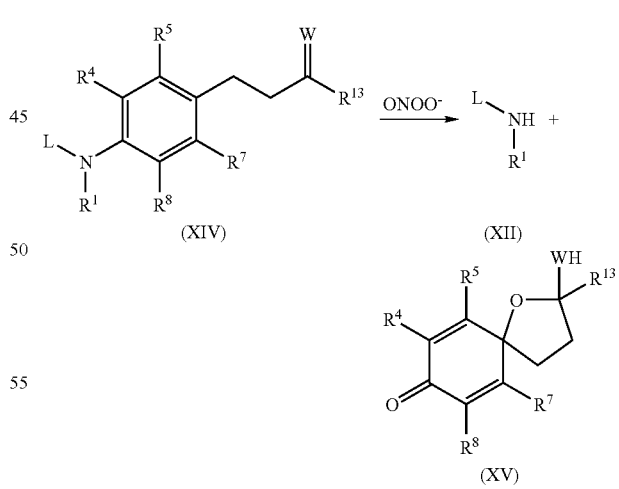

The fluorogenic probes disclosed herein can be used for detecting peroxynitrite with high sensitivity. In some embodiments, at least one of $R^4$, $R^5$, $R^6$, $R^7$ and $R^8$ of the fluorogenic probes of formula (X) is OR$^{14}$ where R$^{14}$ is H, alkyl, alkoxyalkyl, alkanoyl or polyether. In other embodiments, the fluorogenic probes provided herein have formula (XVIa), (XVIb) or (XVIc):

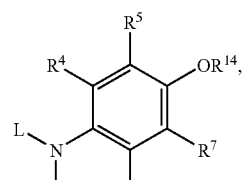
(XVIa)

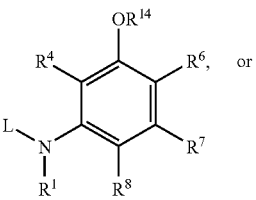
(XVIb), or

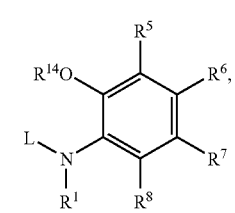
(XVIc)

wherein L, R$^1$, R$^4$, R$^5$, R$^6$, R$^7$ and R$^8$ are as disclosed herein; and R$^{14}$ is H, alkyl, alkoxyalkyl, alkanoyl or polyether.

In some embodiments, R$^5$ and R$^{14}$ together or R$^7$ and R$^{14}$ together form a 5- or 6- or 7-membered cycloalkyl, heterocyclyl, aryl or heteroaryl ring fused with the phenyl ring of formula (XVIa). In other embodiments, R$^4$ and R$^{14}$ together or R$^6$ and R$^{14}$ together form a 5- or 6- or 7-membered cycloalkyl, heterocyclyl, aryl or heteroaryl ring fused with the phenyl ring of formula (XVIb). In further embodiments, R$^5$ and R$^{14}$ together form a 5- or 6- or 7-membered cycloalkyl, heterocyclyl, aryl or heteroaryl ring fused with the phenyl ring of formula (XVIc).

In certain embodiment, each of R$^4$, R$^5$, R$^7$, R$^8$ and R$^{14}$ of formula (XVIa) is H; and R$^1$ is methyl. In other embodiment, each of R$^4$, R$^6$, R$^7$, R$^8$ and R$^{14}$ of formula (XVIb) is H; and R$^1$ is methyl. In further embodiment, each of R$^5$, R$^6$, R$^7$, R$^8$ and R$^{14}$ of formula (XVIc) is H; and R$^1$ is methyl.

In some embodiment, the fluorogenic probes having formula (XVIa) substantially reacts with peroxynitrite specifically to form dioxirane intermediate which subsequently oxidizes the phenyl ring of formula (XVIa) to cause the C—N bond cleavage and therefore the release of L derivative (XII) as shown in Scheme 3 below. The L derivative (XII) can emit a strong fluorescence signal when excited.

Scheme 3

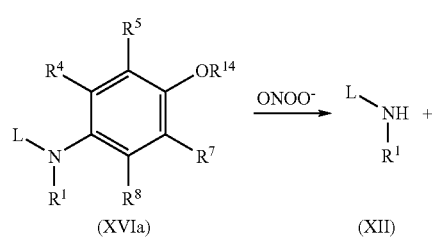

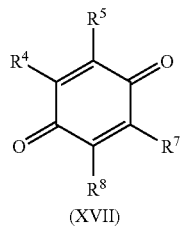
(XVII)

The fluorogenic probes disclosed herein can be used for detecting hypochlorite with high sensitivity. In some embodiments, at least one of R$^4$, R$^5$, R$^6$, R$^7$ and R$^8$ of the fluorogenic probes of formula (X) is NR$^{15}$R$^{16}$ where each of R$^{15}$ and R$^{16}$ is H, alkyl, alkenyl, alkynyl, alkoxyalkyl, alkanoyl, alkenoyl, alkynoyl, cycloalkyl, cycloalkenyl, cycloalkynyl, aryl, alkaryl, arylalkyl, aryloyl, or polyether. In other embodiments, the fluorogenic probes provided herein have formula (XVIIIa), (XVIIIb) or (XVIIIc):

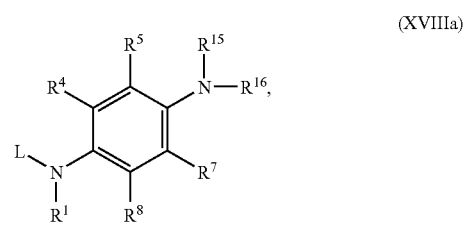
(XVIIIa)

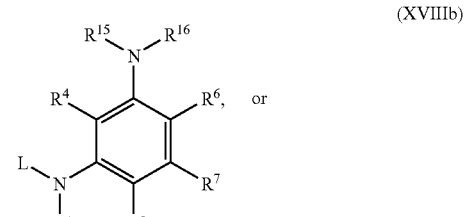
(XVIIIb), or

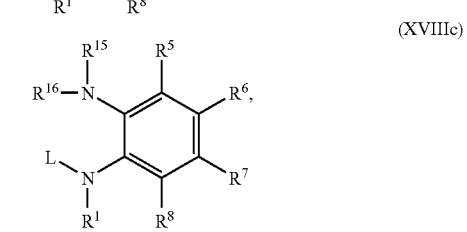
(XVIIIc)

wherein L, R$^1$, R$^4$, R$^5$, R$^6$, R$^7$ and R$^8$ are as disclosed herein; and each of R$^{15}$ and R$^{16}$ is independently H, alkyl, alkenyl, alkynyl, alkoxyalkyl, alkanoyl, alkenoyl, alkynoyl, cycloalkyl, cycloalkenyl, cycloalkynyl, aryl, alkaryl, arylalkyl, aryloyl or polyether.

In some embodiments, R$^5$ and R$^{15}$ together or R$^7$ and R$^{16}$ together form a 5- or 6- or 7-membered cycloalkyl, heterocyclyl, aryl or heteroaryl ring fused with the phenyl ring of formula (XVIIIa). In other embodiments, R$^4$ and R$^{15}$ together or R$^6$ and R$^{16}$ together form a 5- or 6- or 7-membered cycloalkyl, heterocyclyl, aryl or heteroaryl ring fused with the phenyl ring of formula (XVIIIb). In further embodiments, R$^5$ and R$^{15}$ together form a 5- or 6- or 7-membered cycloalkyl, heterocyclyl, aryl or heteroaryl ring fused with the phenyl ring of formula (XVIIIc).

In some embodiment, the fluorogenic probes having formula (XVIIIa) substantially reacts with hypochlorite specifically to cause the C—N bond cleavage and therefore the release of L derivative (XII) as shown in Scheme 4 below. The L derivative (XII) can emit a strong fluorescence signal when excited.

Scheme 4

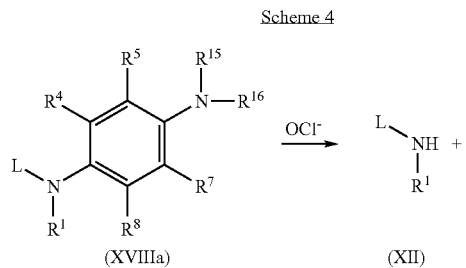

(XVIIIa)        (XII)

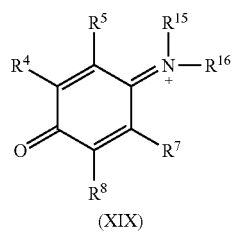

(XIX)

In certain embodiment, each of $R^4$, $R^5$, $R^7$ and $R^8$ of formula (XVIIIa) is H; $R^1$ is methyl; and each of $R^{15}$ and $R^{16}$ is independently H or methyl. In certain embodiment, each of $R^4$, $R^6$, $R^7$ and $R^8$ of formula (XVIIIb) is H; $R^1$ is methyl; and each of $R^{15}$ and $R^{16}$ is independently H or methyl. In certain embodiment, each of $R^5$, $R^6$, $R^7$ and $R^8$ of formula (XVIIIc) is H; $R^1$ is methyl; and each of $R^{15}$ and $R^{16}$ is independently H or methyl.

The fluorogenic probes for reactive oxygen species and/or reactive nitrogen species disclosed herein comprise rhodol, rhodamine, resorufin, and naphthofluorescein fluorophores. In some embodiments, the compounds or peroxynitrite probes or hypochlorite probes disclosed herein are substantially non-fluorescent. In other embodiments, the compounds or peroxynitrite probes or hypochlorite probes disclosed herein can efficiently react with peroxynitrite or hypochlorite under physiological conditions to give a strong fluorescent signal. In further embodiments, the amount of peroxynitrite or hypochlorite can be determined with very high specificity and selectivity by measuring the fluorescent signal of the oxidized probes.

In some embodiment, L of the fluorogenic probes of formula (I) can be any fluorophore known to a skilled artisan. In other embodiments, L is derived from rhodol, rhodamine, resorufin, naphthofluorescein, seminaphthofluorescein or a derivative thereof.

In some embodiments, L is derived from a rhodol, rhodamine or derivative thereof, wherein L has formula (Vd):

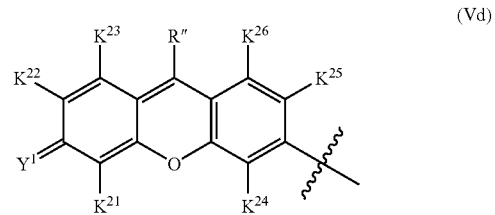

(Vd)

wherein $Y^1$ and $K^{21}$-$K^{26}$ are as disclosed herein.

In some embodiments, R" of formula (Vd) is a substituted or unsubstituted phenyl having formula (VII):

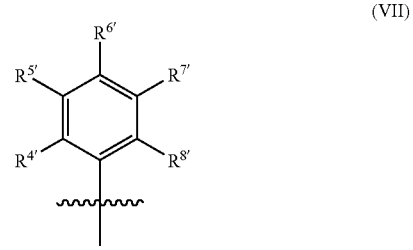

(VII)

wherein $R^{4'}$, $R^{5'}$, $R^{6'}$, $R^{7'}$ and $R^{8'}$ are as disclosed herein. In certain embodiments, one or more of $R^{4'}$, $R^{5'}$, $R^{6'}$, $R^{7'}$ and $R^{8'}$ of formula (VII) is halogenated alkyl. In other embodiments, one or more of $R^{4'}$, $R^{5'}$, $R^{6'}$, $R^{7'}$ and $R^{8'}$ of formula (VII) is chloromethyl, which can react with sulfide groups in cells to keep the fluorogenic probes inside the cells and from leakage. In other embodiments, at least one of $R^{4'}$, $R^{5'}$, $R^{6'}$, $R^{7'}$ and $R^{8'}$ of formula (VII) is linked with a cell organelle localization moiety such as triphenylphosphonium. In further embodiments, each of $R^{4'}$, $R^{5'}$, $R^{6'}$ and $R^{7'}$ of formula (VII) is H; and $R^{8'}$ is a —COOH group, methyl, or methoxy.

In certain embodiments, L is derived from a resorufin or a derivative thereof and has formula (Va):

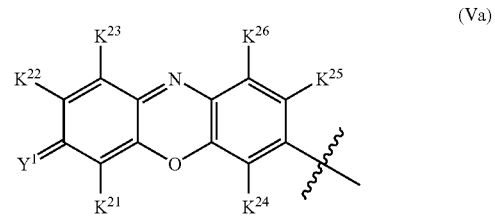

(Va)

wherein $Y^1$ and $K^{21}$-$K^{26}$ are as disclosed herein. In some embodiments, $Y^1$ is O. In other embodiments, $Y^1$ is $N^+R^{2'}R^{3'}$. In further embodiments, each of $K^{21}$-$K^{26}$ of formula (Va) is independently H, halo, alkyl, halogenated alkyl, heteroalkyl, alkenyl, alkynyl, aryl, aralkyl, alkaryl, heterocyclyl, cycloalkyl, cycloalkenyl, cycloalkynyl, hydroxyalkyl, aminoalkyl, amino, alkylamino, arylamino, dialkylamino, alkylarylamino, diarylamino, acylamino, hydroxy, thio, thioalkyl, alkoxy, alkylthio, alkoxyalkyl, aryloxy, arylalkoxy, acyloxy, cyano, nitro, sulfhydryl, carbamoyl, trifluoromethyl, phenoxy, benzyloxy, sulfonyl, phosphonyl, sulfonate ester or phosphate ester. In other embodiments, each of $K^{21}$-$K^{26}$ is H. In other embodiments, each of $K^{22}$ and $K^{25}$ is independently chlorine or fluorine.

In some embodiments, L is derived from a naphthofluorescein or a derivative thereof and has formula (VI):

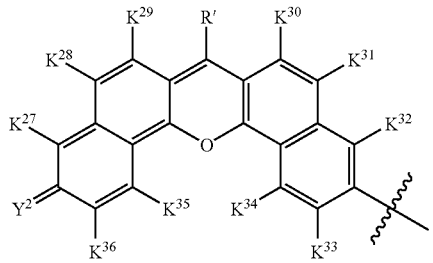

(VI)

wherein $Y^2$ and $K^{27}$-$K^{36}$ are as disclosed herein. In other embodiments, $Y^2$ is $N^+R^{2'}R^{3'}$ wherein $R^{2'}$ and $R^{3'}$ are as disclosed herein. In further embodiments, $Y^2$ is O.

In some embodiments, R' is a substituted or unsubstituted phenyl having formula (VII):

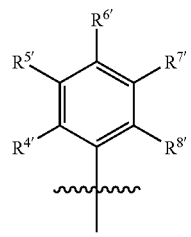

(VII)

wherein $R^{4'}$, $R^{5'}$, $R^{6'}$, $R^{7'}$ and $R^{8'}$ are as disclosed herein. In some embodiments, $R^{4'}$ or $R^{8'}$ of formula (VII) is a —COOH group. In further embodiments, each of $R^{4'}$, $R^{5'}$, $R^{6'}$ and $R^{7'}$ of formula (VII) is H; and $R^{8'}$ is a —COOH group, methyl or methoxy.

In some embodiments, L is derived from a seminaphthofluorescein or a derivative thereof and has formula (XX) or (XXI):

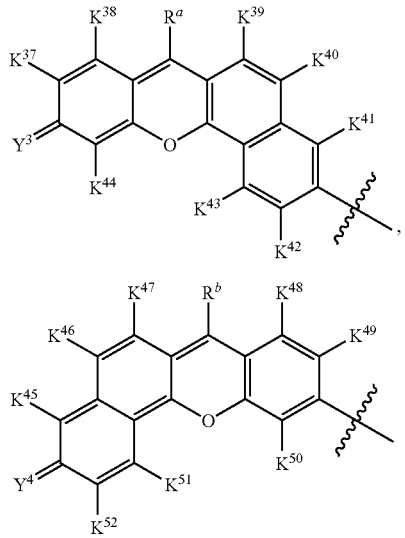

(XX)

, (XXI)

wherein $Y^3$, $Y^4$ and $K^{37}$-$K^{52}$ are as disclosed herein. In other embodiments, each of $Y^3$ and $Y^4$ is independently $N^+R^{2'}R^{3'}$ wherein $R^{2'}$ and $R^{3'}$ are as disclosed herein. In further embodiments, each of $Y^3$ and $Y^4$ is O. In some embodiments, $K^{37}$ is chlorine or fluorine. In some embodiments, at least one of $K^{45}$ and $K^{52}$ is chlorine or fluorine.

In some embodiments, $R^a$ or $R^b$ is a substituted or unsubstituted phenyl having formula (VII):

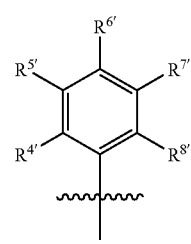

(VII)

wherein $R^{4'}$, $R^{5'}$, $R^{6'}$, $R^{7'}$ and $R^{8'}$ are as disclosed herein. In some embodiments, $R^{4'}$ or $R^{8'}$ of formula (VII) is a —COOH group. In further embodiments, each of $R^{4'}$, $R^{5'}$, $R^{6'}$ and $R^{7'}$ of formula (VII) is H; and $R^{8'}$ is a —COOH group, methyl or methoxy.

In certain embodiments, the fluorogenic probe compositions can be used for measuring, detecting or screening peroxynitrite, wherein the fluorogenic probe compositions comprise the aromatic amine compound disclosed herein. In certain embodiments, the aromatic amine compound is Compound (10), Compound (12) or Compound (30):

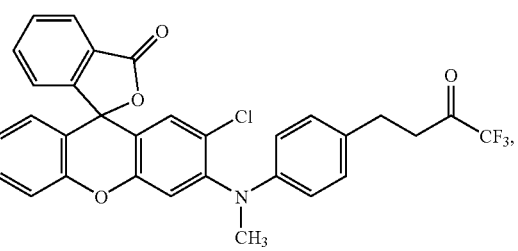

(10)

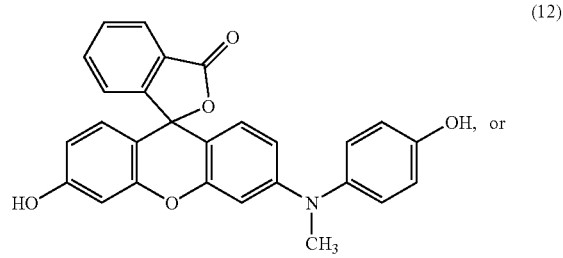

(12)

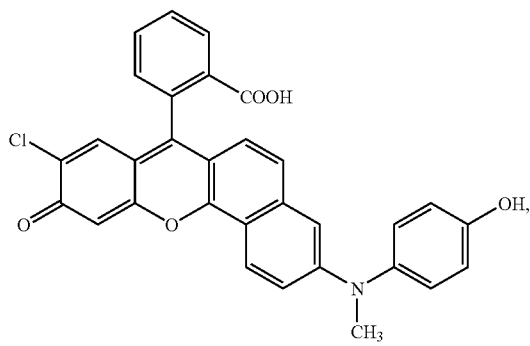

(30)

or a tautomer thereof, or a combination thereof.

In some embodiments, the fluorogenic probe compositions can be used for measuring, detecting or screening hypochlorite, wherein the fluorogenic probe compositions comprise the aromatic amine compound disclosed herein. In certain embodiments, the aromatic amine compound is Compound (14):

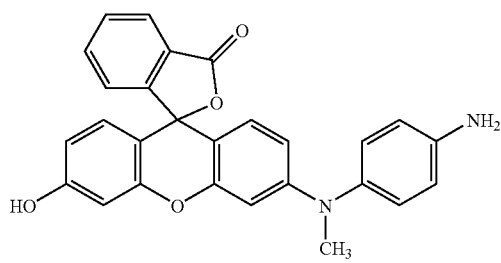

(14)

or a tautomer thereof.

In certain embodiments, the fluorogenic probe compositions disclosed herein further comprise a solvent, an acid, a base, a buffer solution or a combination thereof.

Figure 2:
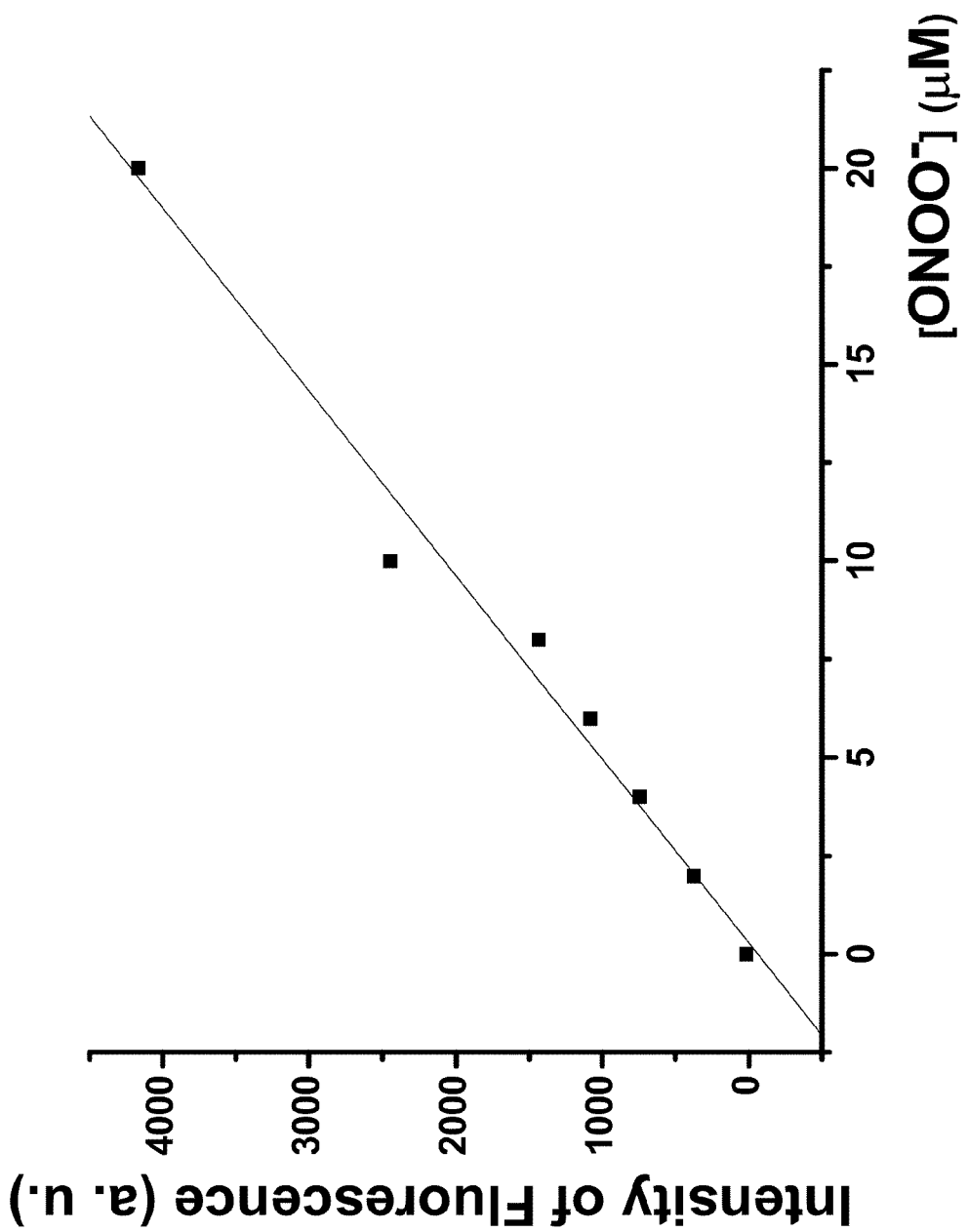
FIG. 2 depicts a linear correlation between fluorescence intensity of 10 μM of Compound 10 and the concentration of $ONOO^-$ measured at 540 nm.
Figure 3:
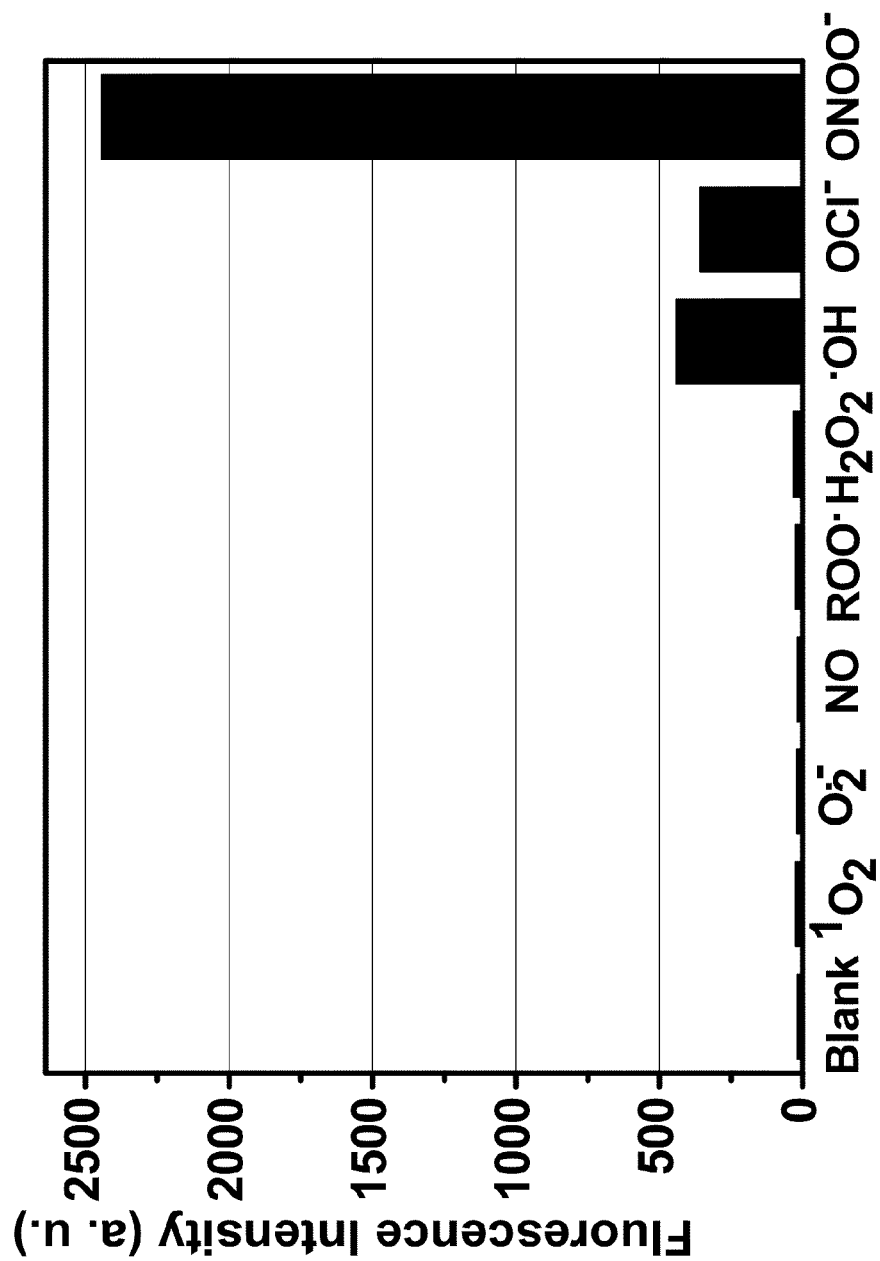
FIG. 3 depicts the fluorescence intensity of 10 μM of Compound 10 in various ROS/RNS generating systems at 25° C. for 30 minutes measured at 540 nm. The concentration of $^1O_2$, $O_2^{\cdot-}$, NO, ROO. and $H_2O_2$ concentration was 100 μM. The concentration of .OH, $^-OCl$ and $ONOO^-$ concentration was 10 μM.

In some embodiments, the aromatic amine compound is Compound (10) which reacts with ONOO⁻ to form Compound (11) with strong fluorescent properties as shown in Scheme 5 below. The fluorescence spectra showing fluorescence intensities of Compound 10 in response to different concentrations of ONOO⁻ at different wavelengths are shown in FIGS. 1-2. The fluorescence intensities of Compound 10 in response to different ROS and RNS is shown in FIG. 3.

Scheme 5

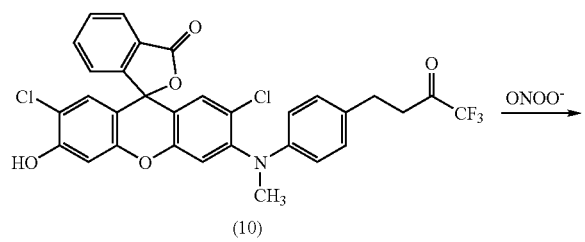

(10)

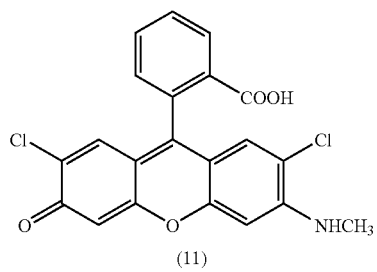

(11)

Figure 4:
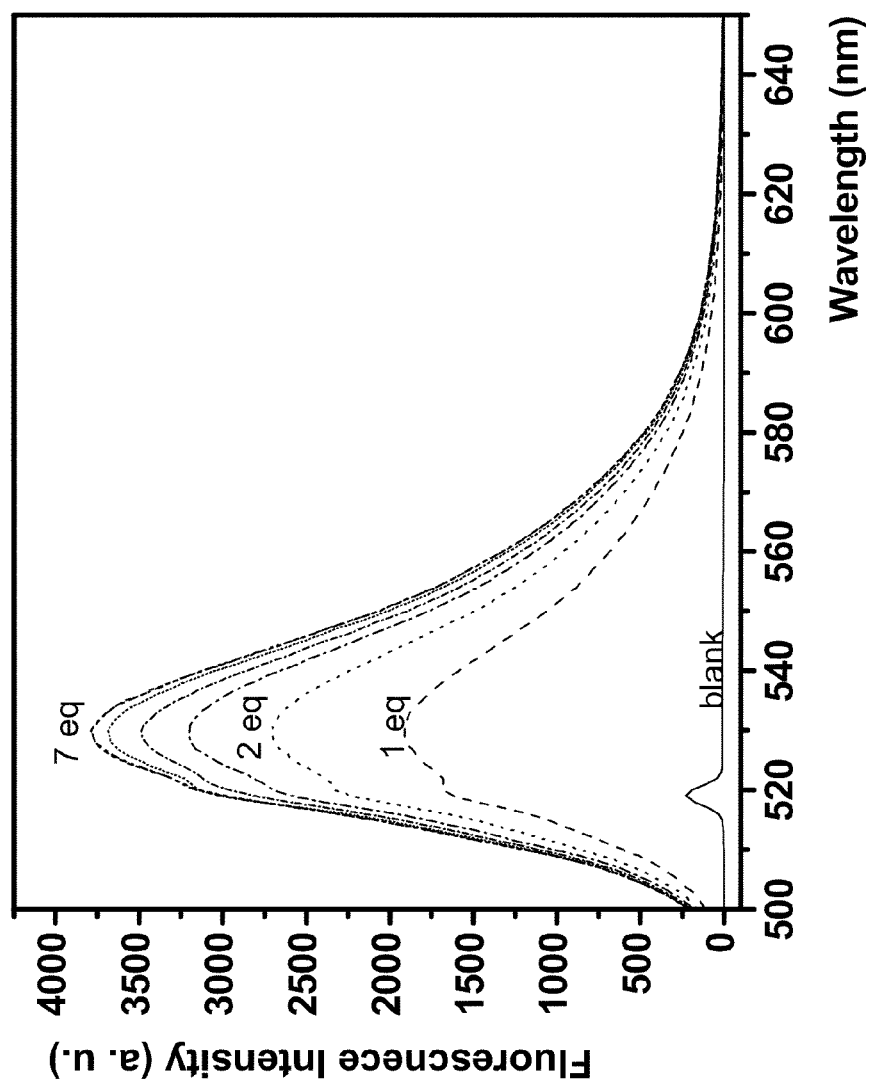
FIG. 4 depicts fluorescence spectra showing fluorescence intensities of 1 μM of Compound 12 in response to different concentrations of $ONOO^-$ at different wavelengths. The spectra were acquired in 0.1 M potassium phosphate buffer at pH 7.4 where 0.1% DMF was used as a cosolvent.
Figure 5:
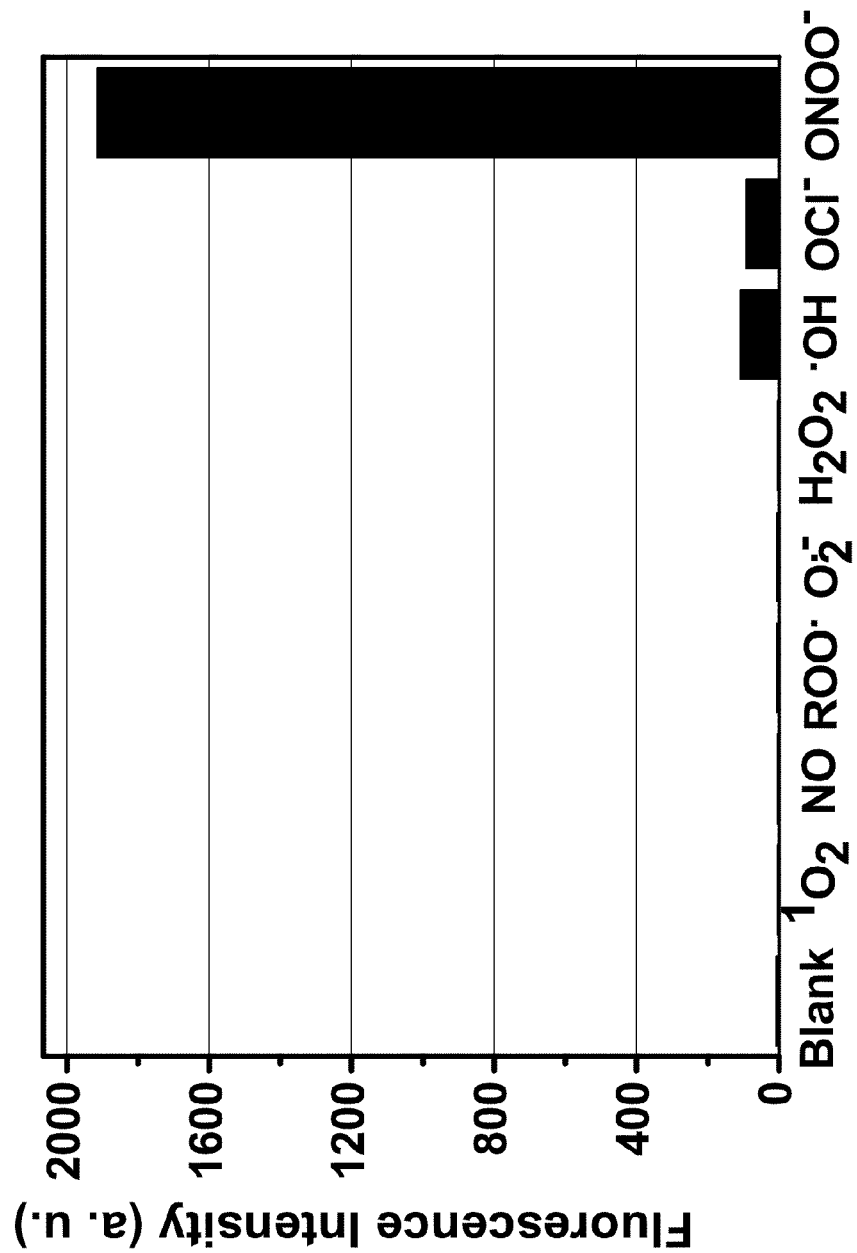
FIG. 5 depicts the fluorescence intensity of 1 μM of Compound 12 in various ROS/RNS generating systems at 25° C. for 30 minutes measured at 530 nm. The concentration of each of $^1O_2$, $O_2^{\cdot-}$, NO, ROO. and $H_2O_2$ was 10 μM. The concentration each of .OH, $^-OCl$ and $ONOO^-$ was 1 μM.

In other embodiments, the aromatic amine compound is Compound (12) which reacts with ONOO⁻ to form Compound (13) with strong fluorescent properties as shown in Scheme 6 below. The fluorescence spectra showing fluorescence intensities of Compound 12 in response to different concentrations of ONOO⁻ at different wavelengths are shown in FIG. 4. The fluorescence intensities of Compound 12 in response to different ROS and RNS is shown in FIG. 5.

Scheme 6

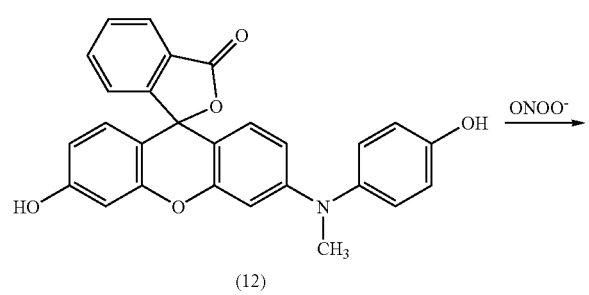

(12)

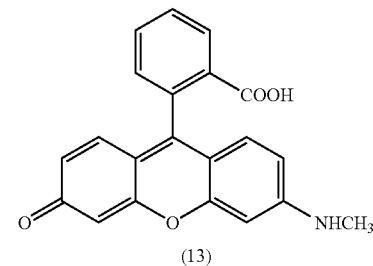

(13)

Figure 6:
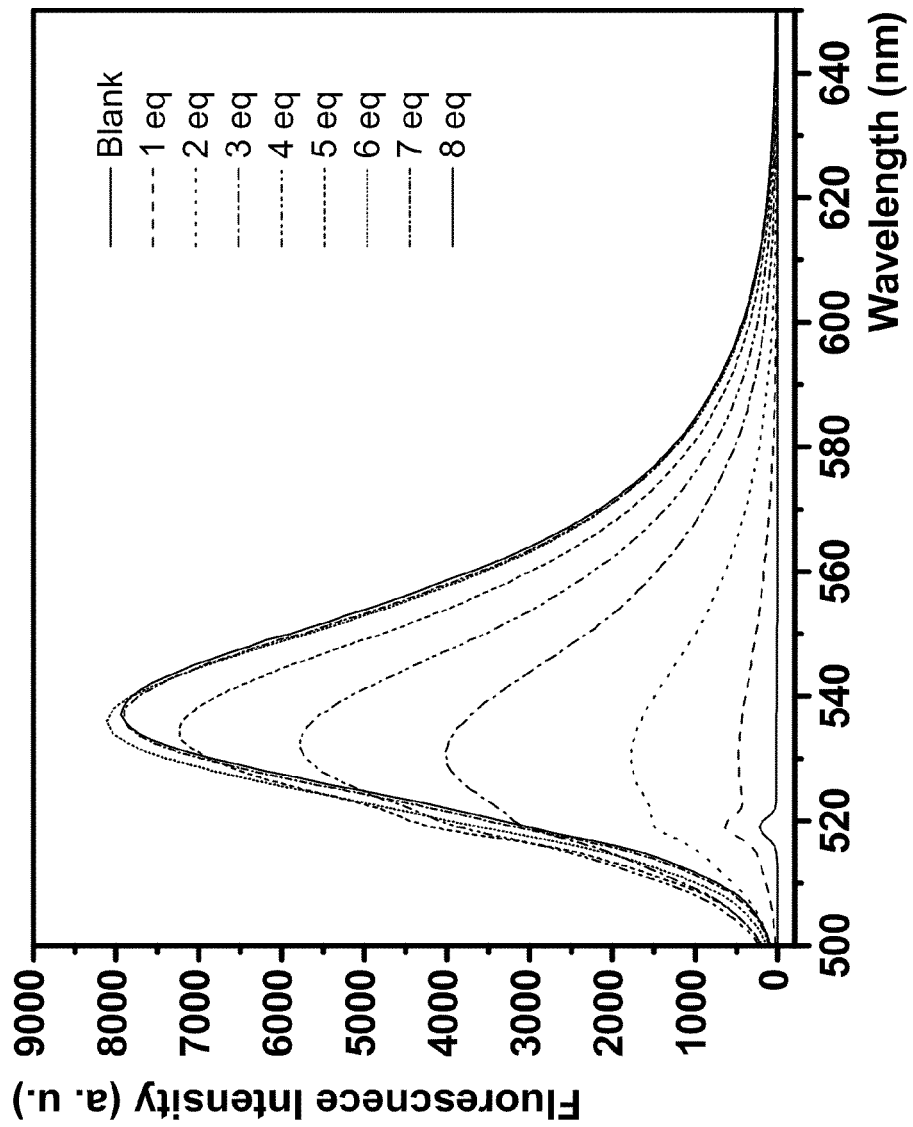
FIG. 6 depicts fluorescence spectra showing fluorescence intensities of 1 μM of Compound 14 in response to different concentrations of $^-OCl$ at different wavelengths. The spectra were acquired in 0.1 M potassium phosphate buffer at pH 7.4 where 0.1% DMF was used as a cosolvent.
Figure 7:
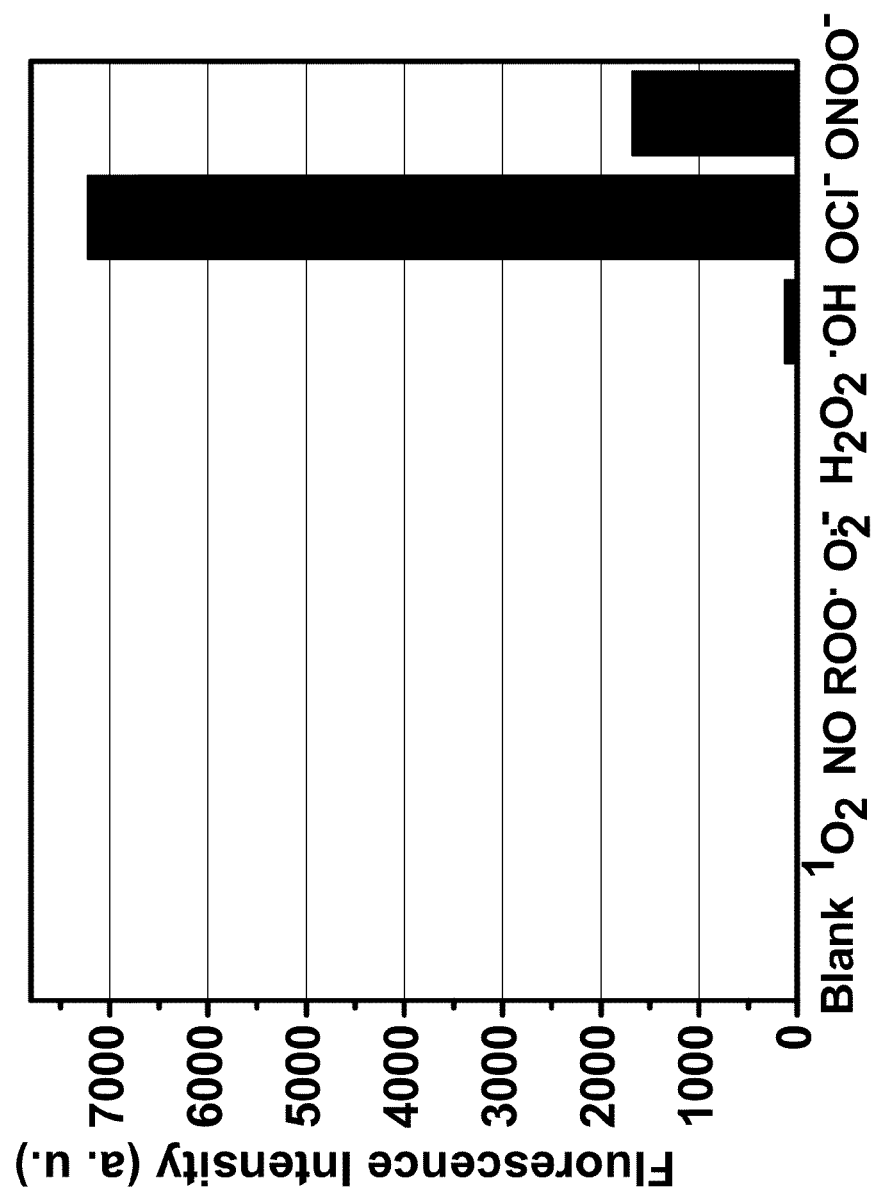
FIG. 7 depicts the fluorescence intensity of 1 μM of Compound 14 in various ROS/RNS generating systems at 25° C. for 30 minutes measured at 530 nm. The concentration of each of $^1O_2$, $O_2^{\cdot-}$, NO, ROO., $H_2O_2$, .OH, $^-OCl$ and $ONOO^-$ was 5 μM.
Figure 8:
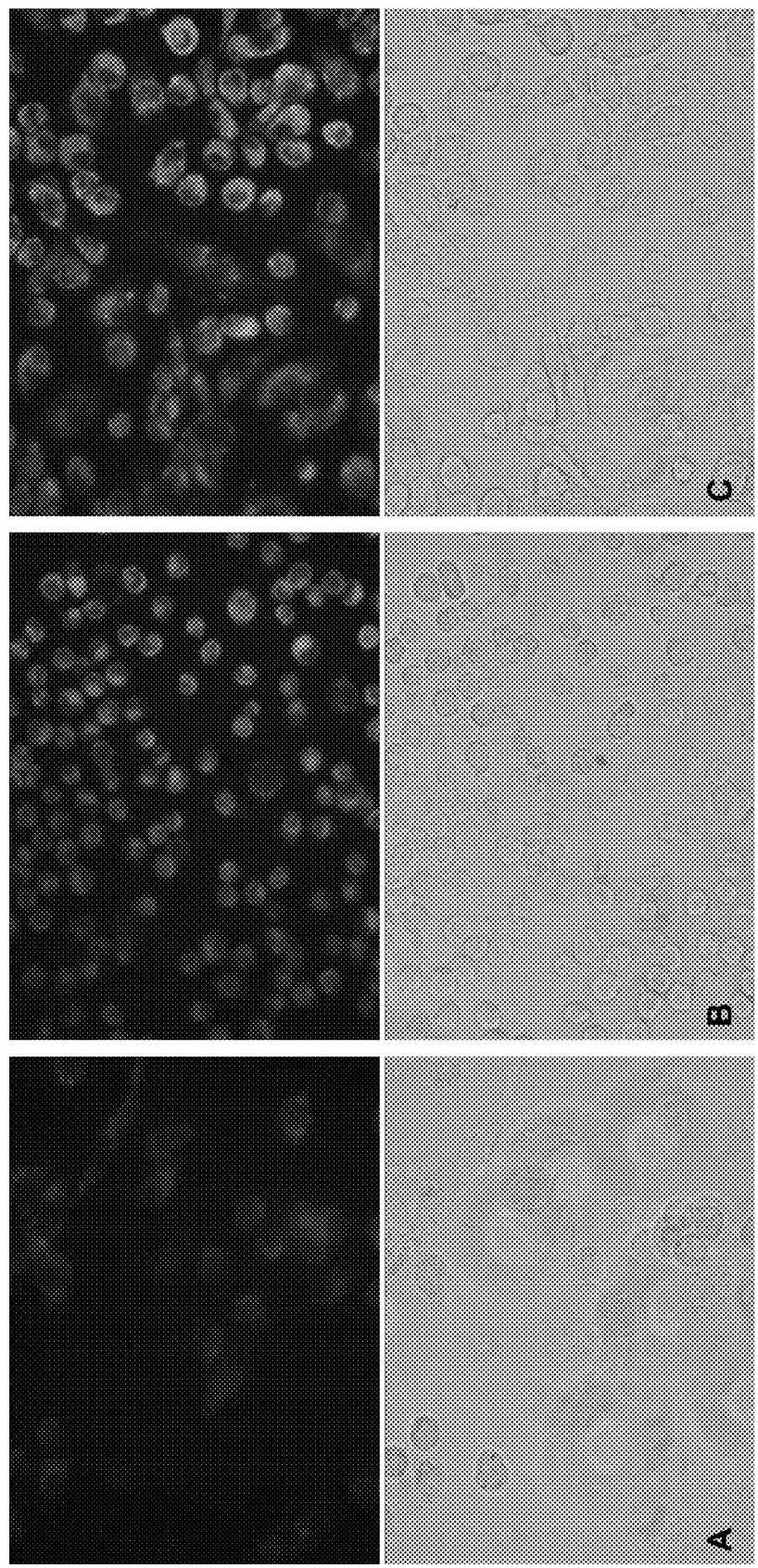
FIG. 8 shows fluorescent microscopy results of Murine J744.1 macrophages under different stimulation conditions. The macrophage cells were incubated with Compound 10 at a concentration of 20 μM. The macrophages in (A) were the Control. The macrophages in (B) were stimulated with LPS and IFN-γ for 4 hours. The macrophages in (C) were stimulated with LPS and IFN-γ for 4 hours, followed by further stimulation with PMA for 0.5 hours.
Figure 9:
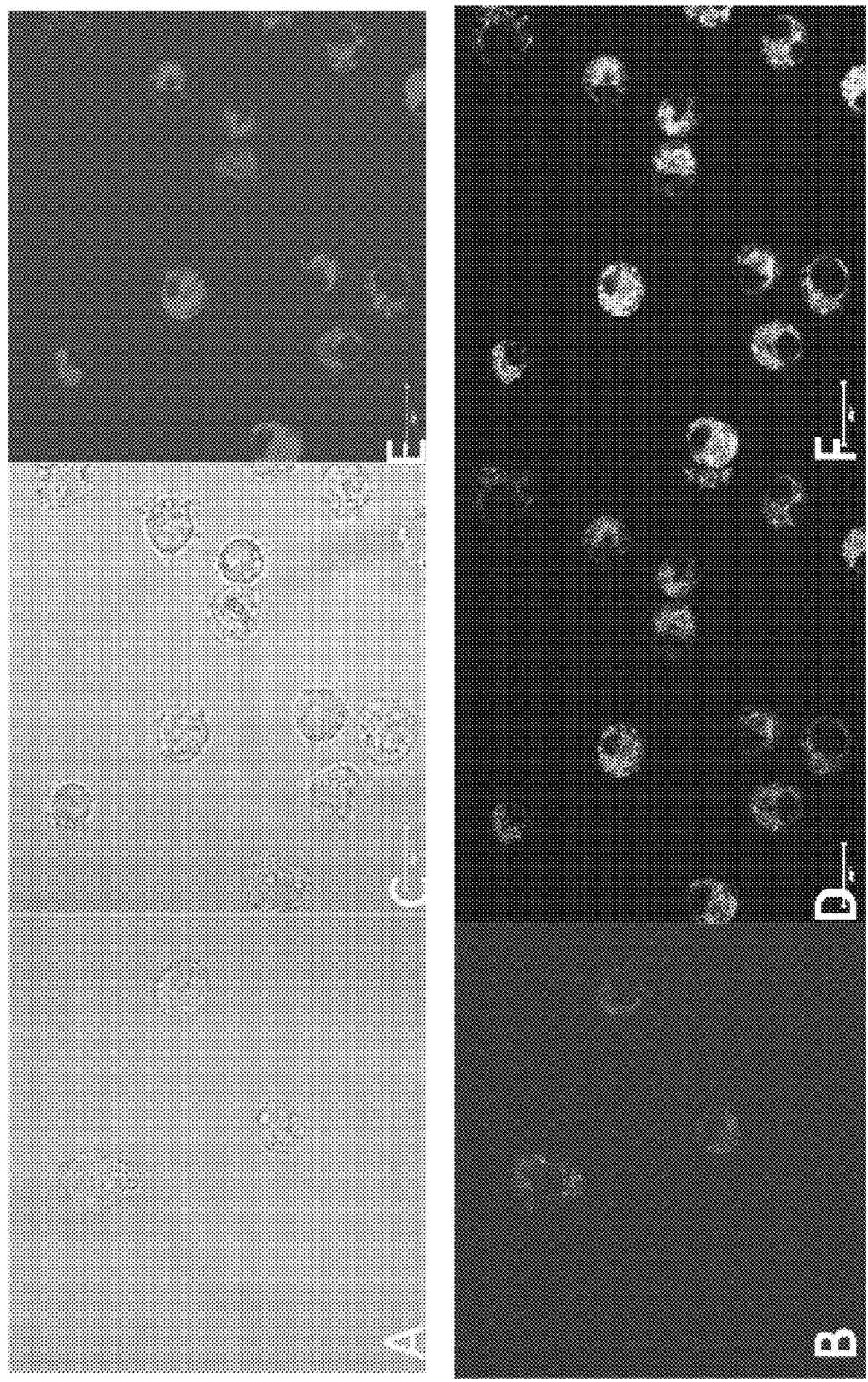
FIG. 9 shows fluorescent microscopy results of Murine J744.1 macrophages under different stimulation conditions. The macrophage cells were incubated with Compound 12 and MitoTracker Red CMXRos (purchased from Invitrogen) at concentrations of 20 μM. The macrophages in (A)-(B) were the control. The macrophages in (C)-(F) were stimulated with LPS.
Figure 10:
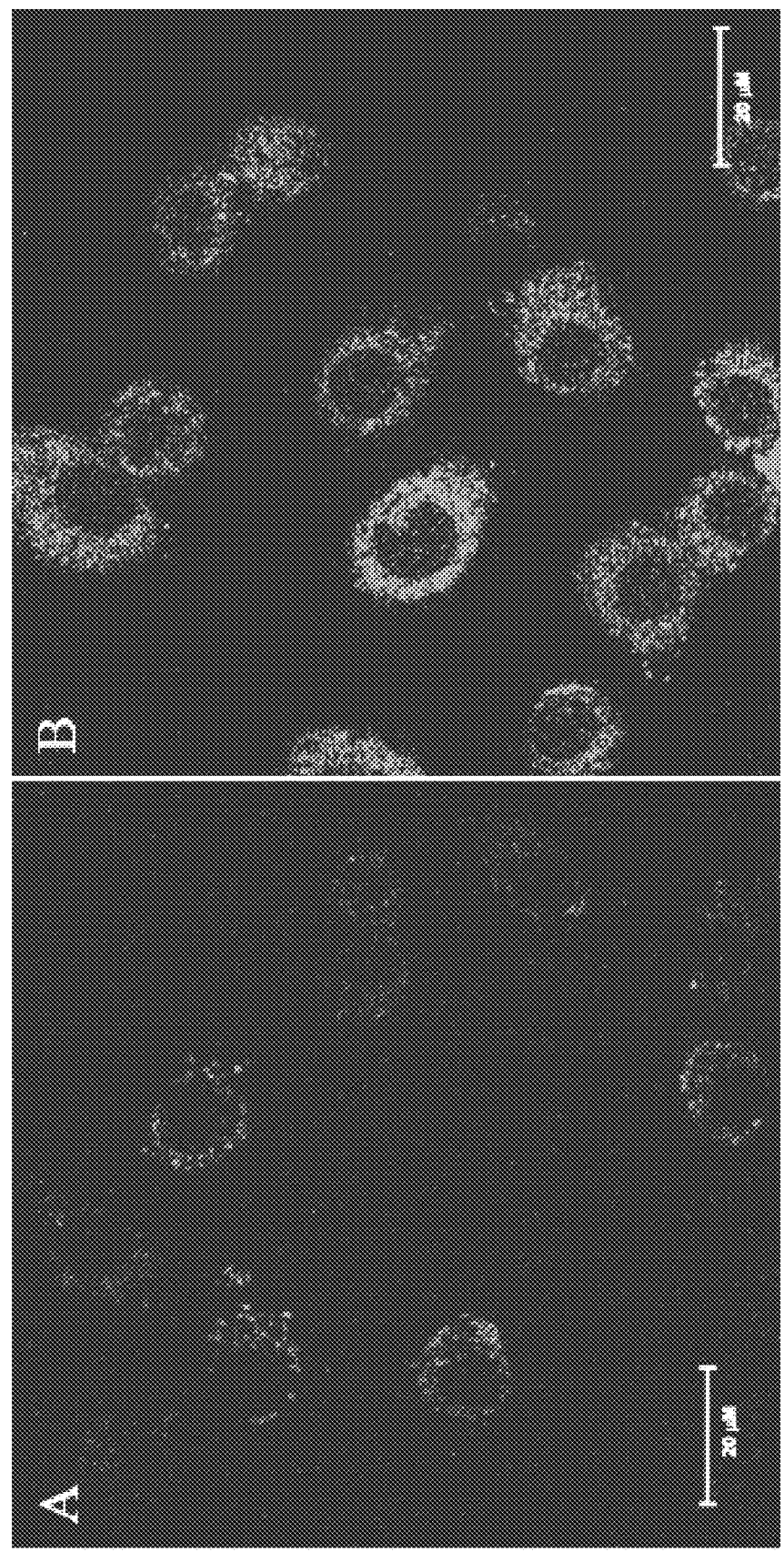
FIG. 10 shows two-photon fluorescent microscopy results of Murine J744.1 macrophages under stimulation conditions. The macrophage cells were incubated with Compound 12a at a concentration of 20 μM. The macrophages in (A) were the control. The macrophages in (B) were stimulated with LPS for 4 hours.

In further embodiments, the aromatic amine compound is Compound (14) which reacts with OCl⁻ to form Compound (13) with strong fluorescent properties as shown in Scheme 7 below. The fluorescence spectra showing fluorescence intensities of Compound 14 in response to different concentrations of OCl⁻ at different wavelengths are shown in FIG. 6. The fluorescence intensities of Compound 14 in response to different ROS and RNS is shown in FIG. 7.

Scheme 7

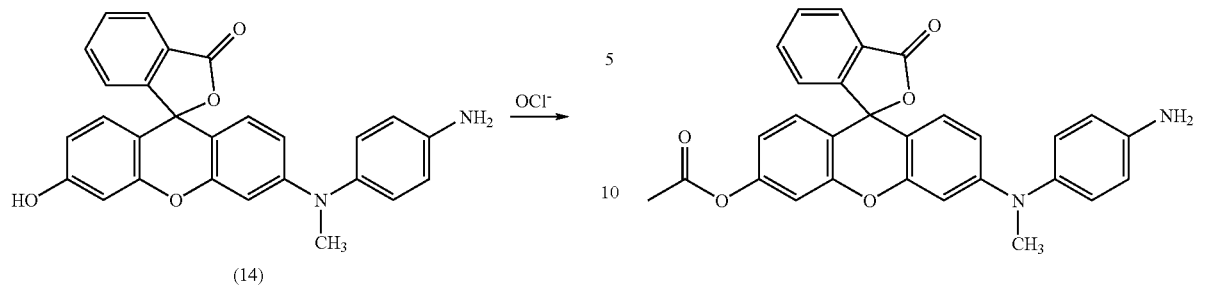

(14)

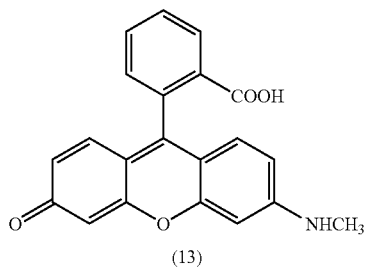

(13)

In some embodiments, the fluorogenic probe compositions for measuring, detecting or screening peroxynitrite comprise Compound (22), Compound (12a) or a combination thereof. Each of Compound (22) and Compound (12a) is an ester derivative of Compound (10) and Compound (12) respectively. In certain embodiments, Compound (22) and Compound (12a) provide desirable cell membrane permeability.

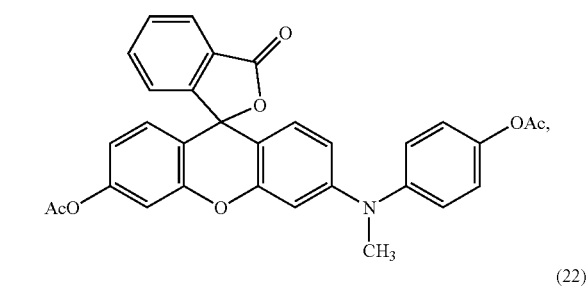

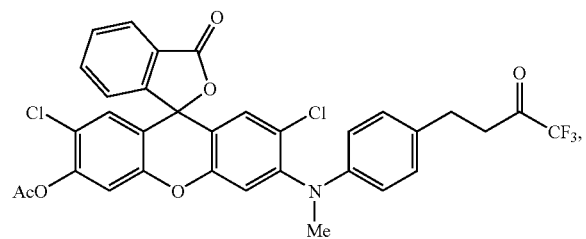

In some embodiments, the fluorogenic probe compositions for measuring, detecting or screening hypochlorous acid/hypochloride comprise Compound (14a), which is an ester derivative of Compound (14). Compound (14a) provides desirable cell membrane permeability.

In certain embodiments, the fluorogenic probe compositions disclosed herein comprise an acetate or acetoxymethyl (AM) ester derivative of fluorogenic probe compounds disclosed herein. The neutral forms of these fluorogenic probe compounds are advantageous for cell membrane permeability.

In certain embodiments, the fluorogenic probe compositions disclosed herein further comprise a solvent, an acid, a base, a buffer solution or a combination thereof.

Also provided herein are reagent compositions for measuring directly or indirectly peroxynitrite or hypochlorite in chemical or biological samples such as microorganism, or a cell or tissue from animals. The reagent composition comprises the fluorogenic probe disclosed herein. In some embodiments, the reagent composition further comprises a solvent, an acid, a base, a buffer solution or a combination thereof a base, a buffer solution or a combination thereof.

Also provided herein are methods for measuring peroxynitrite or hypochlorite in a sample. In some embodiments, the methods comprise the steps of (a) contacting a fluorogenic probe disclosed herein with the sample to form a fluorescent compound; and (b) measuring fluorescence properties of the fluorescent compound. In some embodiments, the fluorescence properties are measured with methods disclosed herein or any method known to a person skilled in the art. In other embodiments, the sample is a chemical sample or biological sample. In further embodiments, the sample is a biological sample comprising a microorganism, or a cell or tissue from animals.

Also provided herein are high-throughput screening fluorescent methods for detecting peroxynitrite or hypochlorite in samples. In some embodiments, the high-throughput screening fluorescent methods comprise the steps of (a) contacting a fluorogenic probe disclosed herein with the samples to form one or more fluorescent compounds; and (b) measuring fluorescence properties of the fluorescent compounds. In other embodiments, the fluorescence properties are measured with methods disclosed herein or any method known to a person skilled in the art.

Also provided herein are high-throughput methods for screening one or more target compounds that can increase or decrease the level of peroxynitrite or hypochlorite. In some embodiments, the high-throughput methods comprise the steps of (a) contacting a fluorogenic probe disclosed herein with the target compounds to form one or more fluorescent compounds; and (b) measuring fluorescence properties of the fluorescent compounds to determine the target compounds quantitatively or qualitatively. In other embodiments, the fluorescence properties are measured with methods disclosed herein or any method known to a person skilled in the art.

In some embodiments, informatics systems can be used and implemented in the high-throughput methods disclosed herein. In other embodiments, the informatics systems provide the software control of the physical devices used in the high-throughput method. In other embodiments, the informatics systems organize electronic data generated by the high-throughput methods. In further embodiments, the informatics systems store electronic data generated by the high-throughput methods.

General Synthetic Procedures

The aromatic amine compounds or fluorogenic probes disclosed herein may be made by one skilled in the art with known organic syntheses as well as various general or specific synthetic procedures disclosed herein.

Generally, the key steps for the synthesis of the aromatic amine compounds include a hydroxy activation step, generally using a triflate, and subsequent amination step as shown in Scheme 8 below.

Scheme 8

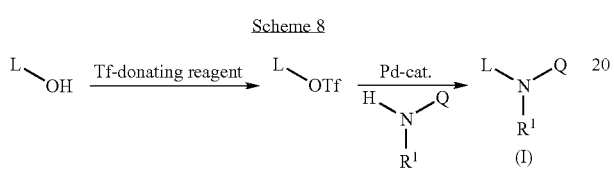

where L, $R^1$, and Q are as disclosed herein; Tf is triflyl; Pd-cat. is a palladium-ligand catalysis system for C—N bond formation. First, the OH group of the luminophore (L-OH) was activated by reacting with a triflyl-donating reagent, such as triflic anhydride, to form a triflate group. Then the triflate group subsequently underwent cross-coupling reaction with an amine having formula $HNR^1Q$ in the presence of a catalyst, such as a Pd catalyst, to form the aromatic amine compound of formula (I).

Some non-limiting examples of suitable synthetic method can be found in U.S. Patent Application No. 61/041923, filed Apr. 3, 2008, which is incorporated herein by reference.

EXAMPLES

The following Examples 1-13 and FIGS. 1-11 are detailed descriptions of the methods of making and using the subject compounds disclosed in this invention. The detailed disclosure falls within the scope of, and serve to exemplify, the synthetic schemes or procedures disclosed herein which form part of this disclosure. These examples, figures and schemes are presented for illustrative purposes only and are not intended to limit the scope of this disclosure.

Example 1

Synthetic Scheme for Compounds 1-4

Synthesis of Compound 8

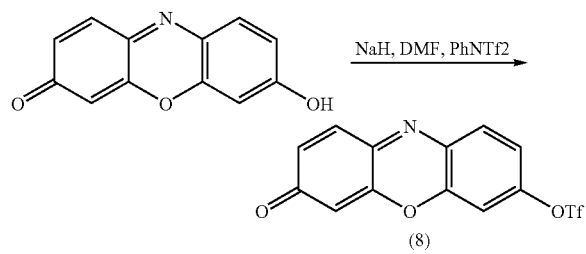

To a solution of resorufin (2.13 g, 10 mmol) in 50 mL of anhydrous dimethylforamide was added sodium hydride (437 mg, 11 mmol, 60% dispersion in mineral oil) at 0° C. After being stirred at 0° C. for half an hour, to the solution was then added N-phenyl bis-trifluoromethane sulfonimde (4.3 g, 12 mmol). The resulting mixture was stirred at room temperature overnight and then quenched with water. After that 1N of hydrochloric acid was added to the mixture to acidify the solution to pH 2. Ethyl acetate was then added. The organic layer was separated and washed with brine, dried over anhydrous sodium sulfate and evaporated in vacuo. The residue was purified by silica gel column chromatography to give Compound 8.

Synthesis of Compound 1

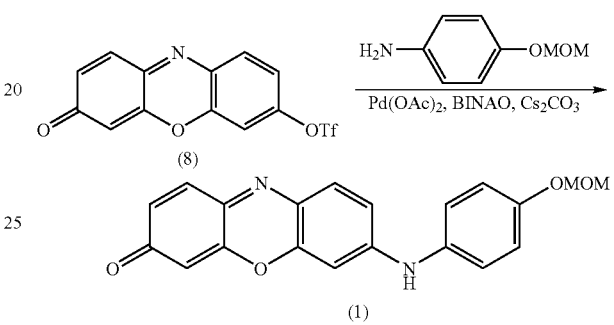

An oven-dried Schlenk tube was charged with palladium (II) acetate (2 mg, 1% mmol), 2,2'-bis(diphenylphosphino)-1,1'-binaphthyl (BINAP) (9 mg, 1.5% mmol) and cesium carbonate ($Cs_2CO_3$) (91 mg, 0.28 mmol), and flushed with argon gas for 5 minutes. A solution of Compound 8 (69 mg, 0.2 mmol) and 4-(methoxymethoxy)aniline (37 mg, 0.24 mmol) in toluene (2 mL) was added, and the resulting mixture was first stirred under argon gas at room temperature for 30 minutes and then at 100° C. for 20 hours. The reaction mixture was allowed to cool to room temperature, diluted with dichloromethane and filtered through a pad of Celite. The filter cake was washed three times with 10 mL of dichloromethane. The filtrate was then concentrated and the residue was purified by silica gel column chromatography to give Compound 1.

Synthesis of Compound 2

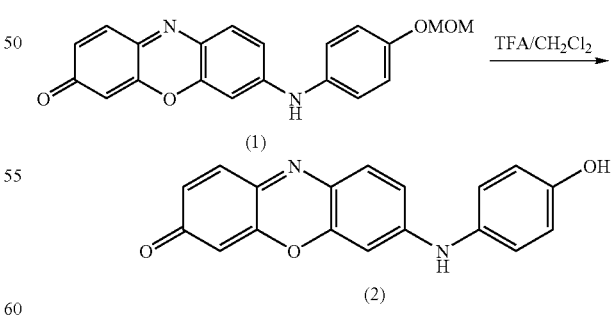

To a solution of Compound 1 (35 mg, 0.1 mmol) in dry dichloromethane (1 mL) was added trifluoroacetic acid (1 mL) dropwise at 0° C. The resulting solution was stirred at room temperature until the thin layer chromatography indicated that all starting material was consumed. The mixture was then concentrated under vacuo and azeotroped with toluene three times. The residue was purified by silica gel column chromatography to give Compound 2.

Synthesis of Compounds 3 and 4

Compounds 3 and 4 can be synthesized in a similar scheme as shown for Compounds 1 and 2, including a triflation reaction and a following amination reaction.

Example 2

Synthetic Scheme for Compounds 5-7

Synthesis of Compound 9

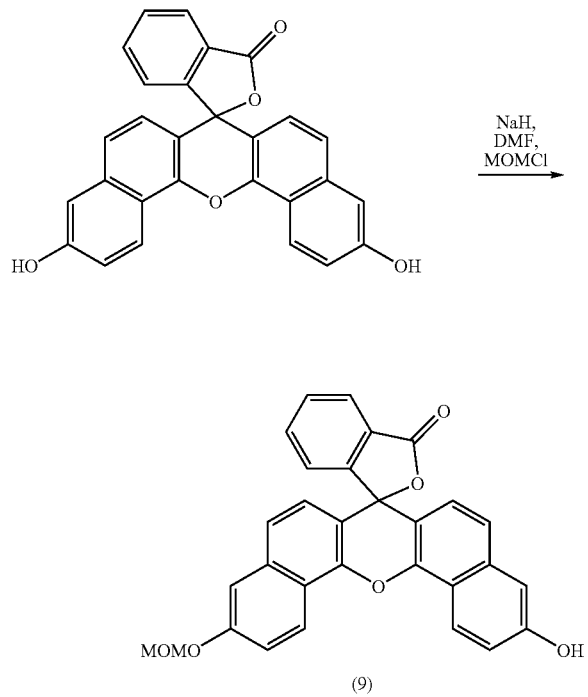

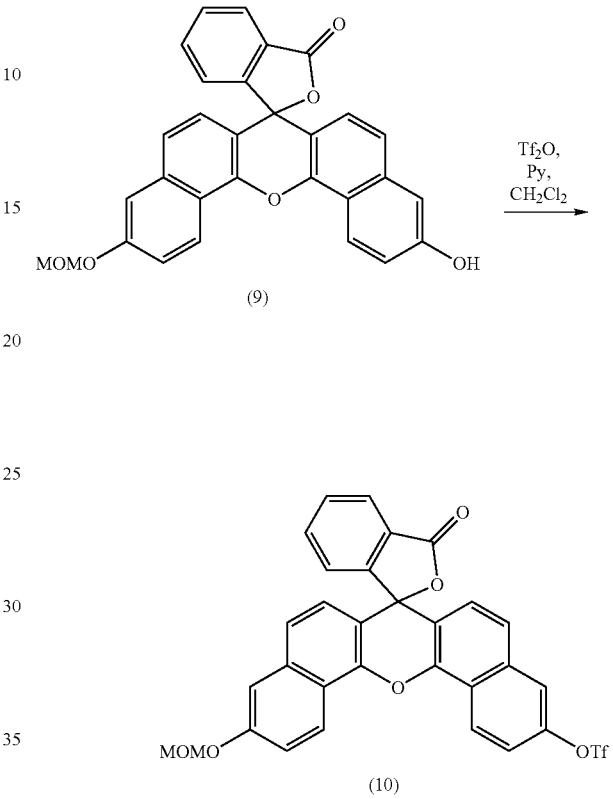

To a solution of naphthofluorescein (4.3 g, 10 mmol) in 50 mL of anhydrous dimethylforamide was added sodium hydride (437 mg, 11 mmol, 60% dispersion in mineral oil) at 0° C. After being stirred at 0° C. for half an hour, the solution was then added methoxymethyl chloride (MOMCl) (0.76 mL, 10 mmol). The resulting mixture was stirred at room temperature overnight and then quenched with water. After that 1N of hydrochloride was added to the mixture to acidify the solution to pH 2. Ethyl acetate was then added. The organic layer was separated and washed with brine, dried over anhydrous sodium sulfate and evaporated in vacuo. The residue was purified by silica gel column chromatography to give Compound 9.

Synthesis of Compound 10

To a solution of Compound 9 (476 mg, 1 mmol) and pyridine (0.32 mL, 4 mmol) in dry dichloromethane under argon gas was added trifluoromethanesulfonic anhydride (0.34 mL, 2 mmol) dropwise at 0° C. The resulting solution was stirred at room temperature for two hours and then quenched with water. Dichloromethane was added to the mixture and the organic layer was separated, washed with 1N of hydrochloric acid followed by water and brine. The organic layer was then dried over anhydrous sodium sulfate and concentrated. The residue was purified by silica gel column chromatography to give Compound 10.

Synthesis of Compound 11

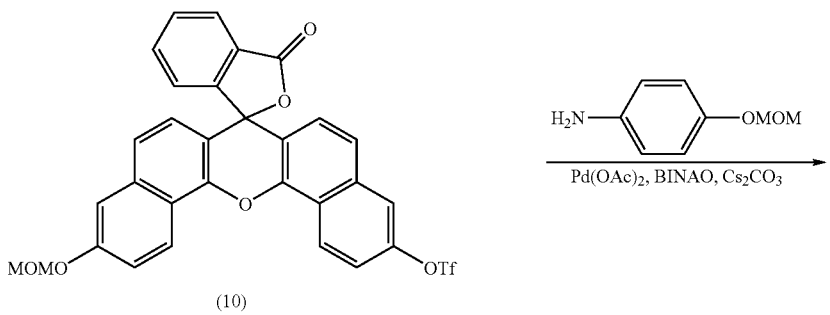

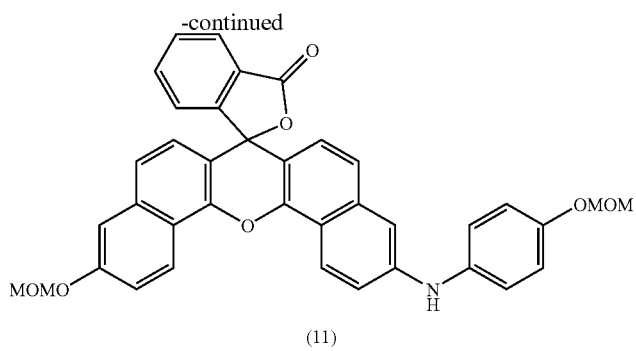

(11)

An oven-dried Schlenk tube was charged with palladium (II) acetate (2 mg, 1% mmol), 2,2'-bis(diphenylphosphino)-1,1'-binaphthyl (BINAP) (9 mg, 1.5% mmol) and cesium carbonate ($Cs_2CO_3$) (91 mg, 0.28 mmol), and flushed with argon gas for 5 minutes. A solution of Compound 10 (122 mg, 0.2 mmol) and 4-(methoxymethoxy)aniline (37 mg, 0.24 mmol) in toluene (2 mL) was added, and the resulting mixture was first stirred under argon gas at room temperature for 30 minutes and then at 100° C. for 20 hours. The reaction mixture was allowed to cool to room temperature, diluted with dichloromethane and filtered through a pad of Celite. The filter cake was washed three times with 10 mL of dichloromethane. The filtrate was then concentrated and the residue was purified by silica gel column chromatography to give Compound 11.

Synthesis of Compound 5

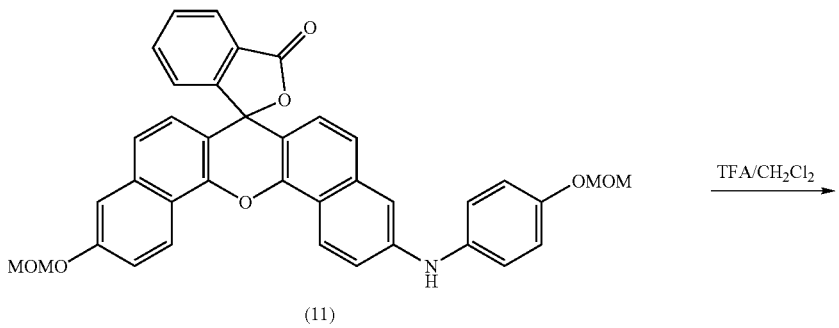

(11)

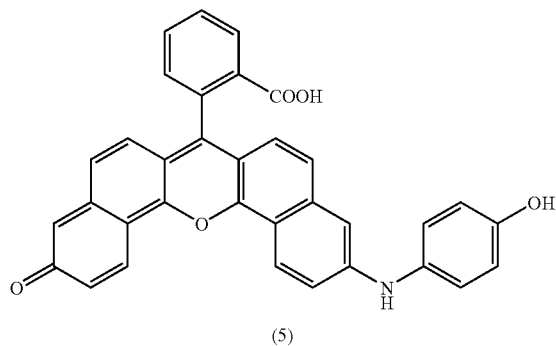

(5)

To a solution of Compound 11 (61 mg, 0.1 mmol) in dry dichloromethane (1 mL) was added trifluoroacetic acid (1 mL) dropwise at 0° C. The resulting solution was stirred at room temperature until the thin layer chromatography indicated that all starting material was consumed. The mixture was then concentrated under vacuo and azeotroped with toluene three times. The residue was purified by silica gel column chromatography to give Compound 5.

Synthesis of Compounds 6 and 7

Compounds 6 and 7 can be synthesized in a similar scheme as shown for Compound 5, including a triflation reaction and a following amination reaction.

Example 3

Evaluation of the Fluorescence of Quenching Compounds

Each of Compounds 1-7 obtained in Example 1 and 2 was dissolved in DMF to a concentration of 10 mM, and then the solution was diluted to 10 μM by 0.1 M phosphate buffer (pH 7.4). The fluorescence spectrum of the 10 μM solution of the compound was measured using a Hitachi F2500 fluorescence spectrometer and the photomultiplier voltage was set to be 700 V. The slit width was 2.5 nm for both excitation and emission. The measurement was carried out at an excitation wavelength of 600 nm. The results indicate that the absolute values of fluorescence intensity for Compounds 1-7 are all below 10. Therefore, Compounds 1-7 are thought to be virtually non-fluorescent.

Example 4

Synthetic Schemes for Compound 10

Synthesis of Compound 15

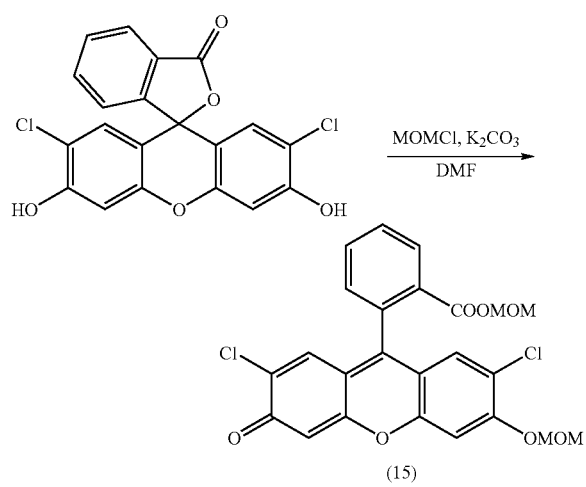

To a solution of 2, 7-dichlorofluorescein (1.0 g, 2.5 mmol) and potassium carbonate (860 mg, 6.2 mmol) in dimethylformamide (DMF) was added chloromethyl methyl ether (0.57 mL, 7.5 mmol). After stirring at room temperature for 3 hours, the reaction mixture was diluted with ethyl acetate and then washed with 1N of hydrochloride solution, water and brine. The organic layer was dried over anhydrous sodium sulfate and concentrated to give Compound 15, which is a red solid.

Synthesis of Compound 16

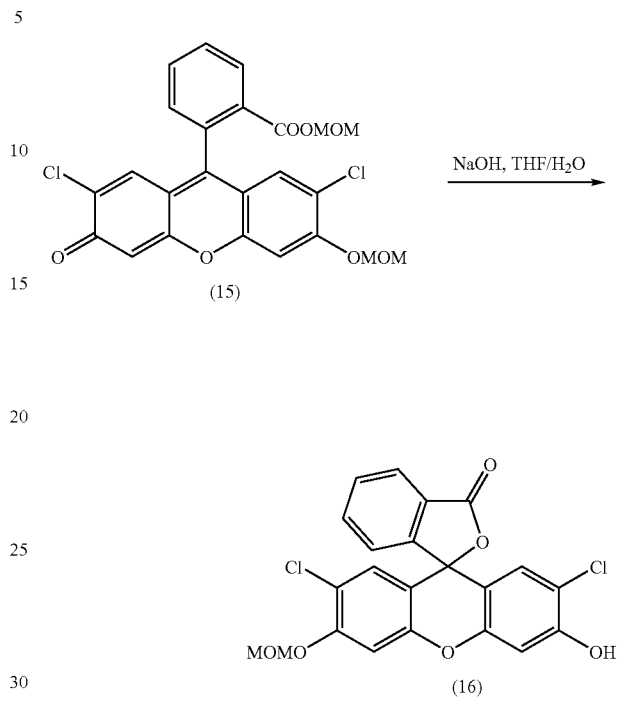

The red solid of Compound 15 was dissolved in a mixture of tetrahydrofuran (30 mL) and water (10 mL) containing sodium hydroxide (3 g, 7.5 mmol). The solution was heated to reflux for 1 hour. After cooling to room temperature, the reaction solution was neutralized with 1N of hydrochloride to pH 2, and then extracted with ethyl acetate. The organic layer was washed with brine, dried over anhydrous sodium sulfate and evaporated in vacuo. The residue was purified by silica gel column chromatography to give Compound 16 (830 mg, 75% yield). Example 16 was characterized by the following spectroscopic data: $^1$H NMR (300 MHz, CDCl$_3$) δ 8.07 (d, J=6.7 Hz, 1H), 7.75-7.67 (m, 2H), 7.17 (d, J=7.0 Hz, 1H), 7.11 (s, 1H), 6.91 (s, 1H), 6.73 (d, J=9.6 Hz, 2H), 6.44 (br, 1H), 5.33-5.28 (m, 2H), 3.53 (s, 3H); $^{13}$C NMR (75.5 MHz, CDCl$_3$) δ 169.2, 154.3, 153.4, 152.1, 151.0, 150.5, 135.6 (CH), 130.4 (CH), 128.7 (CH), 128.0 (CH), 126.2, 125.5 (CH), 123.9 (CH), 119.1, 116.3, 112.6, 112.0, 104.2 (CH), 104.1 (CH), 95.0 (CH$_2$), 82.5, 56.6 (CH$_3$); LRMS (EI) m/z (%) 444 (M$^+$; 5), 355 (100); and HRMS (EI) for C$_{22}$H$_{14}$Cl$_2$O$_6$: the calculated molecular weight was 444.0167, and the found molecular weight was 444.0170.

Synthesis of Compound 17

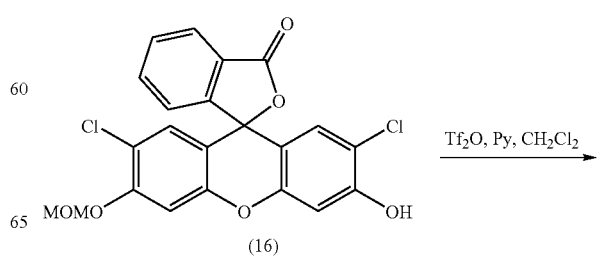

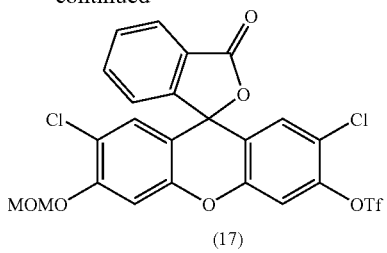

(17)

To a solution of Compound 16 (830 mg, 1.87 mmol) and pyridine (0.6 mL, 7.5 mmol) in dry dichloromethane (CH$_2$Cl$_2$) under argon gas was added trifluoromethane-sulfonic anhydride (0.63 mL, 3.74 mmol) dropwise at 0° C. The resulting solution was stirred at room temperature for two hours and then quenched with water. Dichloromethane was added to the mixture and the organic layer was separated, washed with 1N of hydrochloride followed by water and brine. The organic layer was then dried over anhydrous sodium sulfate and concentrated. The residue was purified by silica gel column chromatography to give Compound 17, which is a white solid (1.06 g, 98% yield). Compound 17 was characterized by the following spectroscopic data: $^1$H NMR (400 MHz, CDCl$_3$) δ8.09 (d, J=7.2 Hz, 1H), 7.79-7.70 (m, 2H), 7.35 (s, 1H), 7.21-7.17 (m, 2H), 6.95 (s, 1H), 6.80 (s, 1H), 6.44 (br, 1H), 5.34-5.29 (m, 2H), 3.53 (s, 3H); $^{13}$C NMR (100 MHz, CDCl$_3$) δ168.4, 154.6, 151.6, 150.0, 149.8, 146.1, 135.8 (CH), 130.7 (CH), 130.0 (CH), 128.6 (CH), 125.7 (CH), 123.7 (CH), 122.0, 120.4, 120.1, 119.9, 118.5 (q, J$_{C-F}$=319.0 Hz), 112.2 (CH), 112.0, 104.1 (CH), 95.1 (CH$_2$), 80.3, 56.5 (CH$_3$); $^{19}$F NMR (377 MHz, CDCl$_3$) δ-73.1; LRMS (EI) m/z (%) 577 (M$^-$; 20), 400 (100); and HRMS (EI) for C$_{23}$H$_{13}$Cl$_2$F$_3$O$_8$S: the calculated molecular weight was 575.9660, and the found molecular weight was 575.9660.

Synthesis of Compound 18

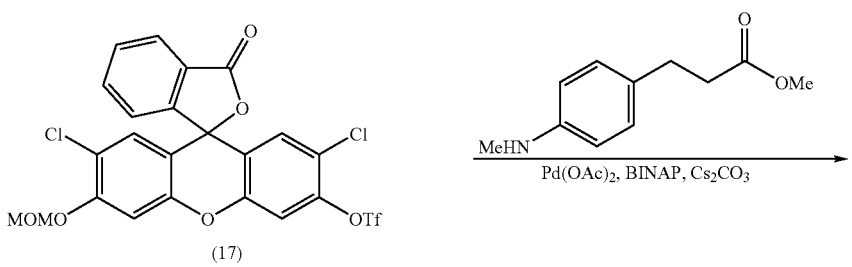

(17)

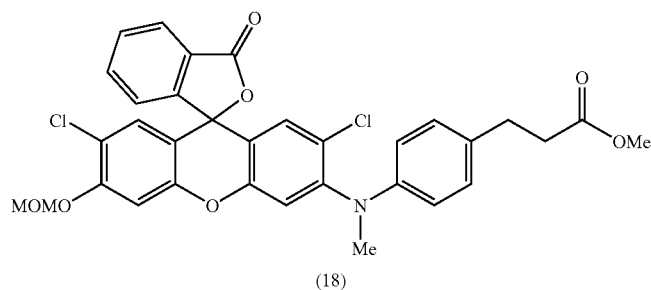

(18)

An oven-dried Schlenk tube was charged with palladium (II) acetate (6 mg, 2.5% mmol), 2,2'-bis(diphenylphosphino)-1,1'-binaphthyl (BINAP) (24 mg, 3.75% mmol) and cesium carbonate ($Cs_2CO_3$) (228 mg, 0.7 mmol), and flushed with argon gas for 5 minutes. A solution of Compound 17 (289 mg, 0.5 mmol) and 3-(4-(methylamino)phenyl)propionic acid methyl ester (116 mg, 0.6 mmol) in toluene (5 mL) was added. The resulting mixture was first stirred under argon gas at room temperature for 30 minutes and then at 100° C. for 20 hours. The reaction mixture was allowed to cool to room temperature, diluted with dichloromethane and filtered through a pad of Celite. The filter cake was washed three times with 10 mL of dichloromethane. The filtrate was then concentrated and the residue was purified by silica gel column chromatography to give Example 18 (264 mg, 85% yield).

Compound 18 was characterized by the following spectroscopic data: $^1$H NMR (400 MHz, $CDCl_3$) δ 8.08 (d, J=7.5 Hz, 1H), 7.77-7.67 (m, 2H), 7.23 (d, J=7.5 Hz, 1H), 7.17 (s, 1H), 7.11 (s, 1H), 7.06 (d, J=8.4 Hz, 2H), 6.82 (s, 1H), 6.78 (s, 1H), 6.67 (d, J=8.4 Hz, 2H), 5.30 (m, 2H), 3.66 (s, 3H), 3.52 (s, 3H), 3.26 (s, 3H), 2.88 (t, J=7.8 Hz, 2H), 2.59 (t, J=7.8 Hz, 2H); $^{13}$C NMR (100 MHz, $CDCl_3$) δ 173.4, 168.7, 154.4, 151.9, 150.5, 150.4, 148.1, 146.6, 135.5, 131.7, 130.4, 129.6, 128.9, 128.7, 127.1, 126.2, 125.5, 123.9, 119.1, 116.6, 116.2, 116.1, 112.5, 104.1, 95.0, 81.4, 56.5, 51.5, 39.8, 35.9, 30.0; LRMS (EI) m/z (%) 619 ($M^+$; 9), 540 (42), 136 (100); and HRMS (EI) for $C_{33}H_{27}Cl_2NO_7$: the calculated molecular weight was 619.1165, and the found molecular weight was 619.1188.

Synthesis of Compound 19

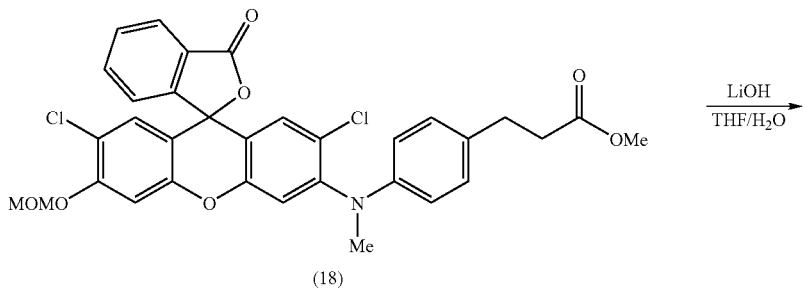

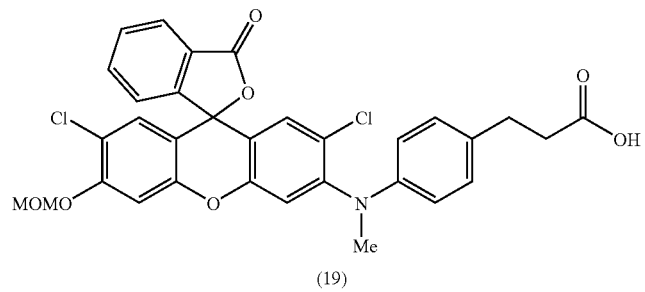

To a solution of Compound 18 (264 mg, 0.43 mmol) in tetrahydrofuran (6 mL) and water (2 mL) was added lithium hydroxide (95 mg, 2.2 mmol) at 0° C. The reaction mixture was stirred at 0° C. until all starting material was consumed. After that the mixture was acidified with 1 N of hydrochloride. The solution was saturated with sodium chloride and extracted three times with 15 mL of ethyl acetate. The combined organic layer was dried over anhydrous sodium sulfate and concentrated. The residue was purified by silica gel column chromatography to give Compound 19 (237 mg, 92% yield). Example 19 was characterized by the following spectroscopic data: $^1$H NMR (400 MHz, CDCl$_3$) δ 8.08 (d, J=7.5 Hz, 1H), 7.77-7.68 (m, 2H), 7.23 (d, J=7.5 Hz, 1H), 7.17 (s, 1H), 7.11 (s, 1H), 7.07 (d, J=8.4 Hz, 2H), 6.83 (s, 1H), 6.78 (s, 1H), 6.67 (d, J=8.4 Hz, 2H), 5.29 (m, 2H), 3.51 (s, 3H), 3.26 (s, 3H), 2.88 (t, J=7.5 Hz, 2H), 2.64 (t, J=7.5 Hz, 2H); $^{13}$C NMR (100 MHz, CDCl$_3$) δ 178.8, 168.8, 154.4, 151.9, 150.5, 150.4, 148.1, 146.6, 135.5, 131.3, 130.4, 129.6, 128.9, 128.7, 127.2, 126.2, 125.5, 123.9, 119.1, 116.6, 116.3, 116.0, 112.5, 104.1, 95.0, 81.5, 56.5, 39.8, 35.7, 29.7; LRMS (FAB) m/z (%) 607 (M+H$^+$; 8), 570 (35), 219 (100); and HRMS (EI) for C$_{32}$H$_{25}$ClNO$_7$ (M$^+$−Cl): the calculated molecular weight was 570.1320, and the found molecular weight was 570.1307.

Synthesis of Compound 20

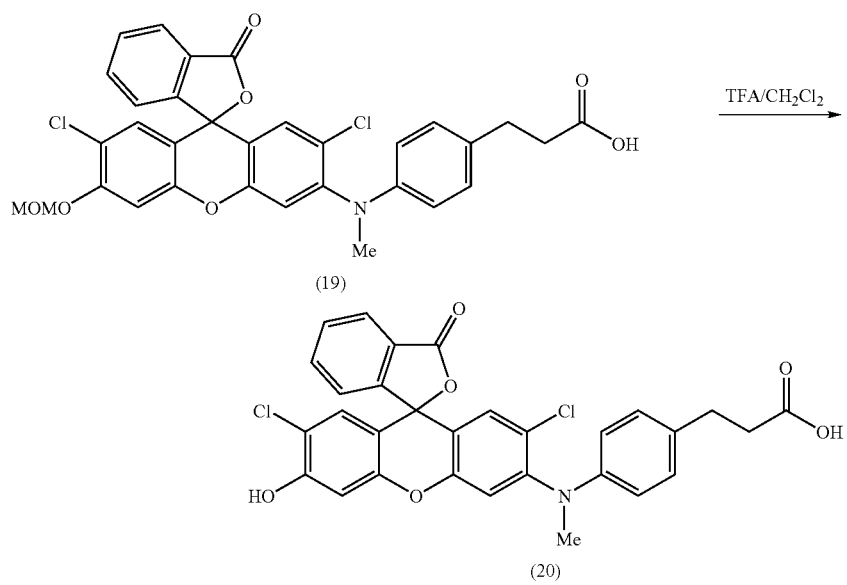

To a solution of Compound 19 (237 mg, 0.39 mmol) in dry dichloromethane (3 mL) was added trifluoroacetic acid (3 mL) dropwise at 0° C. The resulting solution was stirred at room temperature until the thin layer chromatography indicated that all starting material was consumed. The mixture was then concentrated under vacuo and azeotroped with toluene three times to give Example 20 (250 mg, 100% yield), which was directly subjected into the next step without any further purifications. Compound 20 was characterized by the following spectroscopic data: $^1$H NMR (400 MHz, CD$_3$OD) δ 8.05 (d, J=7.6 Hz, 1H), 7.83-7.72 (m, 2H), 7.26 (d, J=7.6 Hz, 1H), 7.19 (s, 1H), 7.05 (d, J=8.6 Hz, 2H), 6.84 (s, 1H), 6.77 (s, 1H), 6.66 (s, 1H), 6.65 (d, J=8.6 Hz, 2H), 3.24 (s, 3H), 2.81 (t, J=7.6 Hz, 2H), 2.53 (t, J=7.6 Hz, 2H).

Synthesis of Compound 21

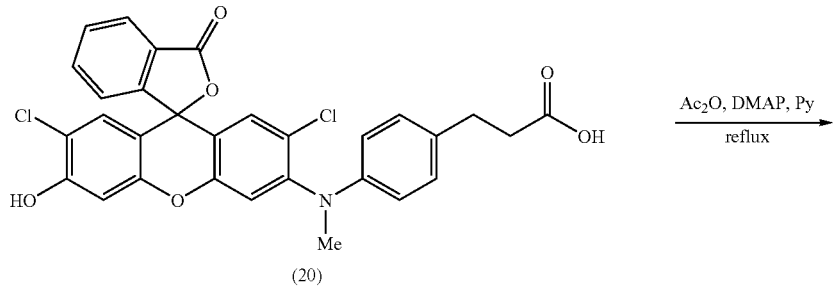

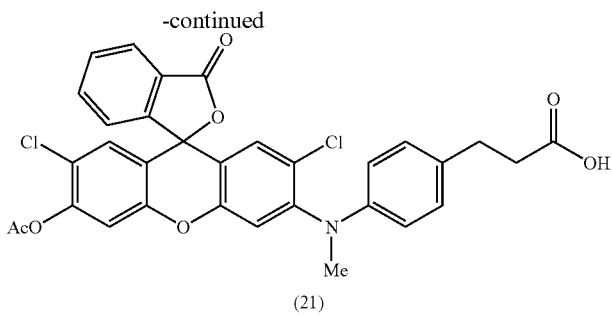

To a solution of Compound 20 (250 mg, 0.39 mmol) in pyridine (8 mL) was added acetic anhydride (3 mL) and 4-dimethylaminopyridine (DMAP) (10 mg, 0.08 mmol). The resulting mixture was heated to reflux for 2 hours. Then the reaction mixture was quenched with water and diluted with ethyl acetate. The organic solution was washed with saturated sodium bicarbonate ($NaHCO_3$) and brine, dried over anhydrous sodium sulfate and concentrated. The residue was purified by silica gel column chromatography to give Compound 21 (172 mg, 73% yield). Compound 21 was characterized by the following spectroscopic data: $^1$H NMR (300 MHz, $CDCl_3$) δ 8.07 (d, J=7.5 Hz, 1H), 7.74-7.68 (m, 2H), 7.26 (d, J=7.5 Hz, 1H), 7.19 (s, 1H), 7.12 (s, 1H), 7.08 (d, J=8.3 Hz, 2H), 6.87 (s, 1H), 6.84 (s, 1H), 6.68 (d, J=8.3 Hz, 2H), 3.26 (s, 3H), 2.89 (t, J=7.8 Hz, 2H), 2.64 (t, J=7.8 Hz, 2H), 2.37 (s, 3H); $^{13}$C NMR (75.5 MHz, $CDCl_3$) δ 178.0, 168.6, 168.0, 151.7, 150.2, 150.0, 148.4, 148.3, 146.6, 135.7 (CH), 131.5, 130.6 (CH), 129.6 (CH), 129.0 (CH), 128.9 (CH), 127.5, 126.0, 125.7 (CH), 124.0 (CH), 122.4, 117.8, 116.4, 116.3 (CH), 116.2 (CH), 112.7 (CH), 80.9, 39.9 ($CH_3$), 35.6 ($CH_2$), 29.8 ($CH_2$), 20.6 ($CH_3$); LRMS (EI) m/z (%) 569/568 ($M^+$–Cl; 10), 482 (40), 219 (100); and HRMS (EI) for $C_{32}H_{23}ClNO_7$ ($M^+$–Cl): the calculated molecular weight was 568.1163, and the found molecular weight was 568.1160.

Synthesis of Compound 22

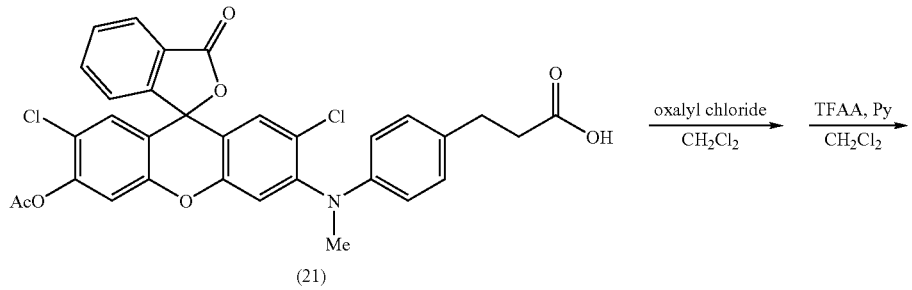

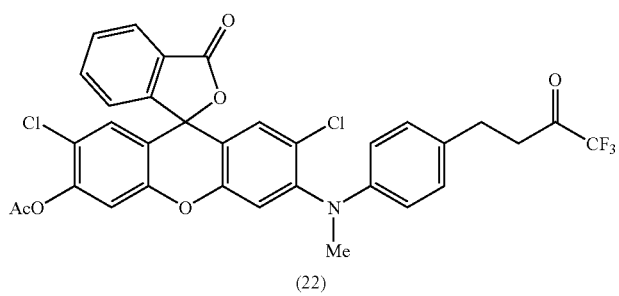

To a solution of Compound 21 (172 mg, 0.28 mmol) in dry dichloromethane (4 mL) was added oxalyl chloride (0.12 mL, 1.4 mmol), and stirred at room temperature for 2 hours. Then the solvent and excess oxalyl chloride were evaporated off under reduced pressure. The resulting acid chloride was re-dissolved in dry dichloromethane (10 mL). To the above solution at −40° C. under argon gas was added trifluoroacetic anhydride (0.24 mL, 1.7 mmol) and pyridine (0.17 mL, 2.2 mmol) successively. The resulting mixture was allowed to warm slowly to −20° C. and stirred at that temperature for 4 hours. After that the reaction was quenched by slow addition of water (5 mL). The mixture was then diluted with dichloromethane, washed with brine, dried over anhydrous sodium sulfate and concentrated. The resulting residue was purified by silica gel column chromatography to give Compound 22 (116 mg, 63% yield). Compound 22 was characterized by the following spectroscopic data: $^1$H NMR (400 MHz, CDCl$_3$) δ 8.09 (d, J=7.5 Hz, 1H), 7.79-7.69 (m, 2H), 7.26 (d, J=7.5 Hz, 1H), 7.19 (s, 1H), 7.12 (s, 1H), 7.05 (d, J=8.6 Hz, 2H), 6.87 (s, 1H), 6.85 (s, 1H), 6.67 (d, J=8.6 Hz, 2H), 3.27 (s, 3H), 3.01 (t, J=7.3 Hz, 0.85×2H, —COCF$_3$), 2.92 (t, J=7.3 Hz, 0.85×2H, —COCF$_3$), 2.82 (t, J=7.3 Hz, 0.15×2H, —C(OH)$_2$CF$_3$), 2.37 (s, 3H), 2.13 (t, J=7.3 Hz, 0.15×2H, —C(OH)$_2$CF$_3$); $^{13}$C NMR (75.5 MHz, CDCl$_3$) δ 190.5 (q, J=35.2 Hz), 168.5, 167.9, 151.7, 150.3, 150.0, 148.4, 148.2, 146.9, 135.7, 130.6, 130.4, 129.7, 129.0, 128.9, 127.6, 126.0, 125.7, 124.0, 122.4, 117.8, 116.6, 116.5, 116.1, 115.8 (q, J$_{C-F}$=297.7), 112.7, 80.8, 39.8, 38.3, 27.5, 20.6; LRMS (EI) m/z (%) 656 (M$^+$; 17), 534 (100); and HRMS (EI) for C$_{33}$H$_{22}$Cl$_2$F$_3$NO$_6$: the calculated molecular weight was 655.0776, and the found molecular weight was 655.0783.

Synthesis of Compound 10

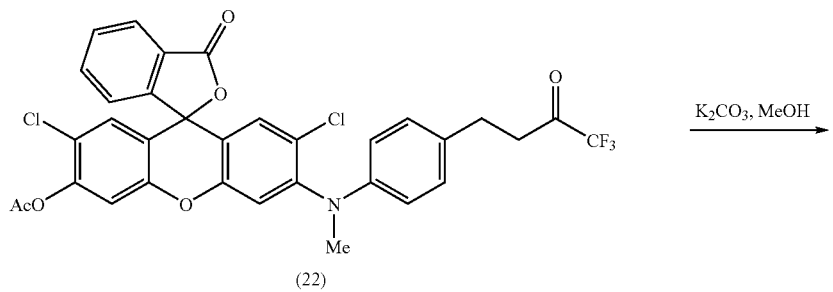

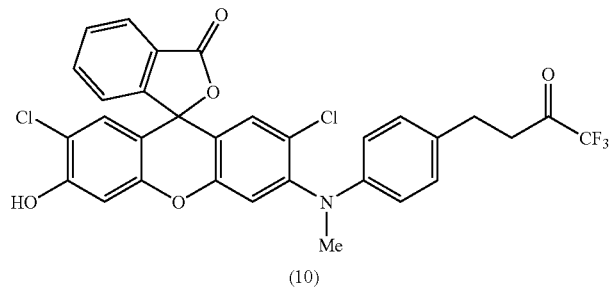

To a solution of Compound 22 (66 mg, 0.1 mmol) in methanol (3 mL) was added a solution of potassium carbonate (41 mg, 0.3 mmol) in water (1 mL). After stirring at room temperature for 3 hours, the resulting mixture was diluted with ethyl acetate, washed with diluted hydrochloric acid and brine. The organic solution was then dried over anhydrous sodium sulfate and concentrated. The residue was purified by silica gel column chromatography to give Compound 10 (60 mg, 98% yield). Compound 10 was characterized by the following spectroscopic data: $^1$H NMR (400 MHz, CDCl$_3$) δ 8.08 (d, J=7.5 Hz, 1H), 7.79-7.69 (m, 2H), 7.25 (d, J=7.5 Hz, 1H), 7.18 (s, 1H), 7.05 (d, J=8.3 Hz, 2H), 6.92 (s, 1H), 6.82 (s, 1H), 6.74 (s, 1H), 6.68 (d, J=8.3 Hz, 2H), 3.26 (s, 3H), 3.01 (t, J=7.0 Hz, 2H), 2.91 (t, J=7.5 Hz, 2H); $^{13}$C NMR (100 MHz, CDCl$_3$) δ 190.9 (q, J=35.0 Hz), 169.0, 153.5, 151.9, 151.0, 150.5, 148.0, 146.9, 135.7, 130.5, 130.3, 129.7, 128.9, 128.0, 127.2, 126.2, 125.6, 123.9, 116.7, 116.5, 116.1, 116.3, 115.5 (q, $J_{C-F}$=290.3), 112.0, 104.2, 81.7, 39.8, 38.3, 27.4; LRMS (EI) m/z (%) 614 (M$^+$; 16), 535 (100); and HRMS (EI) for $C_{31}H_{20}Cl_2F_3NO_5$: the calculated molecular weight was 613.0671, and the found molecular weight was 613.0682.

Example 5

Synthetic Schemes for Compounds 12 and 12a

Synthesis of Compound 23

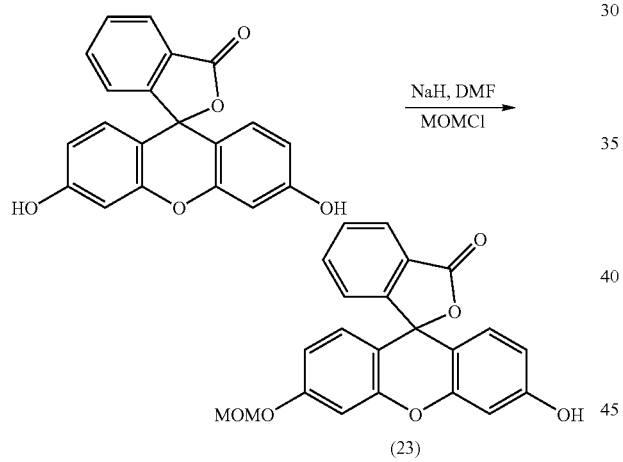

To a solution of fluorescein (3.3 g, 10 mmol) in 50 mL of anhydrous dimethylformamide was added sodium hydride (437 mg, 11 mmol, 60% dispersion in mineral oil) at 0° C. After being stirred at 0° C. for half an hour, the solution was then added methoxymethyl chloride (MOMCl) (0.76 mL, 10 mmol). The resulting mixture was stirred at room temperature overnight and then quenched with water. After that 1N of hydrochloride was added to the mixture to acidify the solution to pH 2. Ethyl acetate was then added. The organic layer was separated and washed with brine, dried over anhydrous sodium sulfate and evaporated in vacuo. The residue was purified by silica gel column chromatography to give Compound 23 (3.2 g, 85% yield). Compound 23 was characterized by the following spectroscopic data: $^1$H NMR (400 MHz, CDCl$_3$) δ 8.01 (d, J=7.6 Hz, 1H), 7.66-7.59 (m, 2H), 7.14 (d, J=7.6 Hz, 1H), 6.92 (d, J=1.7 Hz, 1H), 6.73 (d, J=1.9 Hz, 1H), 6.68-6.67 (m, 2H), 6.55-6.54 (m, 2H), 5.18 (s, 2H), 3.46 (s, 3H); $^{13}$C NMR (100 MHz, CDCl$_3$) δ 170.6, 158.7, 158.6, 152.8, 152.4, 152.3, 135.3 (CH), 129.8 (CH), 129.0 (CH), 128.9 (CH), 126.5, 125.0 (CH), 124.0 (CH), 112.9 (CH), 112.6 (CH), 112.0, 110.2, 103.5 (CH), 103.1 (CH), 94.1 (CH$_2$), 85.2, 56.1 (CH$_3$); LRMS (EI) m/z (%) 376 (M$^+$; 7), 332 (100); and HRMS (EI) for $C_{22}H_{16}O_6$: the calculated molecular weight was 376.0947, and the found molecular weight was 376.0949.

Synthesis of Compound 24

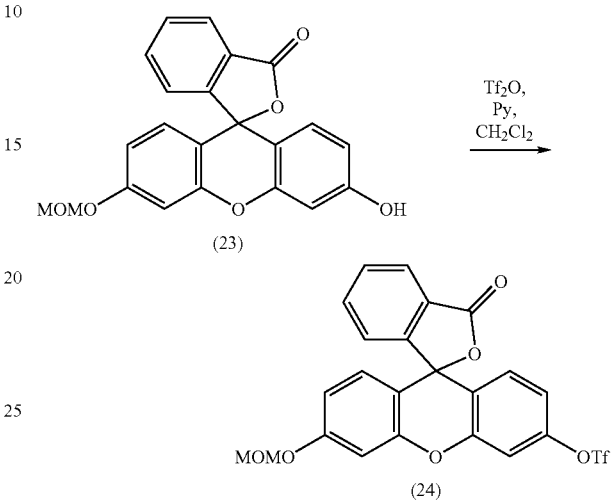

To a solution of Compound 23 (3.2 g, 8.5 mmol) and pyridine (2.74 mL, 34 mmol) in dry dichloromethane under argon gas was added trifluoromethanesulfonic anhydride (2.86 mL, 17 mmol) dropwise at 0° C. The resulting solution was stirred at room temperature for two hours and then quenched with water. Dichloromethane was added to the mixture and the organic layer was separated, washed with 1N of hydrochloride followed by water and brine. The organic layer was then dried over anhydrous sodium sulfate and concentrated. The residue was purified by silica gel column chromatography to give Compound 24 (4.2 g, 98% yield). Compound 24 was characterized by the following spectroscopic data: $^1$H NMR (400 MHz, CDCl$_3$) δ 8.04 (d, J=7.5 Hz, 1H), 7.72-7.65 (m, 2H), 7.27 (d, J=2.3 Hz, 1H), 7.18 (d, J=7.4 Hz, 1H), 7.01-6.93 (m, 3H), 6.77-6.73 (m, 2H), 5.19 (s, 2H), 3.46 (s, 3H); $^{13}$C NMR (100 MHz, CDCl$_3$) δ 168.7, 159.0, 152.3, 151.9, 151.5, 149.8, 135.3 (CH), 130.1 (CH), 129.9 (CH), 128.8 (CH), 126.0, 125.1 (CH), 123.7 (CH), 123.0, 120.1, 119.7, 116.9, 116.5 (CH), 113.6 (CH), 111.6, 110.3 (CH), 103.5 (CH), 94.1 (CH$_2$), 81.3, 55.9 (CH$_3$); $^{19}$F NMR (377 MHz, CDCl$_3$) δ-72.7; LRMS (EI) m/z (%) 508 (M$^-$; 23), 331 (100); and HRMS (EI) for $C_{23}H_{15}F_3O_8S$: the calculated molecular weight was 508.0440, and the found molecular weight was 508.0438.

Synthesis of Compound 25

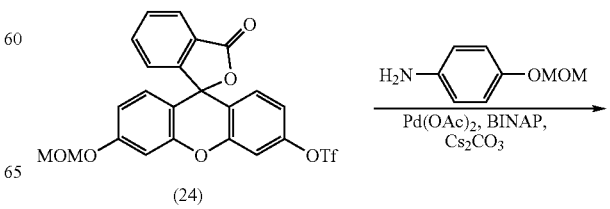

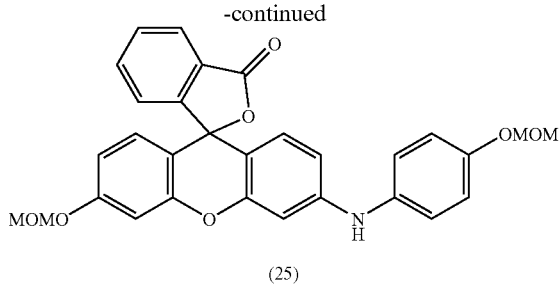

An oven-dried Schlenk tube was charged with palladium (II) acetate (2 mg, 1% mmol), 2,2'-bis(diphenylphosphino)-1,1'-binaphthyl (BINAP) (9 mg, 1.5% mmol) and cesium carbonate ($Cs_2CO_3$) (91 mg, 0.28 mmol), and flushed with argon gas for 5 minutes. A solution of Compound 24 (102 mg, 0.2 mmol) and 4-(methoxymethoxy)aniline (37 mg, 0.24 mmol) in toluene (2 mL) was added, and the resulting mixture was first stirred under argon gas at room temperature for 30 minutes and then at 100° C. for 20 hours. The reaction mixture was allowed to cool to room temperature, diluted with dichloromethane and filtered through a pad of Celite. The filter cake was washed three times with 10 mL of dichloromethane. The filtrate was then concentrated and the residue was purified by silica gel column chromatography to give Compound 25 (84 mg, 82% yield). Compound 25 was characterized by the following spectroscopic data: $^1$H NMR (300 MHz, $CDCl_3$) δ 7.99 (d, J=7.4 Hz, 1H), 7.66-7.58 (m, 2H), 7.16 (d, J=7.4 Hz, 1H), 7.08 (d, J=8.9 Hz, 2H), 6.99 (d, J=8.9 Hz, 2H), 6.91 (s, 1H), 6.73 (s, 1H), 6.67 (s, 2H), 6.57-6.48 (m, 2H), 5.94 (s, br, 1H), 5.16 (s, 2H), 5.14 (s, 2H), 3.48 (s, 3H), 3.45 (s, 3H); $^{13}$C NMR (75.5 MHz, $CDCl_3$) δ 169.6, 158.8, 153.5, 153.1, 152.6, 152.5, 147.6, 135.3, 134.9, 129.6, 129.1, 129.0, 127.0, 124.9, 124.0, 123.2, 117.4, 112.7, 112.6, 111.9, 109.0, 103.6, 100.8, 94.9, 94.3, 83.8, 56.1, 56.0; LRMS (EI) m/z (%) 511 (M$^+$; 47), 467 (100); and HRMS (EI) for $C_{30}H_{25}NO_7$: the calculated molecular weight was 511.1631, and the found molecular weight was 511.1632.

Synthesis of Compound 25

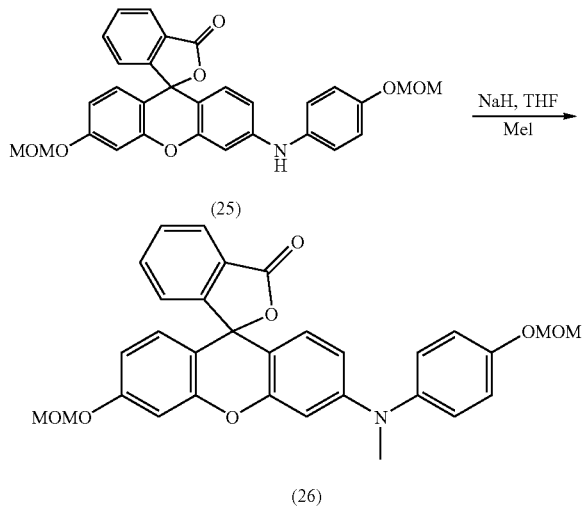

To a solution of Compound 25 (84 mg, 0.16 mmol) in tetrahydrofuran (4 mL) at 0° C. was added sodium hydride (10 mg, 0.24 mmol, 60% in mineral oil). The suspension was stirred for half an hour and then methyl iodide (20 μL, 0.32 mmol) was introduced. The mixture was stirred at room temperature overnight and then quenched with water. The mixture was diluted with ethyl acetate, washed with 1N hydrochloric acid and brine. After dried over anhydrous sodium sulfate the organic solution was concentrated in vacuo and the residue was purified by silica gel column chromatography to give Compound 26 (64 mg, 76% yield). Compound 26 was characterized by the following spectroscopic data: $^1$H NMR (300 MHz, $CDCl_3$) δ 7.98 (d, J=7.2 Hz, 1H), 7.66-7.58 (m, 2H), 7.15 (d, J=7.2 Hz, 1H), 7.14-7.08 (m, 2H), 7.04 (d, J=9.0 Hz, 2H), 6.92 (s, 1H), 6.67 (s, 1H), 6.52 (d, J=9.0 Hz, 2H), 6.36-6.34 (m, 2H), 5.16 (s, 4H), 3.48 (s, 3H), 3.45 (s, 3H), 3.25 (s, 3H); $^{13}$C NMR (75.5 MHz, $CDCl_3$) δ 169.5, 158.7, 155.0, 153.1, 152.6, 152.4, 151.5, 141.7, 134.8, 129.5, 129.1, 128.4, 127.7, 127.1, 124.8, 124.0, 117.5, 112.8, 112.6, 110.9, 107.5, 103.6, 100.5, 94.6, 94.3, 83.8, 56.1, 56.0, 40.4; LRMS (EI) m/z (%) 526 (M$^+$; 8), 482 (100); and HRMS (EI) for $C_{31}H_{27}NO_7$: the calculated molecular weight was 525.1788, and the found molecular weight was 525.1792.

Synthesis of Compound 12

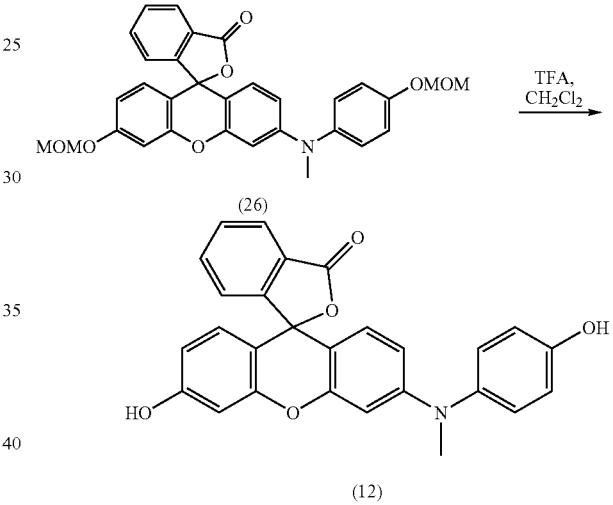

To a solution of Compound 26 (64 mg, 0.12 mmol) in dry dichloromethane ($CH_2Cl_2$) (2 mL) was added trifluoroacetic acid (2 mL) dropwise at 0° C. The resulting solution was stirred at room temperature until the thin layer chromatography indicated that all starting material was consumed. The mixture was then concentrated in vacuo and azeotroped with toluene three times. The residue was dissolved in ethyl acetate and washed with saturated sodium bicarbonate ($NaHCO_3$), followed by water and brine. The organic solution was concentrated in vacuo and then the residue was purified by silica gel column chromatography to give Compound 12 (47 mg, 90% yield). Compound 12 was characterized by the following spectroscopic data: $^1$H NMR (500 MHz, $CD_3OD$) δ 8.26 (d, J=7.7 Hz, 1H), 7.83-7.75 (m, 2H), 7.35 (d, J=7.7 Hz, 1H), 7.13 (d, J=8.7 Hz, 2H), 7.09 (d, J=9.0 Hz, 1H), 7.04-7.02 (m, 2H), 6.92-6.88 (m, 4H), 6.80 (d, J=9.4 Hz, 1H), 3.52 (s, 3H); $^{13}$C NMR (125.8 MHz, $CD_3OD$) δ 169.1, 168.2, 159.3, 159.1, 158.7, 158.0, 139.2, 138.1, 134.6, 132.3, 132.1, 131.7, 131.6, 131.3, 130.1, 130.0, 128.9, 118.1, 118.0, 117.4, 115.9, 115.4, 103.6, 99.1, 42.3; LRMS (EI) m/z (%) 437 (M$^+$; 6), 393 (100); and HRMS (EI) for $C_{27}H_{19}NO_5$: the calculated molecular weight was 437.1263, and the found molecular weight was 437.1266.

Synthesis of Compound 12a

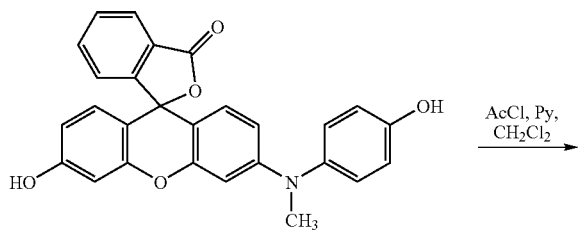

To a solution of Compound 12 (108 mg, 0.25 mmol) in dry dichloromethane (CH$_2$Cl$_2$) (4 mL) was added pyridine (0.4 mL) and acetyl chloride (0.8 mL) successively. The resulting solution was stirred at room temperature until thin layer chromatography indicated that all starting material was consumed. The reaction was then quenched by saturated NH$_4$Cl solution and extracted with ethyl acetate. The organic solution was concentrated in vacuo and then the residue was purified by silica gel column chromatography to give Compound 12a (110 mg, 85% yield). Compound 12a was characterized by the following spectroscopic data: $^1$H NMR (400 MHz, CDCl$_3$) δ 8.00 (d, J=7.2 Hz, 1H), 7.66-7.60 (m, 2H), 7.19-7.17 (m, 3H), 7.08 (d, J=9.0 Hz, 2H), 7.02 (d, J=1.8 Hz, 1H), 7.78-7.76 (m, 2H), 6.66 (d, J=1.8 Hz, 1H), 6.56 (d, J=9.0 Hz, 1H), 6.48 (dd, J=9.0, 1.8 Hz, 1H), 3.31 (s, 3H), 2.30 (s, 6H); $^{13}$C NMR (100 MHz, CDCl$_3$) δ 169.5, 169.3, 168.9, 152.9, 152.2, 152.1, 151.8, 151.0, 147.5, 145.2, 135.0, 129.7, 129.0, 128.5, 126.8, 126.3, 125.0, 124.1, 122.8, 117.2, 116.9, 112.4, 110.2, 108.4, 102.1, 83.0, 40.4, 21.1; LRMS (EI) m/z (%) 521 (M$^+$; 26), 477 (100); and HRMS (EI) for C$_{31}$H$_{23}$NO$_7$: the calculated molecular weight was 521.1475, and the found molecular weight was 521.1471

Example 6

Synthetic Schemes for Compound 14

Synthesis of Compound 27

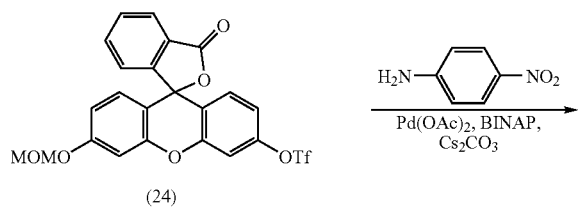

-continued

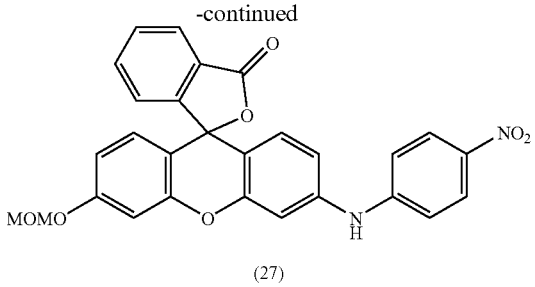

An oven-dried Schlenk tube was charged with palladium (II) acetate (2 mg, 1% mmol), 2,2'-bis(diphenylphosphino)-1,1'-binaphthyl (BINAP) (9 mg, 1.5% mmol) and cesium carbonate (Cs$_2$CO$_3$) (91 mg, 0.28 mmol), and flushed with argon gas for 5 minutes. A solution of Compound 24 (102 mg, 0.2 mmol) and 4-nitroaniline (33 mg, 0.24 mmol) in toluene (2 mL) was added, and the resulting mixture was first stirred under argon gas at room temperature for 30 minutes and then at 100° C. for 20 hours. The reaction mixture was allowed to cool to room temperature, diluted with dichloromethane and filtered through a pad of Celite. The filter cake was washed three times with 10 mL of dichloromethane. The filtrate was then concentrated and the residue was purified by silica gel column chromatography to give Compound 27 (79 mg, 80% yield). Compound 27 was characterized by the following spectroscopic data: $^1$H NMR (300 MHz, CDCl$_3$) δ 8.06-8.01 (m, 3H), 7.72-7.63 (m, 2H), 7.19 (d, J=7.2 Hz, 1H), 7.06-7.03 (m, 3H), 6.93 (s, 1H), 6.80-6.64 (m, 4H), 5.18 (s, 2H), 3.46 (s, 3H); $^{13}$C NMR (75.5 MHz, CDCl$_3$) δ 169.8, 159.0, 152.8, 152.2, 148.8, 142.6, 140.3, 135.4, 130.0, 129.1, 129.0, 126.5, 126.0, 125.1, 124.0, 115.9, 115.1, 113.2, 112.0, 105, 1069, 1037, 943, 834, 56.2; LRMS (FAB) m/z (%) 496 (M$^+$; 20), 154 (100); and HRMS (EI) for C$_{27}$H$_{20}$N$_2$O$_5$ (M$^+$–CO$_2$): the calculated molecular weight was 452.1372, and the found molecular weight was 452.1366.

Synthesis of Compound 28

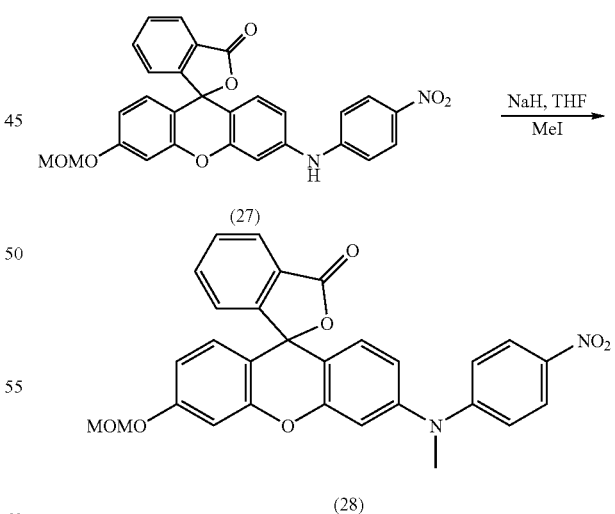

To a solution of Compound 27 (79 mg, 0.16 mmol) in tetrahydrofuran (4 mL) at 0° C. was added sodium hydride (10 mg, 0.24 mmol, 60% in mineral oil). The suspension was stirred for half an hour and then methyl iodide (20 µL, 0.32 mmol) was introduced. The mixture was stirred at room temperature overnight and then quenched with water. The mixture was diluted with ethyl acetate, washed with 1N hydrochloric acid and brine. After dried over anhydrous sodium sulfate the organic solution was concentrated in vacuo and the residue was purified by silica gel column chromatography to give Compound 28 (67 mg, 83% yield). Compound 28 was characterized by the following spectroscopic data: $^1$H NMR (300 MHz, CDCl$_3$) δ 8.10-8.04 (m, 3H), 7.80-7.63 (m, 2H), 7.24 (d, J=7.4 Hz, 1H), 7.14 (d, J=2.0 Hz, 1H), 6.98 (d, J=2.0 Hz, 1H), 6.90-6.82 (m, 4H), 6.76-6.73 (m, 2H), 5.20 (s, 2H), 3.48 (s, 3H), 3.44 (s, 3H); $^{13}$C NMR (75.5 MHz, CDCl$_3$) δ 159.0, 153.0, 152.7, 152.4, 152.1, 148.5, 139.4, 135.2, 130.0, 129.6, 129.1, 126.6, 125.7, 125.2, 124.0, 120.8, 116.5, 114.5, 113.3 (2C), 112.1, 103.7, 94.4, 85.3, 56.2, 40.4; LRMS (FAB) m/z (%) 510 (M$^+$; 20), 109 (100); and HRMS (EI) for C$_{28}$H$_{22}$N$_2$O$_5$ (M$^+$–CO$_2$): the calculated molecular weight was 466.1522, and the found molecular weight was 466.1529.

Synthesis of Compound 29

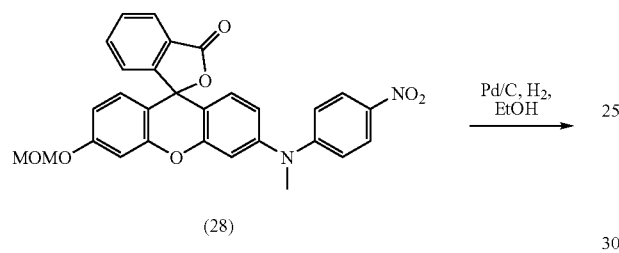

To a solution of Compound 28 (67 mg, 0.13 mmol) in ethanol (10 mL) was slowly added palladium (10% on activated carbon powder, 7 mg). The mixture was hydrogenated for 2 hours at room temperature. The mixture was then filtered through a pad of Celite, and the filtrate was concentrated in vacuo. The residue was purified by silica gel column chromatography to give Compound 29 (48 mg, 77% yield). Compound 29 was characterized by the following spectroscopic data: $^1$H NMR (300 MHz, CDCl$_3$) δ 7.99 (d, J=7.5 Hz, 1H), 7.64-7.57 (m, 2H), 7.17 (d, J=7.5 Hz, 1H), 6.98 (d, J=8.6 Hz, 2H), 6.91 (s, 1H), 6.710-6.67 (m, 4H), 6.51-6.48 (m, 2H), 6.35-6.32 (m, 1H), 5.18 (s, 2H), 3.68 (br, 2H), 3.47 (s, 3H), 3.24 (s, 3H); $^{13}$C NMR (75.5 MHz, CDCl$_3$) δ 169.6, 158.7, 153.2, 152.7, 152.4, 151.8, 144.5, 138.7, 134.7, 129.4, 129.1, 128.3, 128.0, 127.2, 124.8, 124.0, 116.2, 112.8, 112.5, 110.5, 106.8, 103.6, 99.8, 94.4, 84.0, 56.1, 40.4; LRMS (EI) m/z (%) 481 (M$^+$; 24), 437 (100); and HRMS (EI) for C$_{29}$H$_{24}$N$_2$O$_5$: the calculated molecular weight was 480.1685, and the found molecular weight was 480.1688.

Synthesis of Compound 14

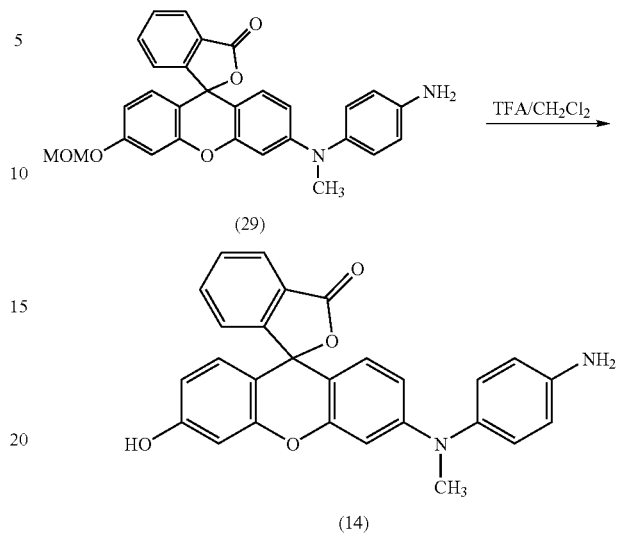

To a solution of Compound 29 (48 mg, 0.10 mmol) in dry dichloromethane (2 mL) was added trifluoroacetic acid (2 mL) dropwise at 0° C. The resulting solution was stirred at room temperature until the thin layer chromatography indicated that all starting material was consumed. The mixture was then concentrated in vacuo and azeotroped with toluene three times. The residue was dissolved in ethyl acetate and washed with saturated sodium bicarbonate (NaHCO$_3$), followed by water and brine. The organic solution was concentrated in vacuo and then the residue was purified by silica gel column chromatography to give Compound 14 (40 mg, 91% yield). Compound 14 was characterized by the following spectroscopic data: $^1$H NMR (400 MHz, CD$_3$OD) δ 8.02 (d, J=7.2 Hz, 1H), 7.70-7.64 (m, 2H), 7.16 (d, J=7.2 Hz, 1H), 6.92 (d, J=8.6 Hz, 2H), 6.76 (d, J=8.6 Hz, 2H), 6.69 (d, J=8.8 Hz, 1H), 6.64 (d, J=2.2 Hz, 1H), 6.59-6.52 (m, 3H), 6.42 (dd, J=8.8, 2.2 Hz, 1H), 3.26 (s, 3H); $^{13}$C NMR (100 MHz, CD$_3$OD) δ 164.6, 154.5, 153.7, 153.6, 153.5, 147.5, 146.2, 137.3, 133.7, 129.5, 129.4, 128.5, 127.6, 127.3, 125.9, 125.4, 116.1, 114.6, 114.1, 111.4, 108.5, 102.3, 98.6, 76.0, 39.7; LRMS (ESI) m/z (%) 437 (M+H$^+$; 100); and HRMS (EI) for C$_{27}$H$_{20}$N$_2$O$_4$: the calculated molecular weight was 436.1423, and the found molecular weight was 436.1424.

Example 7

Synthetic Schemes for Compound 30

Synthesis of Compound 31

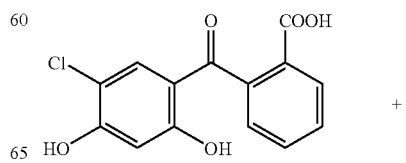

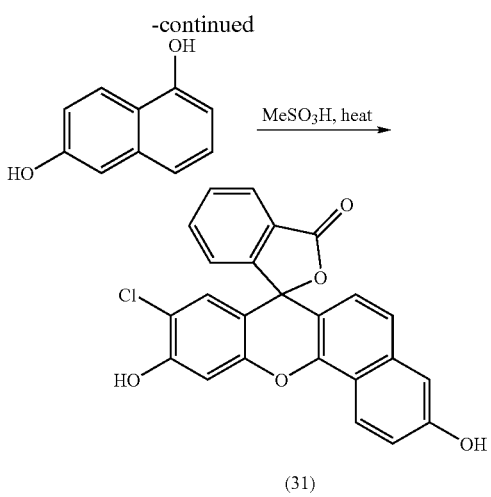

(31)

2'-Carboxy-5-chloro-2,4-dihydroxybenzophenone and 1,6-dihydroxynaphthalene were combined in methanesulfonic acid and sealed in a thich-walled glass tube. After the resulting mixture was stirred at 90° C. for 24 hours, the reaction was poured into ice-cold water, and the precipitate was filtered, washed with water and dried in vacuo. The crude product 31 was used in the next step without further purification.

Synthesis of Compound 32

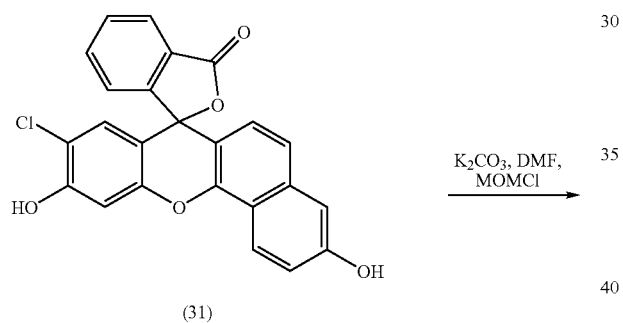

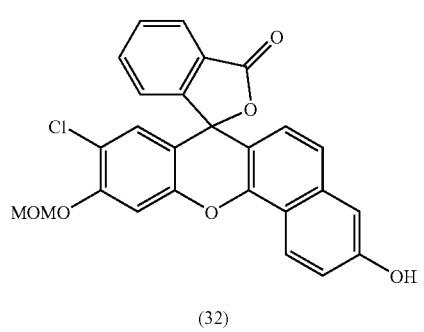

(32)

To a solution of Compound 31 (1.23 g, 2.95 mmol) and potassium carbonate (407 mg, 2.95 mmol) in dimethylformamide (DMF) was added chloromethyl methyl ether (0.22 mL, 2.95 mmol). After stirring at room temperature for 3 hours, the reaction mixture was diluted with ethyl acetate and then washed with 1N of hydrochloride solution, water and brine. The organic layer was dried over anhydrous sodium sulfate and concentrated. The residue was purified by silica gel column chromatography to give Compound 32 (680 mg, 50% yield).

Synthesis of Compound 33

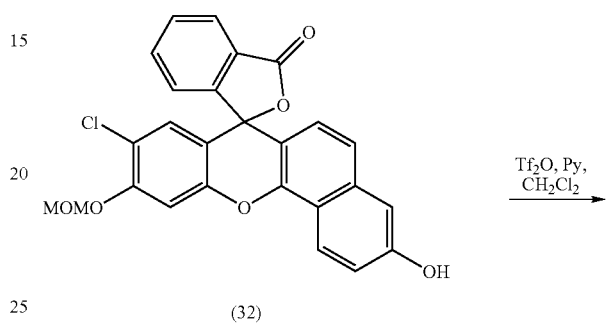

(32)

(33)

To a solution of Compound 32 (340 mg, 0.75 mmol) and pyridine (0.36 mL, 4.48 mmol) in dry dichloromethane (CH$_2$Cl$_2$) under argon gas was added trifluoromethanesulfonic anhydride (0.38 mL, 2.24 mmol) dropwise at 0° C. The resulting solution was stirred at room temperature for two hours and then quenched with water. Dichloromethane was added to the mixture and the organic layer was separated, washed with 1N of hydrochloride followed by water and brine. The organic layer was then dried over anhydrous sodium sulfate and concentrated. The residue was purified by silica gel column chromatography to give Compound 33 as a white solid (436 mg, 98% yield).

Synthesis of Compound 34

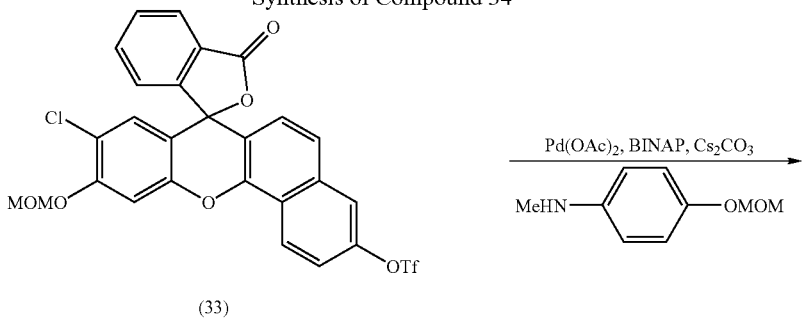

(33)

-continued

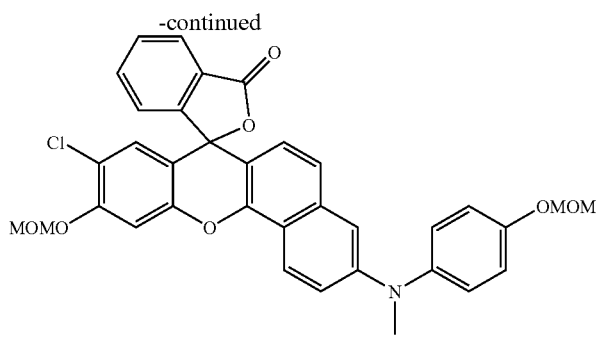

(34)

An oven-dried Schlenk tube was charged with palladium (II) acetate (5 mg, 0.02 mmol), 2,2'-bis(diphenylphosphino)-1,1'-binaphthyl (BINAP) (19 mg, 0.03 mmol) and cesium carbonate ($Cs_2CO_3$) (79 mg, 0.24 mmol), and flushed with argon gas for 5 minutes. A solution of Compound 33 (120 mg, 0.2 mmol) and 4-(methoxymethoxy)-N-methylaniline (36 mg, 0.21 mmol) in toluene (3 mL) was added. The resulting mixture was first stirred under argon gas at room temperature for 30 minutes and then at 100° C. for 20 hours. The reaction mixture was allowed to cool to room temperature, diluted with dichloromethane and filtered through a pad of Celite. The filter cake was washed three times with 10 mL of dichloromethane. The filtrate was then concentrated and the residue was purified by silica gel column chromatography to give Compound 34 (104 mg, 85% yield).

Synthesis of Compound 30

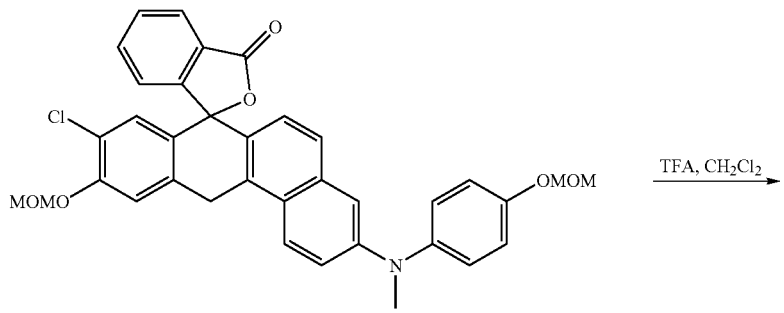

(34)

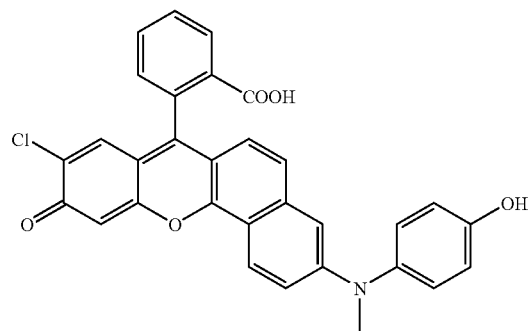

(30)

To a solution of Compound 34 (104 mg, 0.17 mmol) in dry dichloromethane (2 mL) was added trifluoroacetic acid (2 mL) dropwise at 0° C. The resulting solution was stirred at room temperature until thin layer chromatography indicated that all starting material was consumed. The mixture was then concentrated in vacuo and azeotroped with toluene three times. The residue was dissolved in ethyl acetate and washed with saturated sodium bicarbonate ($NaHCO_3$), followed by water and brine. The organic solution was concentrated in vacuo and then the residue was purified by silica gel column chromatography to give Compound 30 (72 mg, 82% yield). Compound 30 was characterized by the following spectroscopic data: $^1$H NMR (400 MHz, $CDCl_3$) δ 8.21 (d, J=9.3 Hz, 1H), 8.09 (dd, J=6.8, 1.1 Hz, 1H), 7.71-7.63 (m, 2H), 7.23 (d, J=8.8 Hz, 1H), 7.16 (dd, J=6.8, 1.1 Hz, 1H), 7.08-7.04 (m, 3H), 6.99 (s, 1H), 6.91-6.86 (m, 3H), 6.80 (s, 1H), 6.61 (dd, J=8.8 Hz, 1H), 3.33 (s, 3H), 3.18 (br, 2H); $^{13}$C NMR (100 MHz, $CDCl_3$) δ 169.7, 154.5, 152.0, 149.5, 147.5, 140.3, 136.5, 135.0, 129.9, 128.4, 127.2, 126.9, 125.7, 124.6, 123.8, 122.6, 122.5, 118.1, 116.4, 116.2, 111.9, 108.2, 107.3, 104.1, 40.6; LRMS (EI) m/z (%) 521 ($M^+$; 16), 476 (100); and HRMS (EI) for $C_{31}H_{20}ClNO_5$: the calculated molecular weight was 521.1030, and the found molecular weight was 521.1033.

Example 8

Specific Detection of Peroxynitrite with Compound 10

UV-Visible Absorption Spectrum of Compound 10

Compound 10 obtained in Example 4 was dissolved in pH 7.4 0.1 M phosphate buffer containing 0.1% DMF as cosolvent to form a 10 μM solution. The absorption spectrum of the 10 μM solution of Compound 10 was measured and showed that Compound 10 has an absorption maximum at about 520 nm.

Emission Spectra of Compound 10

Compound 10 obtained in Example 4 was dissolved in DMF to a concentration of 10 mM, and then the solution was diluted to 10 μM by 0.1 M phosphate buffer (pH 7.4). The fluorescence spectrum of the 10 μM solution of Compound 10 was measured using a Hitachi F2500 fluorescence spectrometer and the photomultiplier voltage was 700 V. The slit width was 2.5 nm for both excitation and emission. The measurement was carried out at an excitation wavelength of 520 nm. The results shown in FIG. 1 indicate that Compound 10 itself is non-fluorescent.

Detection of Peroxynitrite with Compound 10

Compound 10 obtained in Example 4 was dissolved in DMF to a concentration of 10 mM, and then the solution was diluted to 10μM by 0.1 M potassium phosphate buffer (pH 7.4). Peroxynitrite solution in 0.1 M NaOH was prepared by the method of Keith and Powell (Keith, W. G. & Powell, R. E.; Kinetics of decomposition of peroxynitrous acid; *J. Chem. Soc. A*, 1969, 1, 90), and its concentration in the stock solutions used was estimated by using an extinction coefficient of 1670 $cm^{-1}$ $(mol/L)^{-1}$ at 302 nm (Hughes and Nicklin; The chemistry of pernitrites. Part I. Kinetics of decomposition of pernitrious acid; *J. Chem. Soc. A*, 1968, 2, 450-452). Peroxynitrite stock solution was added into the solution of Compound 10 to provide various final concentrations, like 0, 2, 6, 10, 20, 30, 50 100, and 200 μM. Fluorescence spectra of the solutions were measured after 5 minutes under the same conditions as mentioned above. The fluorescence spectra are shown in FIG. 1. As clearly shown in FIG. 1, the fluorescence intensity of Compound 10 increase significantly after the addition of peroxynitrite. Further, FIG. 2 shows that the fluorescence intensity at 541 nm increases linearly with increasing concentration of peroxynitrite.

Comparison of Specificity of Compound 10 with Different ROS and RNS

The reactivity of Compound 10 was compared toward different reactive oxygen species (ROS) and reactive nitrogen species (RNS), including $OCl^-$, $H_2O_2$, $^1O_2$, NO, $O_2^{·-}$, $·OH$, $ONOO^-$ and alkylperoxyl radical ($ROO^·$). Different reactive oxygen species and reactive nitrogen species were added independently to 5 mL of the solution of Compound 10 (10 μM in 0.1 M potassium phosphate buffer). The changes of fluorescence intensity before and after the treatment were measured. The results are shown in FIG. 3. The reactive oxygen species and reactive nitrogen species were prepared as follows.

a. $H_2O_2$ (final 100 μM) was added and then stirred for 1 hour at 25° C.
b. (3-(1,4-Dihydro-1,4-epidioxy-1-naphthyl)propionic acid) (final 100 μM) was added and then stirred at 25° C. for 1 hour.
c. 2,2'-Azobis(2-amidinopropane)dihydrochloride (final 100 μM) was added and then stirred at 25° C. for 1 hour.
d. SNP (Sodium Nitroferricyanide (III) Dihydrate) (final 100 μM) was added and then stirred for 1 hour at 25° C.
e. $O_2^{·-}$ was generated by xanthine and xanthine oxidase. Xanthine oxidase was added firstly. After xanthine oxidase was dissolved, xanthine (final 100 μM) was added and the mixtures were stirred at 25° C. for 1 hour.
f. Ferrous chloride (final 10 μM) was added in the presence of 10 equivalences of $H_2O_2$ (100 μM).
g. $ONOO^-$ (final 10 μM) was added at 25° C.
h. NaOCl (final 10 μM) was added at 25° C. Commercial bleach was the source of NaOCl.

FIG. 3 shows that peroxynitrite leads to much stronger fluorescence enhancement of Compound 10 than any other ROS and RNS. These results demonstrated that Compound 10 has a much higher reactivity towards peroxynitrite among ROS and RNS in an abiotic system. Further, similar reactions do not proceed between the trifluoromethyl derivative of Compound 10 and any other reactive oxygen species or reactive nitrogen species present in the biological systems.

Example 9

Application of Compound 22 in Cell Assay

Murine J744.1 macrophages (ATCC, USA) were used to investigate the potential of Compound 22 (acetate form of Compound 10) for the detection of peroxynitrite in living cells. J744.1 macrophages were cultured in Dulbecco's Modified Eagle's Medium (DMEM) (Gibco) containing 10% heat-inactivated fetal bovine serum (Gibco) supplemented with 100 U/ml of penicillin and 100 μg/ml streptomycin at 37° C., 5% $CO_2$. They were subcultured by scraping and seeded on six-well plates according to manufacture's instruction. The growth medium was changed every two to three days. Cells were grown to confluence prior to experiment. Murine J744.1 macrophages were incubated with Compound 22 (20 μM) for 1 hr and then washed three times with PBS buffer. Only very weak fluorescence was observed in the absence of stimulants (FIG. 8A). The fluorescence was induced after treatment with LPS (lipopolysaccharide, 1 μg/ml) and IFN-γ (Interferon-γ, 50 ng/ml) for 4 hrs (FIG. 8B) and strong fluorescence was observed after additional stimulation by PMA (phorbol 12-myristate 13-acetate, 10 nM) for half an hour (FIG. 8C). Thus, we conclude that Compound 22 is suitable for the detection of peroxynitrite produced in stimulated Murine J744.1 macrophages.

Example 10

Highly Sensitive Detection of Peroxynitrite with Compound 12

UV-Visible Absorption Spectrum of Compound 12

Compound 12 obtained in Example 5 was dissolved in pH 7.4 0.1 M phosphate buffer containing 0.1% DMF as cosolvent to form a 1 µM solution. The absorption spectrum of the 1 µM solution of Compound 12 was measured and showed that Compound 12 has an absorption maximum at about 515 nm.

Emission Spectra of Compound 12

Compound 12 obtained in Example 5 was dissolved in DMF to a concentration of 1 mM, and then the solution was diluted to 1 µM by 0.1 M phosphate buffer (pH 7.4). The fluorescence spectrum of the 1 µM solution of Compound 12 was measured using a Hitachi F2500 fluorescence spectrometer and the photomultiplier voltage was 700 V. The slit width was 2.5 nm for both excitation and emission. The measurement was carried out at an excitation wavelength of 515 nm. The results shown in FIG. 4 indicate that Compound 12 itself is non-fluorescent.

Detection of Peroxynitrite with Compound 12

Compound 12 obtained in Example 5 was dissolved in DMF to a concentration of 1 mM, and then the solution was diluted to 1 µM by 0.1 M potassium phosphate buffer (pH 7.4). Peroxynitrite solution in 0.1 M NaOH was prepared by the method of Keith and Powell (Keith, W. G. & Powell, R. E.; Kinetics of decomposition of peroxynitrous acid; *J. Chem. Soc. A*, 1969, 1, 90), and its concentration in the stock solutions used was estimated by using an extinction coefficient of 1670 $cm^{-1}$ $(mol/L)^{-1}$ at 302 nm (Hughes and Nicklin; The chemistry of pernitrites. Part I. Kinetics of decomposition of pernitrious acid; *J. Chem. Soc. A*, 1968, 2, 450-452). Peroxynitrite stock solution was added into the solution of Compound 12 to provide various final concentrations, like 0, 1, 2, 3, 4, 5, 6, and 7 µM. Fluorescence spectra of the solutions were measured after 5 minutes under the same conditions as mentioned above. The fluorescence spectra are shown in FIG. 4. As clearly shown in FIG. 4, the fluorescence intensity of Compound 12 increase significantly after the addition of peroxynitrite. Further, the fluorescence intensity at 535 nm increases linearly with increasing concentration of peroxynitrite (data not shown).

Comparison of Specificity of Compound 12 with Different ROS and RNS

The reactivity of Compound 12 was compared toward different reactive oxygen species (ROS) and reactive nitrogen species (RNS), including $OCl^-$, $H_2O_2$, $^1O_2$, NO, $O_2^{\cdot-}$, $^{\cdot}OH$, $ONOO^-$ and alkylperoxyl radical ($ROO^{\cdot}$). Different reactive oxygen species and reactive nitrogen species were added independently to 5 mL of the solution of Compound 12 (1 µM in 0.1 M potassium phosphate buffer). The changes of fluorescence intensity before and after the treatment were measured. The results are shown in FIG. 5. The reactive oxygen species and reactive nitrogen species were prepared as follows:

i. $H_2O_2$ (final 100 µM) was added and then stirred for 1 hour at 25° C.
 j. (3-(1,4-Dihydro-1,4-epidioxy-1-naphthyl)propionic acid) (final 100 µM) was added and then stirred at 25° C. for 1 hour.
 k. 2,2'-Azobis(2-amidinopropane)dihydrochloride (final 100 µM) was added and then stirred at 25° C. for 1 hour.
 l. SNP (Sodium Nitroferricyanide (III) Dihydrate) (final 100 µM) was added and then stirred for 1 hour at 25° C.
 m. $O_2^{\cdot-}$ was generated by xanthine and xanthine oxidase. Xanthine oxidase was added firstly. After xanthine oxidase was dissolved, xanthine (final 100 µM) was added and the mixtures were stirred at 25° C. for 1 hour.
 n. Ferrous chloride (final 10 µM) was added in the presence of 10 equivalences of $H_2O_2$ (100 µM).
 o. $ONOO^-$ (final 10 µM) was added at 25° C.
 p. NaOCl (final 10 µM) was added at 25° C. Commercial bleach was the source of NaOCl.

FIG. 5 shows that peroxynitrite leads to much stronger fluorescence enhancement of Compound 12 than any other ROS and RNS. These results demonstrated that Compound 12 has a much higher reactivity towards peroxynitrite among ROS and RNS in an abiotic system. Further, similar reactions do not proceed between the phenol derivative of Compound 12 and any other reactive oxygen species or reactive nitrogen species present in the biological systems.

Example 11

Highly Sensitive Detection of Hypochlorite with Compound 14

UV-Visible Absorption Spectrum of Compound 14

Compound 14 obtained in Example 6 was dissolved in pH 7.4 0.1 M phosphate buffer containing 0.1% DMF as cosolvent to form a 1 µM solution. The absorption spectrum of the 1 µM solution of Compound 14 was measured and showed that Compound 14 has an absorption maximum at about 515 nm.

Emission Spectra of Compound 14

Compound 14 obtained in Example 6 was dissolved in DMF to a concentration of 1 mM, and then the solution was diluted to 1 µM by 0.1 M phosphate buffer (pH 7.4). The fluorescence spectrum of the 1 µM solution of Compound 14 was measured using a Hitachi F2500 fluorescence spectrometer and the photomultiplier voltage was 700 V. The slit width was 2.5 nm for both excitation and emission. The measurement was carried out at an excitation wavelength of 515 nm. The results shown in FIG. 6 indicate that Compound 14 itself is non-fluorescent.

Detection of Peroxynitrite with Compound 14

Compound 14 obtained in Example 6 was dissolved in DMF to a concentration of 1 mM, and then the solution was diluted to 1 µM by 0.1 M potassium phosphate buffer (pH 7.4). Commercial bleach was the source of NaOCl. The concentration of NaOCl was determined by titration with sodium thiosulfate solution which was standardized by the titration with $KIO_3$. Then NaOCl was added to provide final concentrations of 0, 2, 3, 4, 5, 6, 7, and 8 µM. Fluorescence spectra of the solutions were measured after 5 minutes under the same conditions as mentioned above. The fluorescence spectra are shown in FIG. 6. As clearly shown in FIG. 6, the fluorescence intensity of Compound 14 increase significantly after the addition of hypochlorite. Further, the fluorescence intensity at 535 nm increases linearly with increasing concentration of hypochlorite.

Comparison of Specificity of Compound 14 with Different ROS and RNS

The reactivity of Compound 14 was compared toward different reactive oxygen species (ROS) and reactive nitrogen species (RNS), including $OCl^-$, $H_2O_2$, $^1O_2$, NO, $O_2^{\cdot-}$, $^{\cdot}OH$, $ONOO^-$ and alkylperoxyl radical ($ROO^{\cdot}$). Different reactive oxygen species and reactive nitrogen species were added independently to 5 mL of the corresponding solution of Compound 14 (1 μM in 0.1 M potassium phosphate buffer). The changes in fluorescence intensity before and after the treatment were measured. The results are shown in FIG. 7. The reactive oxygen species and reactive nitrogen species were prepared as follows:

a. $H_2O_2$ (final 100 μM) was added and then stirred for 1 hour at 25° C.
b. (3-(1,4-Dihydro-1,4-epidioxy-1-naphthyl)propionic acid) (final 100 μM) was added and then stirred at 25° C. for 1 hour.
c. 2,2'-Azobis(2-amidinopropane)dihydrochloride (final 100 μM) was added and then stirred at 25° C. for 1 hour.
d. SNP (Sodium Nitroferricyanide (III) Dihydrate) (final 100 μM) was added and then stirred for 1 hour at 25° C.
e. $O_2^{\cdot -}$ was generated by xanthine and xanthine oxidase. Xanthine oxidase was added firstly. After xanthine oxidase was dissolved, xanthine (final 100 μM) was added and the mixtures were stirred at 25° C. for 1 hour.
f. Ferrous chloride (final 10 μM) was added in the presence of 10 equivalences of $H_2O_2$ (100 μM).
g. $ONOO^-$ (final 10 μM) was added at 25° C. Peroxynitrite was prepared as stated in Example 4.
h. NaOCl (final 10 μM) was added at 25° C.

FIG. 7 shows that hypochlorite leads to much stronger fluorescence enhancement of Compound 14 than any other ROS and RNS. These results demonstrated that Compound 14 has a much higher reactivity towards hypochlorite among ROS and RNS in an abiotic system. Further, similar reactions do not proceed between the aniline derivative of Compound 14 and any other reactive oxygen species or reactive nitrogen species present in the biological systems.

Example 12

Application of Compounds 12 and 12a in Cell Assay

Murine J744.1 macrophages (ATCC, USA) were used to investigate the potential of Compound 12 and 12a for the detection of peroxynitrite in living cells. J744.1 macrophages were cultured in Dulbecco's Modified Eagle's Medium (DMEM) (Gibco) containing 10% heat-inactivated fetal bovine serum (Gibco) supplemented with 100 U/ml of penicillin and 100 μg/ml streptomycin at 37° C., 5% $CO_2$. They were subcultured by scraping and seeded on six-well plates according to manufacture's instruction. The growth medium was changed every two to three days. Cells were grown to confluence prior to experiment. Murine J744.1 macrophages were incubated with Compound 12 or 12a (20 μM) for 1 hr and then washed three times with PBS buffer. Only very weak fluorescence was observed in the absence of stimulants (FIG. 9B and FIG. 10A). The fluorescence was induced after treatment with LPS (lipopolysaccharide, 1 μg/ml) for 4 hrs (FIG. 9D and FIG. 10B). Also the green color from Compound 12 was found to be colocalized with the red color from a mitochondrial dye MitoTracker Red CMXRos (FIG. 9F). The results indicate that Compound 12 may selectively localize in mitochondrials.

Example 13

Detection of Peroxynitrite with Compound 30

UV-Visible Absorption Spectrum of Compound 30
Compound 30 obtained in Example 7 was dissolved in pH 7.4 0.1 M phosphate buffer containing 0.1% DMF as cosolvent to form a 10 μM solution. The absorption spectrum of the 10 μM solution of Compound 30 was measured. The absorption maximum of Compound 30 was found to be at about 540 nm.

Emission Spectra of Compound 30
Compound 30 obtained in Example 7 was dissolved in DMF to a concentration of 10 mM, and then the solution was diluted to 10 μM by 0.1 M phosphate buffer (pH 7.4). The fluorescence spectrum of the 10 μM solution of Compound 30 was measured using a Hitachi F7000 fluorescence spectrometer and the photomultiplier voltage was 900 V. The slit width was 2.5 nm for both excitation and emission. The measurement was carried out at an excitation wavelength of 520 nm. The results shown in FIG. 11 indicate that Compound 30 itself may be non-fluorescent.

Figure 11:
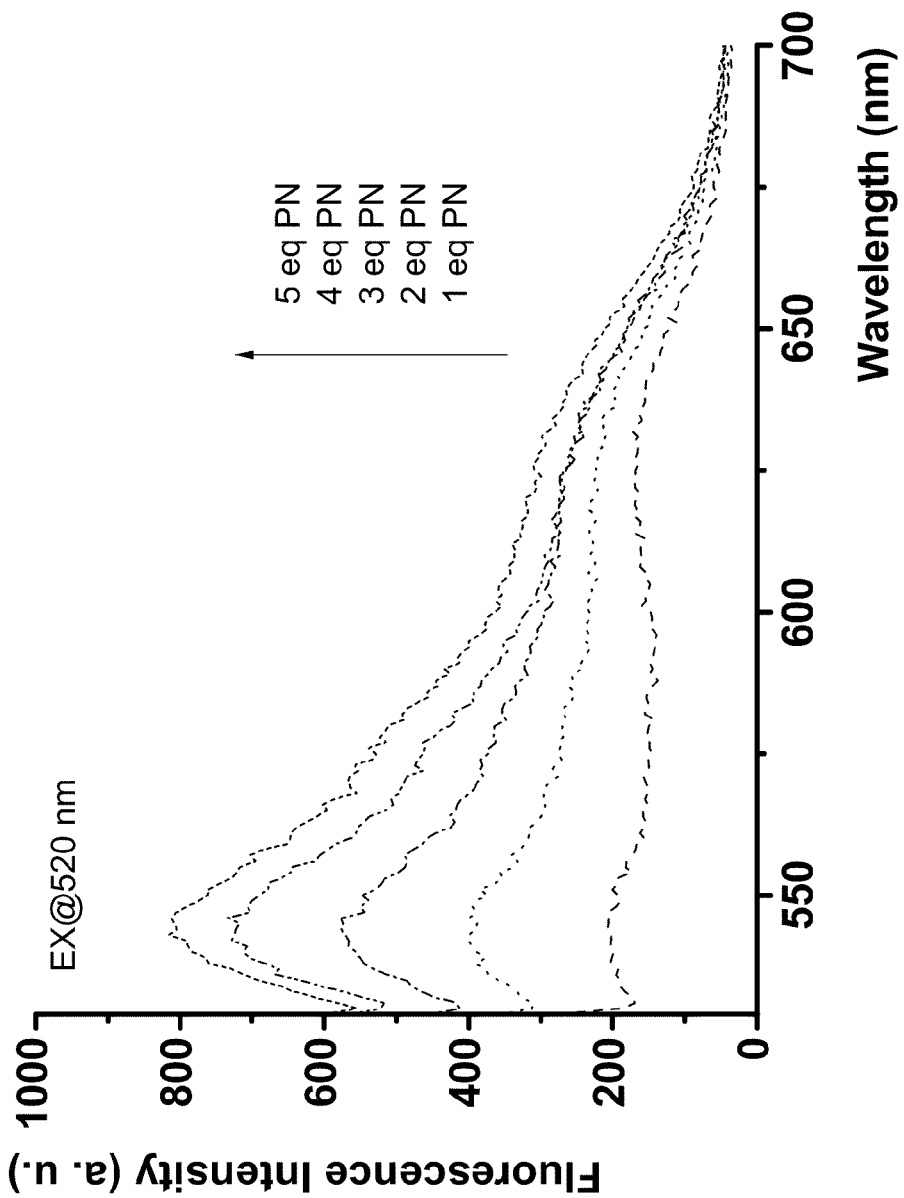
FIG. 11 depicts fluorescence spectra showing fluorescence intensities of 10 μM of Compound 30 in response to different concentrations of peroxynitrite at different wavelengths. The spectra were acquired with excitation at 520 nm in 0.1 M potassium phosphate buffer at pH 7.4 where 0.1% DMF was used as a cosolvent.

Detection of Peroxynitrite with Compound 30
Compound 30 obtained in Example 7 was dissolved in DMF to a concentration of 10 mM, and then the solution was diluted to 10 μM by 0.1 M potassium phosphate buffer (pH 7.4). Peroxynitrite solution in 0.1 M NaOH was prepared by the method of Keith and Powell (Keith, W. G. & Powell, R. E.; Kinetics of decomposition of peroxynitrous acid; *J. Chem. Soc. A*, 1969, 1, 90), and its concentration in the stock solutions used was estimated by using an extinction coefficient of 1670 $cm^{-1}$ $(mol/L)^{-1}$ at 302 nm (Hughes and Nicklin; The chemistry of pernitrites. Part I. Kinetics of decomposition of pernitrious acid; *J. Chem. Soc. A*, 1968, 2, 450-452). Peroxynitrite stock solution was added into the solution of Compound 30 to provide various final concentrations. Fluorescence spectra of the solutions were measured after 5 minutes under the same conditions as mentioned above. The fluorescence spectra are shown in FIG. 11. As clearly shown in FIG. 11, the fluorescence intensity of Compound 30 increases significantly after the addition of peroxynitrite.

As demonstrated above, embodiments disclosed herein provide various compounds that can be used as fluorogenic probes for detecting, measuring and/or screening peroxynitrite. While this disclosure has been described with respect to a limited number of embodiments, the specific features of one embodiment should not be attributed to other embodiments. No single embodiment is representative of all aspects of this disclosure. In some embodiments, the compositions or methods may include numerous compounds or steps not mentioned herein. In other embodiments, the compositions or methods do not include, or are substantially free of, any compounds or steps not enumerated herein. Variations and modifications from the described embodiments exist. For example, the reagent composition disclosed herein need not comprising only the fluorogenic probes disclosed herein. It can comprise any type of compounds generally suitable for fluorogenic probes. It is noted that the methods for making and using the fluorogenic probes disclosed herein are described with reference to a number of steps. These steps can be practiced in any sequence. One or more steps may be omitted or combined but still achieve substantially the same results. The appended claims intend to cover all such variations and modifications as falling within the scope of this disclosure.

All publications and patent applications mentioned in this specification are herein incorporated by reference to the same extent as if each individual publication or patent application was specifically and individually indicated to be incorporated by reference. It is to be understood that this disclosure has been described in detailed by way of illustration and example in order to acquaint others skilled in the art with the invention, its principles, and its practical application. Further, the specific embodiments provided herein as set forth are not intended to be exhaustive or to limit the disclosure, and that many alternatives, modifications, and variations will be apparent to those skilled in the art in light of the foregoing examples and detailed description. Accordingly, this disclosure is intended to embrace all such alternatives, modifications, and variations that fall within the spirit and scope of the following claims. While some of the examples and descriptions above include some conclusions about the way the compounds, compositions and methods may function, the inventors do not intend to be bound by those conclusions and functions, but put them forth only as possible explanations in light of current understanding.

What is claimed is:

1. An aromatic amine compound of Formula (I):

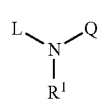
(I)

wherein $R^1$ is hydrogen, alkyl, halogenated alkyl, heteroalkyl, alkenyl, alkynyl, aryl, aralkyl, alkaryl, heterocyclyl, cycloalkyl, cycloalkenyl or cycloalkynyl;

L is formula (II):

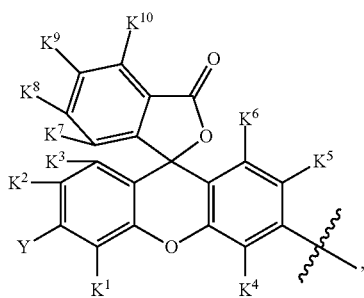
(II)

or a tautomer thereof, wherein Y is O-A, S-A or $NR^2R^3$;

each of $R^2$ and $R^3$ is independently H, alkyl, halogenated alkyl, alkenyl, alkynyl, alkoxyalkyl, heteroalkyl, cycloalkyl, cycloalkenyl, cycloalkynyl, heterocyclyl, aminoalkyl, aryl, alkaryl, arylalkyl, alkyloxy, carboxyalkyl, alkylamido, alkoxyamido, sulfonylaryl or acyl;

A is H, alkyl, alkenyl, alkynyl, alkoxyalkyl, heteroalkyl, cycloalkyl, cycloalkenyl, cycloalkynyl, heterocyclyl, aminoalkyl, aryl, alkaryl, arylalkyl, carboxyalkyl, alkoxycarbonyl, acyl or aminocarbonyl;

each of $K^1$-$K^{10}$ is independently H, halo, alkyl, halogenated alkyl, heteroalkyl, alkenyl, alkynyl, aryl, aralkyl, alkaryl, heterocyclyl, cycloalkyl, cycloalkenyl, cycloalkynyl, hydroxyalkyl, aminoalkyl, amino, alkylamino, arylamino, dialkylamino, alkylarylamino, diarylamino, acylamino, hydroxy, thiol, thioalkyl, alkoxy, alkylthio, alkoxyalkyl, aryloxy, arylalkoxy, acyloxy, cyano, nitro, sulfhydryl, carbamoyl, trifluoromethyl, phenoxy, benzyloxy, sulfonyl, phosphonyl, sulfonate ester, phosphate ester, —C(=O)—$P^1$ or —C(=O)—Z—$P^2$;

each of $P^1$ and $P^2$ is independently hydrogen, halo, alkoxy, hydroxy, thiol, alkyl, alkenyl, alkynyl, cycloalkyl, cycloalkenyl, cycloalkynyl, aryl, alkaryl, arylalkyl, carbamate, amino, alkylamino, arylamino, dialkylamino, alkylarylamino, diarylamino, alkylthio, heteroalkyl, or heterocyclyl having from 3 to 7 ring atoms; and Z is alkylene, alkynylene, alkynylene, arylene, aralkylene or alkarylene; and Q is substituted or unsubstituted phenyl having formula (VIIa):

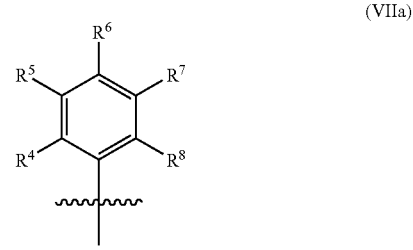
(VIIa)

wherein each of $R^4$, $R^5$, $R^6$, $R^7$ and $R^8$ is independently H, alkyl, alkenyl, alkynyl, heteroalkyl, cycloalkyl, cycloalkenyl, cycloalkynyl, aryl, alkylaryl, arylalkyl, heterocyclyl, hydroxy, alkoxy, alkoxyalkyl, alkoxyalkoxy, acyl, alkylcarbonylalkyl, halogenated alkylcarbonylalkyl, aminoalkyl, carboxyalkyl, alkoxycarbonyl, alkoxycarbonylalkyl, aminocarbonyl, or $NR^9R^{10}$ or $R^4$ and $R^5$ together, $R^5$ and $R^6$ together, $R^6$ and $R^7$ together or $R^7$ and $R^8$ together forming a 5- or 6-membered cycloalkyl, heterocyclyl, aryl or heteroaryl ring fused with the phenyl ring of formula (VIIa); and each of $R^9$ and $R^{10}$ is independently H, alkyl, alkenyl, alkynyl, alkoxyalkyl, alkanoyl, alkenoyl, alkynoyl, cycloalkyl, cycloalkenyl, cycloalkynyl, aryl, alkaryl, arylalkyl, aryloyl, or polyether;

with the proviso that when L has formula (II) where Y is $NR^2R^3$, then $R^6$ of Q is hydroxy, alkenyl, alkynyl, heteroalkyl, cycloalkyl, cycloalkenyl, cycloalkynyl, aryl, heterocyclyl, alkoxyalkyl, alkoxyalkoxy, acyl, alkylcarbonylalkyl, halogenated alkylcarbonylalkyl, carboxyalkyl, alkoxycarbonyl, alkoxycarbonylalkyl or aminocarbonyl, or $R^4$ and $R^5$ together, $R^5$ and $R^6$ together, $R^6$ and $R^7$ together or $R^7$ and $R^8$ together form a 5- or 6-membered cycloalkyl, heterocyclyl, aryl or heteroaryl ring fused with the phenyl ring of formula (VIIa).

2. The aromatic amine compound of claim 1, wherein $R^6$ is —$OCH_2OCH_3$, OH, $NR^9R^{10}$, —$CH_2CH_2C(=O)CF_3$, or —$CH_2CH_2C(=O)OCH_3$ where each of $R^9$ and $R^{10}$ is independently H or alkyl; and each of $R^4$, $R^5$, $R^7$ and $R^8$ is H.

3. The aromatic amine compound of claim 2, wherein $R^6$ is OH, $NH_2$ or —$CH_2CH_2C(=O)CF_3$.

4. The aromatic amine compound of claim 1, wherein $R^1$ is H, alkyl, halogenated alkyl, heteroalkyl, alkenyl, alkynyl, aryl, aralkyl, alkaryl, heterocyclyl, cycloalkyl, cycloalkenyl, and cycloalkynyl; each of $R^4$, $R^5$, $R^6$, $R^7$ and $R^8$ is independently H, halogen, alkyl, alkoxy, or polyether; $R^6$ is $OR^{11}$ or $CH_2CH_2COR^{12}$, where $R^{11}$ is H, alkyl, alkoxyalkyl, alkanoyl, or polyether; $R^{12}$ is an electron-withdrawing group selected from $CF_3$, halogen-substituted lower alkyl, or (C=O)—O—$V^2$; and $V^2$ is a group selected from alkyl, alkenyl, alkynyl, cycloalkyl, cycloalkenyl, cycloalkynyl, aryl, alkaryl or arylalkyl.

5. The aromatic amine compound of claim 1, wherein L has one of the following formulae:
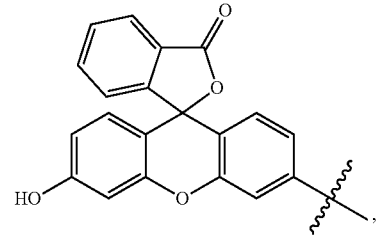 (a)
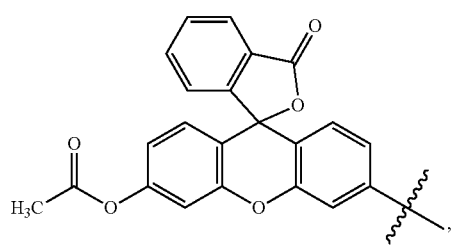 (b)
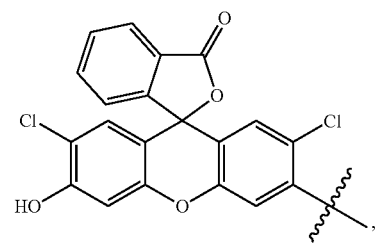 (d)
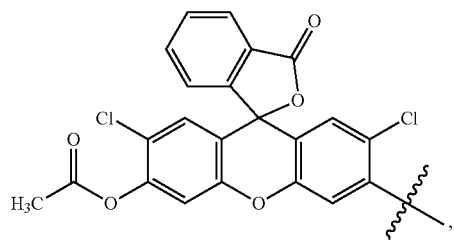 (e)
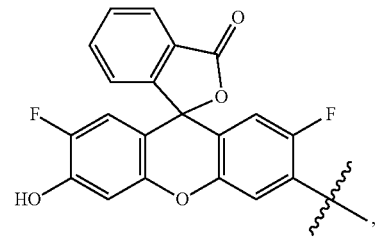 (g)
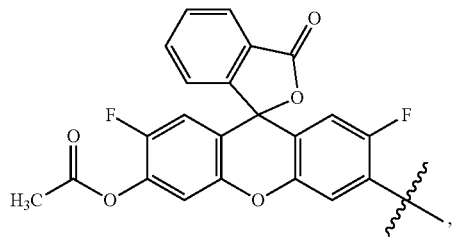 (h)
-continued
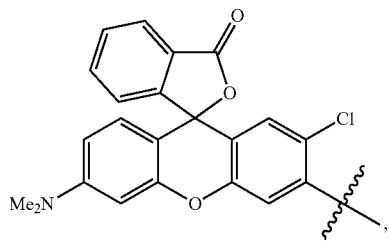 (j)
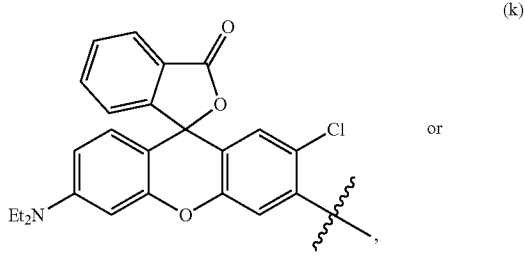 (k) or
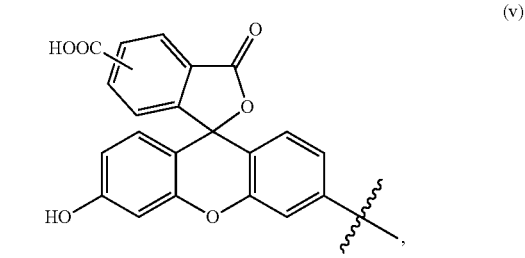 (v)
or a tautomer thereof, wherein each of said formulae is independently unsubstituted or substituted.
6. The aromatic amine compound of claim 1, wherein the aromatic amine compound is one of the following Compounds:
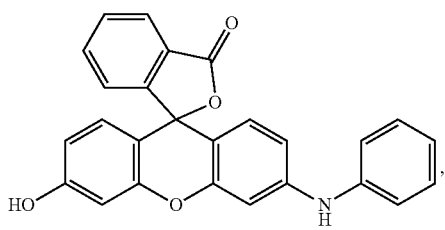 (1a)
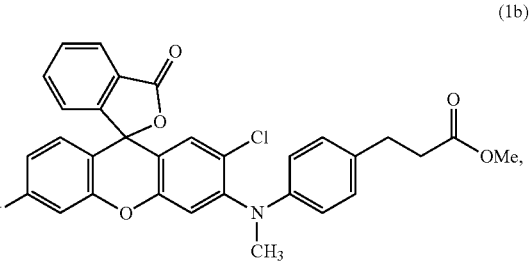 (1b)

(1c)
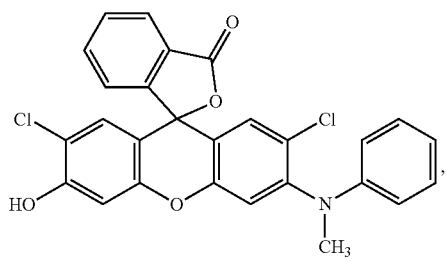
(22)
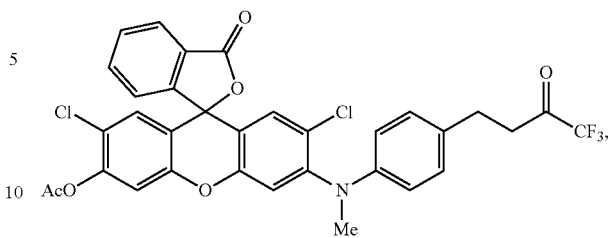
or a tautomer thereof, wherein each of said Compounds is independently substituted or unsubstituted.
7. A composition comprising the aromatic amine compound of claim 1 and a carrier.
8. The composition of claim 7, wherein the aromatic amine compound is Compound (10), Compound (12), Compound (12a), or Compound (22):
(1d)
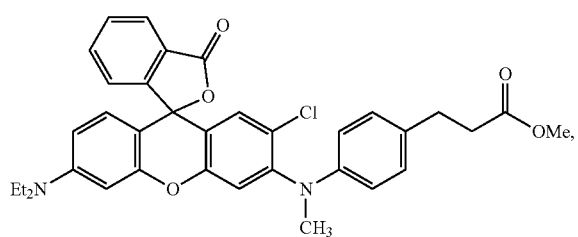
(10)
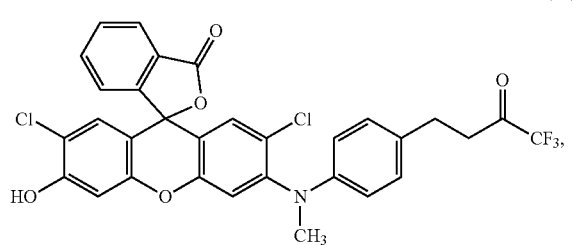
(10)
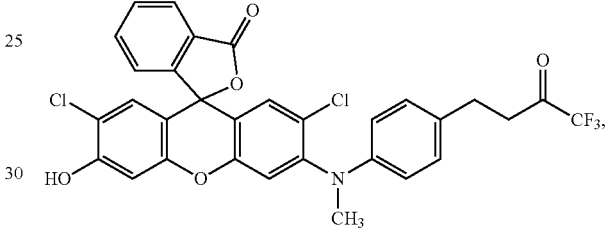
(12)
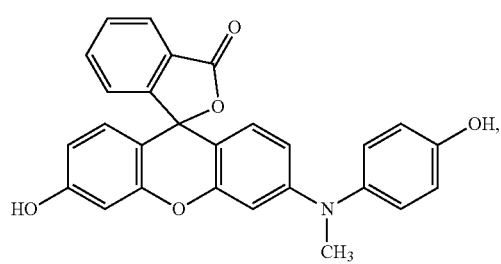
(12)
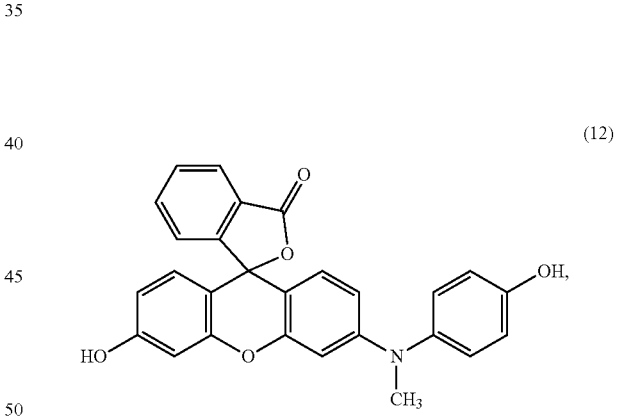
(12a)
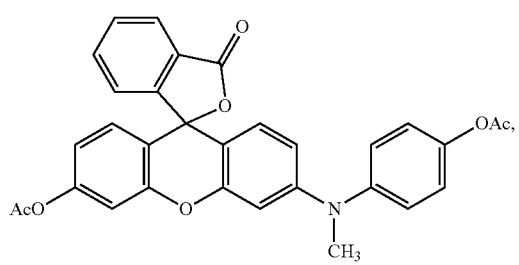
(12a)
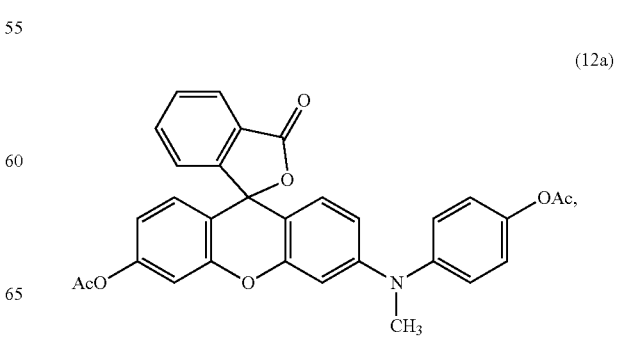
(14)
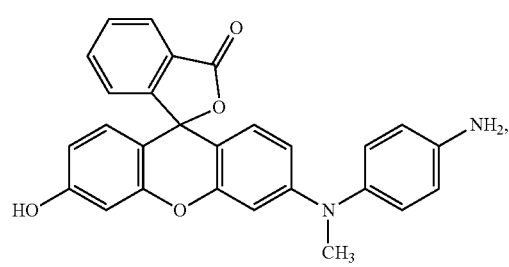

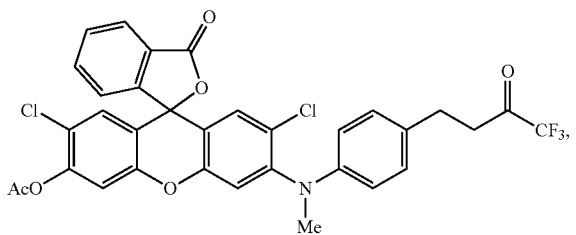
(22)
or a tautomer thereof, or a combination thereof.
9. The composition of claim 7, wherein the composition further comprises a solvent, an acid, a base, a buffer solution or a combination thereof.
10. The composition of claim 7, wherein the aromatic amine compound is Compound (14):
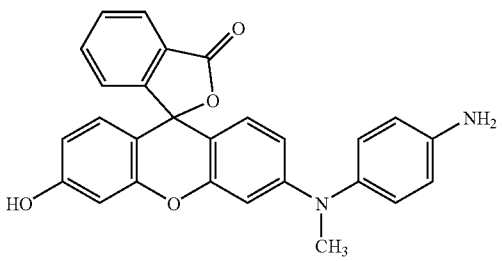
(14)
or a tautomer thereof.
\* \* \* \* \*

UNITED STATES PATENT AND TRADEMARK OFFICE
CERTIFICATE OF CORRECTION

PATENT NO. : 8,114,904 B2
APPLICATION NO. : 12/417672
DATED : February 14, 2012
INVENTOR(S) : Dan Yang and Tao Peng It is certified that error appears in the above-identified patent and that said Letters Patent is hereby corrected as shown below:

Column 2,
Line 45, "522-53 1)." should read --522-531).--.

Column 3,
Line 14, ".OH," should read --•OH,--.

Lines 30-40, Formula II, " 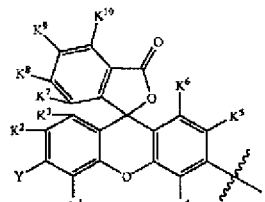 " should read -- 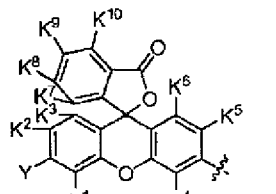 --.

Lines 45-55, Formula III, " 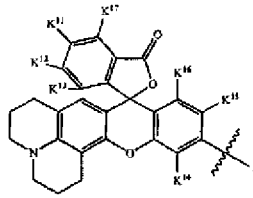 " should read -- 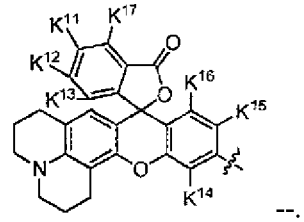 --.

Column 6,
Line 55, "K is H or halo." should read --$K^{15}$ is H or halo.--.

Column 7,
Line 9, "formula (VIa) is" should read --formula (VIIa) is--.

Signed and Sealed this
Seventeenth Day of July, 2012

David J. Kappos
*Director of the United States Patent and Trademark Office*

Column 8,

Lines 5-10, Compound 22, " 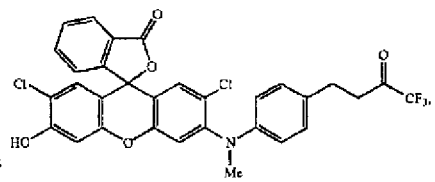 " should read

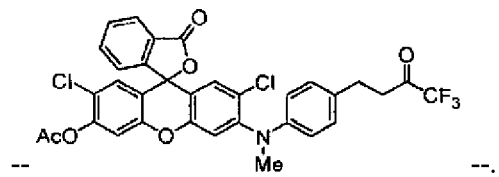
--          --.

Column 9,
Line 40, "ROO. and H₂O₂" should read --ROO• and H₂O₂--.
Line 41, "concentration of .OH," should read --concentration of •OH,--.
Lines 51-52, "ROO. and ... of .OH," should read --ROO• and ... of •OH,--.
Line 61, "ROO., ... , .OH," should read --ROO•, ... , •OH,--.

Column 14,
Line 30, "peroxynitrite (ONOO)." should read --peroxynitrite (ONOO⁻).--.

Column 15,
Line 33, ".OH," should read --•OH,--.

Column 18,

Lines 25-35, Formula II, " 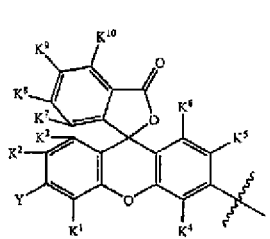 " should read -- 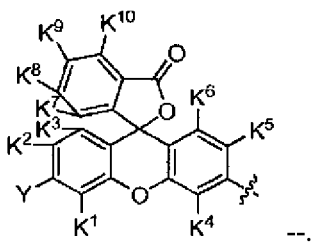 --.

Column 19,

Formula II, 1ˢᵗ occurrence, " 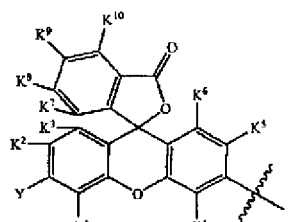 " should read -- 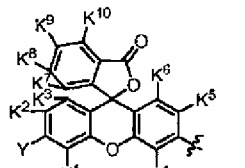 --.

CERTIFICATE OF CORRECTION (continued)
U.S. Pat. No. 8,114,904 B2

Column 19,

Formula II, 2<sup>nd</sup> occurrence, " 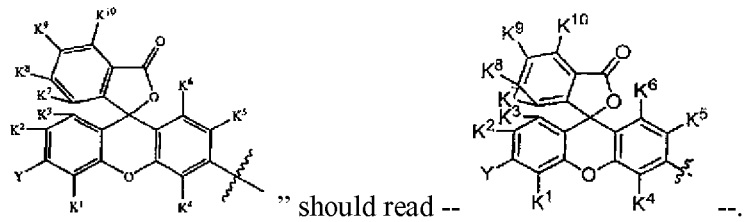 " should read -- --.

Lines 50-65, Formula III, " 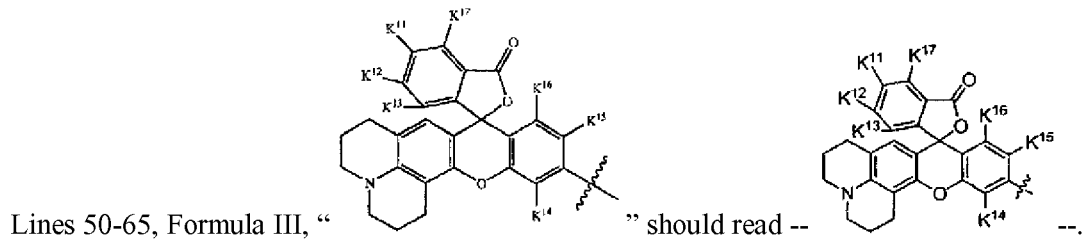 " should read -- --.

Column 21,

Formula III, " 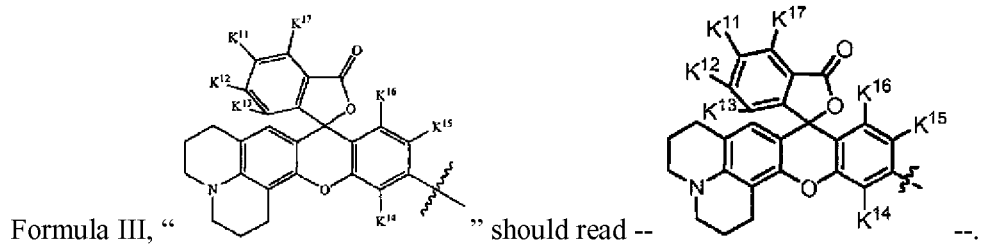 " should read -- --.

Column 22,
Line 20, "(IIa)" should read --(IIIa)--.

Column 24,
Line 51, "or $N^+R^2R^{3'}$" should read --$N^+R^2R^{3'}$.--.

Column 34,
Line 9, "formula (VIa)" should read --formula (VIIa)--.
Line 11, "or $CH_2CH_2COR$" should read --or $CH_2CH_2COR^{12}$--.
Line 59, "formula (VIIb)" should read --formula (VIIIb)--.

Column 40,
Line 55, "formula (VIIb)" should read --formula (VIIIb)--.
Line 58, "formula (VIIb)" should read --formula (VIIIb)--.
Line 60, "formula (VIIb)" should read --formula (VIIIb)--.
Lines 64-65, "formula (VIIb)" should read --formula (VIIIb)--.

Column 41,
Lines 1-2, "formula (VIII), (VIII)" should read --formula (VIII), (IX)--.

Column 46,
Line 3, ".OH," should read --•OH,--.

Column 59,
Line 44, "serve to" should read --serves to--.

Column 68,
Line 15, "(M⁻; 20)" should read --(M⁺; 20)--.

Column 78,
Line 52, "M⁻; 23)" should read --(M⁺; 23)--.

Column 82,
Lines 34-35, "1069, 1037, 943, 834" should read --106.9, 103.7, 94.3, 83.4--.

Column 89,
Line 67, "increase significantly" should read --increases significantly--.

Column 96,
Line 32, "aryl orheteroaryl ring" should read --aryl or heteroaryl ring--.